US011224735B2

(12) United States Patent
Forsell

(10) Patent No.: US 11,224,735 B2
(45) Date of Patent: *Jan. 18, 2022

(54) HEART HELP DEVICE, SYSTEM AND METHOD

(71) Applicant: Peter Forsell, Zug (CH)

(72) Inventor: Peter Forsell, Zug (CH)

(*) Notice: Subject to any disclaimer, the term of this patent is extended or adjusted under 35 U.S.C. 154(b) by 104 days.

This patent is subject to a terminal disclaimer.

(21) Appl. No.: 15/262,063

(22) Filed: Sep. 12, 2016

(65) Prior Publication Data

US 2017/0065756 A1    Mar. 9, 2017

Related U.S. Application Data

(60) Continuation of application No. 14/228,253, filed on Mar. 28, 2014, now Pat. No. 9,440,014, which is a
(Continued)

(30) Foreign Application Priority Data

| Oct. 10, 2008 | (SE) | 0802139-6 |
| Oct. 10, 2008 | (SE) | 0802140-4 |
| Oct. 10, 2008 | (SE) | 0802142-0 |
| Oct. 10, 2008 | (SE) | 0802143-8 |
| Oct. 10, 2008 | (SE) | 0802144-6 |
| Oct. 12, 2008 | (SE) | 0802141-2 |

(51) Int. Cl.
*A61M 1/10* (2006.01)
*A61M 60/857* (2021.01)
(Continued)

(52) U.S. Cl.
CPC .......... *A61M 60/857* (2021.01); *A61B 1/018* (2013.01); *A61B 1/04* (2013.01); *A61B 17/320016* (2013.01); *A61M 1/04* (2013.01); *A61M 1/3627* (2013.01); *A61M 60/122* (2021.01); *A61M 60/148* (2021.01); *A61M 60/268* (2021.01); *A61M 60/40* (2021.01); *A61M 60/50* (2021.01); *A61M 60/871* (2021.01);
(Continued)

(58) Field of Classification Search
CPC .................................. A61M 1/10; A61M 1/12
See application file for complete search history.

(56) References Cited

U.S. PATENT DOCUMENTS

| 6,099,460 A * | 8/2000 | Denker | A61M 1/1055 600/12 |
| 6,258,021 B1 | 7/2001 | Wilk | |

(Continued)

FOREIGN PATENT DOCUMENTS

| WO | 98030271 A1 | 7/1998 |
| WO | 20040093731 A2 | 11/2004 |

*Primary Examiner* — Matthew W Schall

(57) ABSTRACT

The present invention relates to an implantable device for improving the pump function of the heart of a human patient by applying an external force on the heart muscle, said device comprising at least one pump device comprising: a first part having a first surface, and a second part having a second surface. The first part is displaceable in relation to the second part and said first and second surfaces abut each other, at least partially. The second part exerts, directly or indirectly, force on an external part of said heart muscle.

17 Claims, 59 Drawing Sheets

Related U.S. Application Data division of application No. 13/123,586, filed as application No. PCT/SE2009/000449 on Oct. 12, 2009, now Pat. No. 8,696,745.

(60) Provisional application No. 61/202,393, filed on Feb. 25, 2009, provisional application No. 61/202,380, filed on Feb. 24, 2009, provisional application No. 61/202,383, filed on Feb. 24, 2009, provisional application No. 61/202,382, filed on Feb. 24, 2009, provisional application No. 61/202,405, filed on Feb. 25, 2009, provisional application No. 61/202,406, filed on Feb. 25, 2009, provisional application No. 61/202,407, filed on Feb. 25, 2009, provisional application No. 61/202,404, filed on Feb. 25, 2009.

(51) Int. Cl.

| | |
|---|---|
| *A61B 1/018* | (2006.01) |
| *A61B 1/04* | (2006.01) |
| *A61B 17/32* | (2006.01) |
| *A61M 1/04* | (2006.01) |
| *A61M 1/36* | (2006.01) |
| *A61M 60/40* | (2021.01) |
| *A61M 60/50* | (2021.01) |
| *A61M 60/122* | (2021.01) |
| *A61M 60/148* | (2021.01) |
| *A61M 60/268* | (2021.01) |
| *A61M 60/871* | (2021.01) |
| *A61M 60/894* | (2021.01) |
| *A61N 1/362* | (2006.01) |
| *A61N 1/39* | (2006.01) |

(52) U.S. Cl.
 CPC ......... *A61M 60/894* (2021.01); *A61N 1/3627* (2013.01); *A61M 2205/32* (2013.01); *A61M 2205/33* (2013.01); *A61M 2205/3303* (2013.01); *A61M 2205/8243* (2013.01); *A61M 2230/04* (2013.01); *A61N 1/3962* (2013.01)

(56) References Cited

U.S. PATENT DOCUMENTS 9,364,595 B2 * 6/2016 Forsell .................. A61M 1/12
2006/0047228 A1   3/2006 Petelenz
2006/0155159 A1   7/2006 Melvin

* cited by examiner

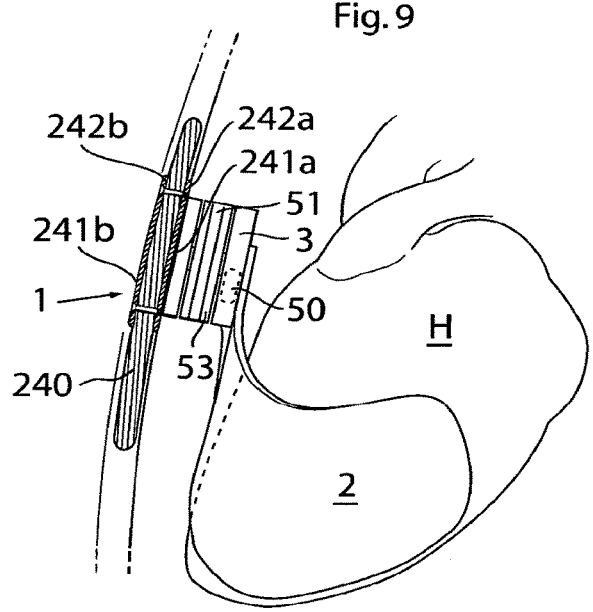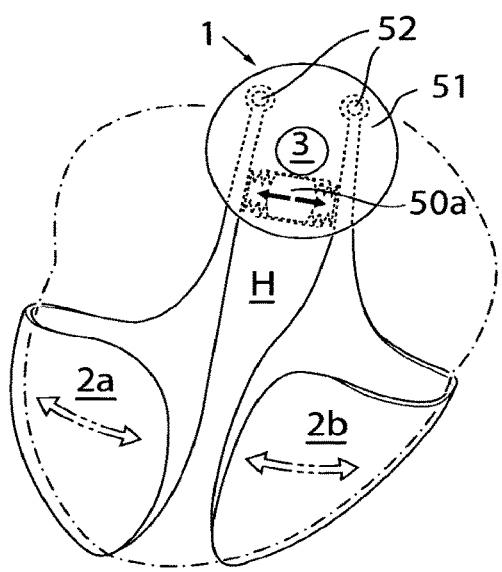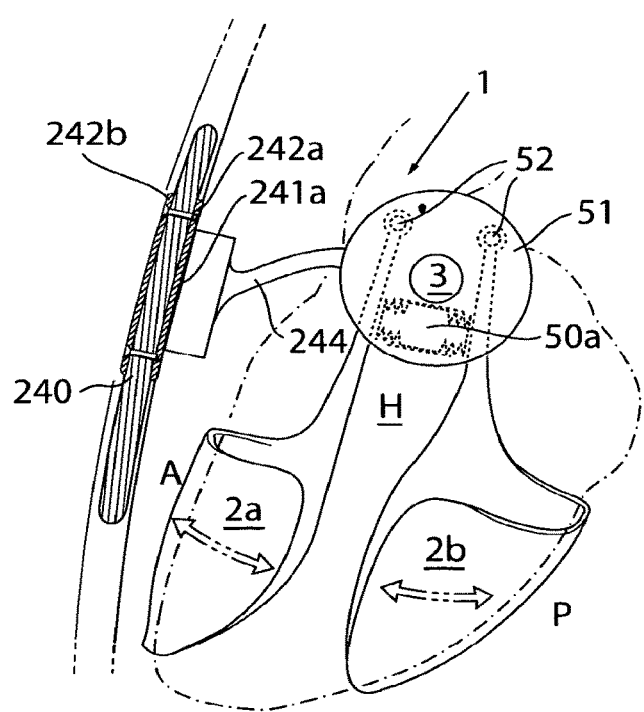

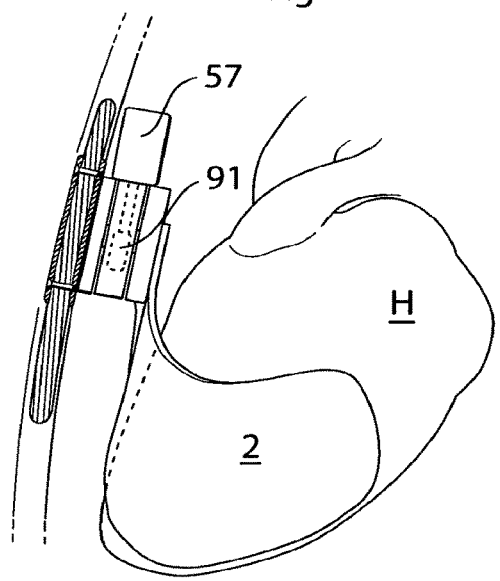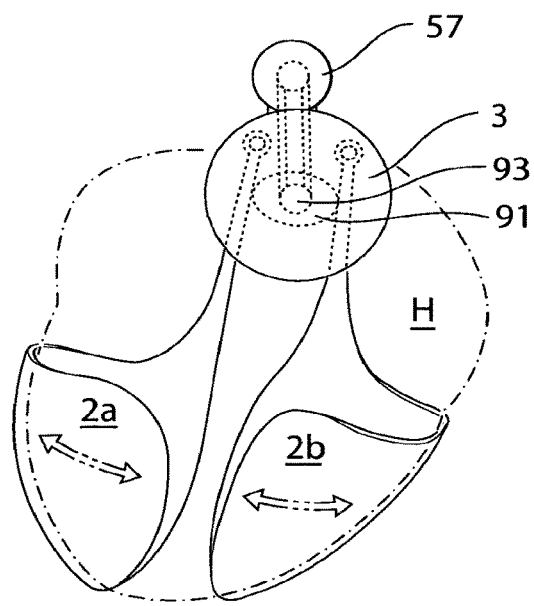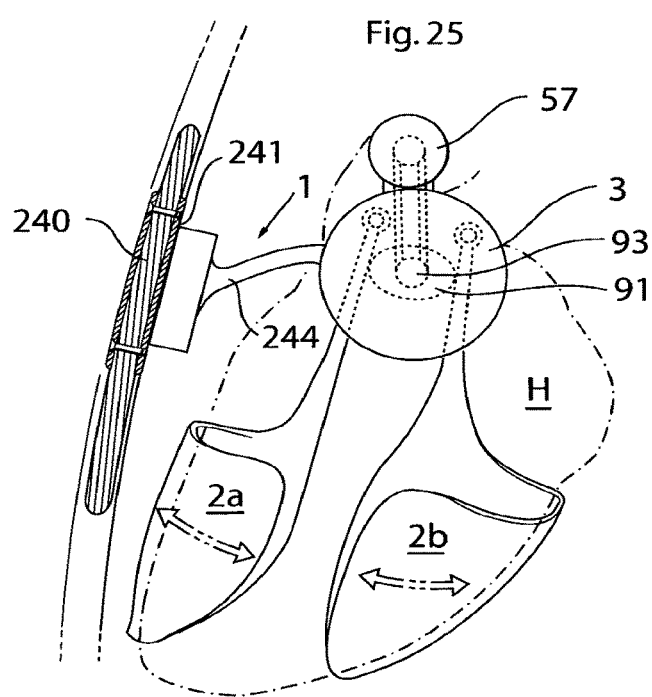

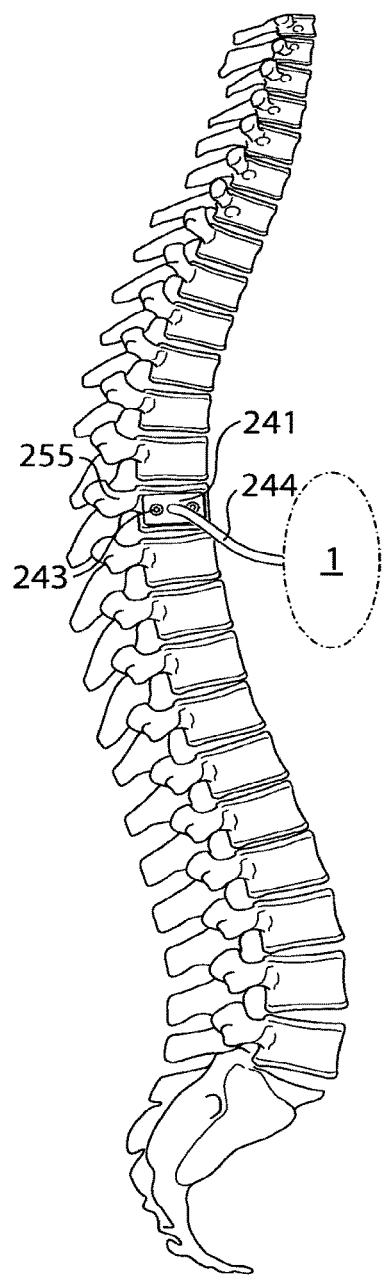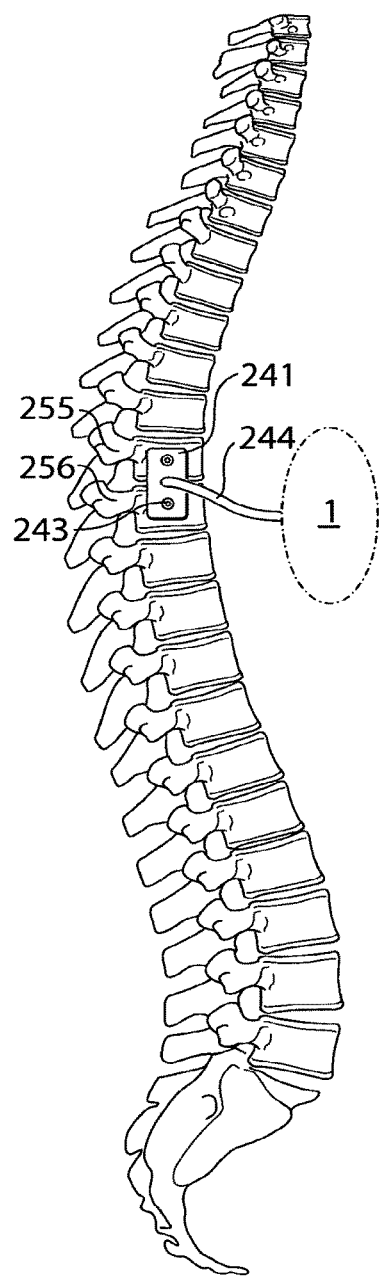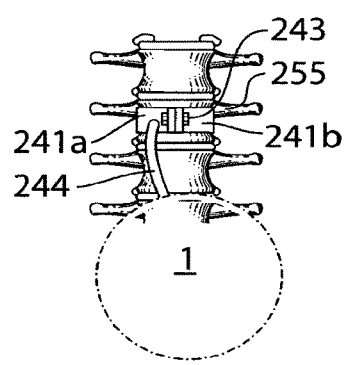

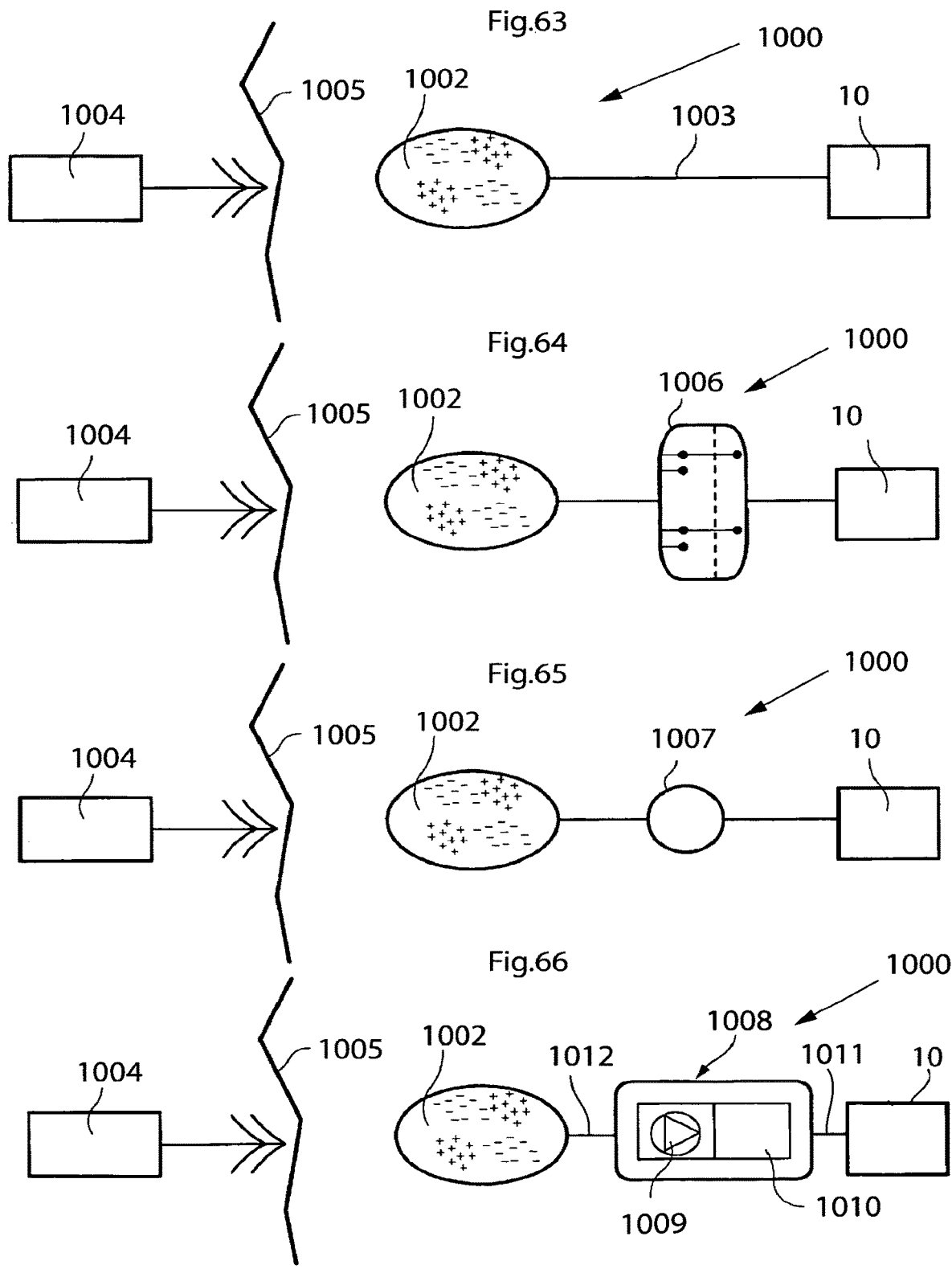

Fig.85
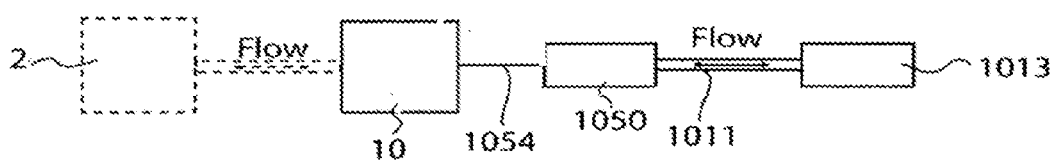
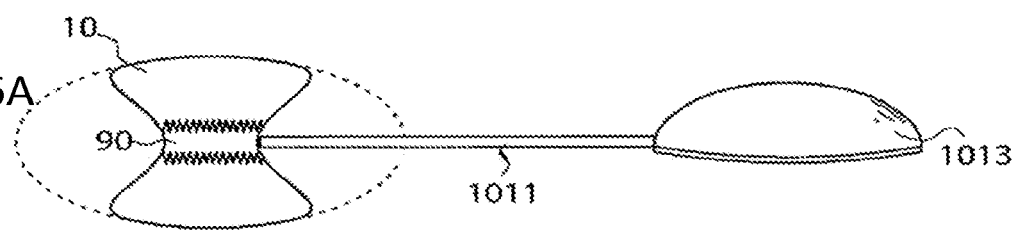
Fig. 86A
Fig. 86B
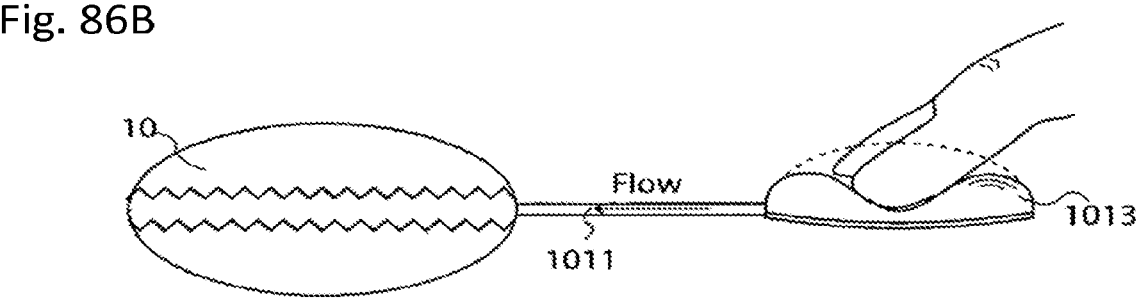
Fig. 86C
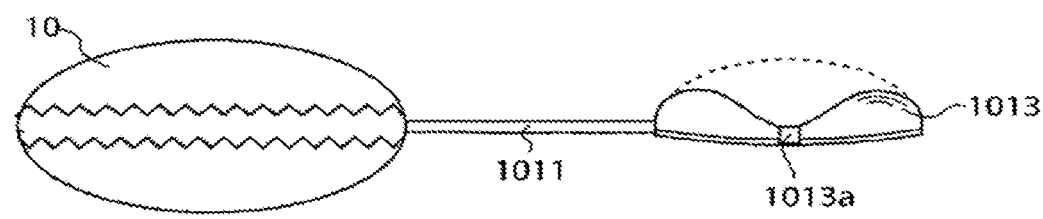

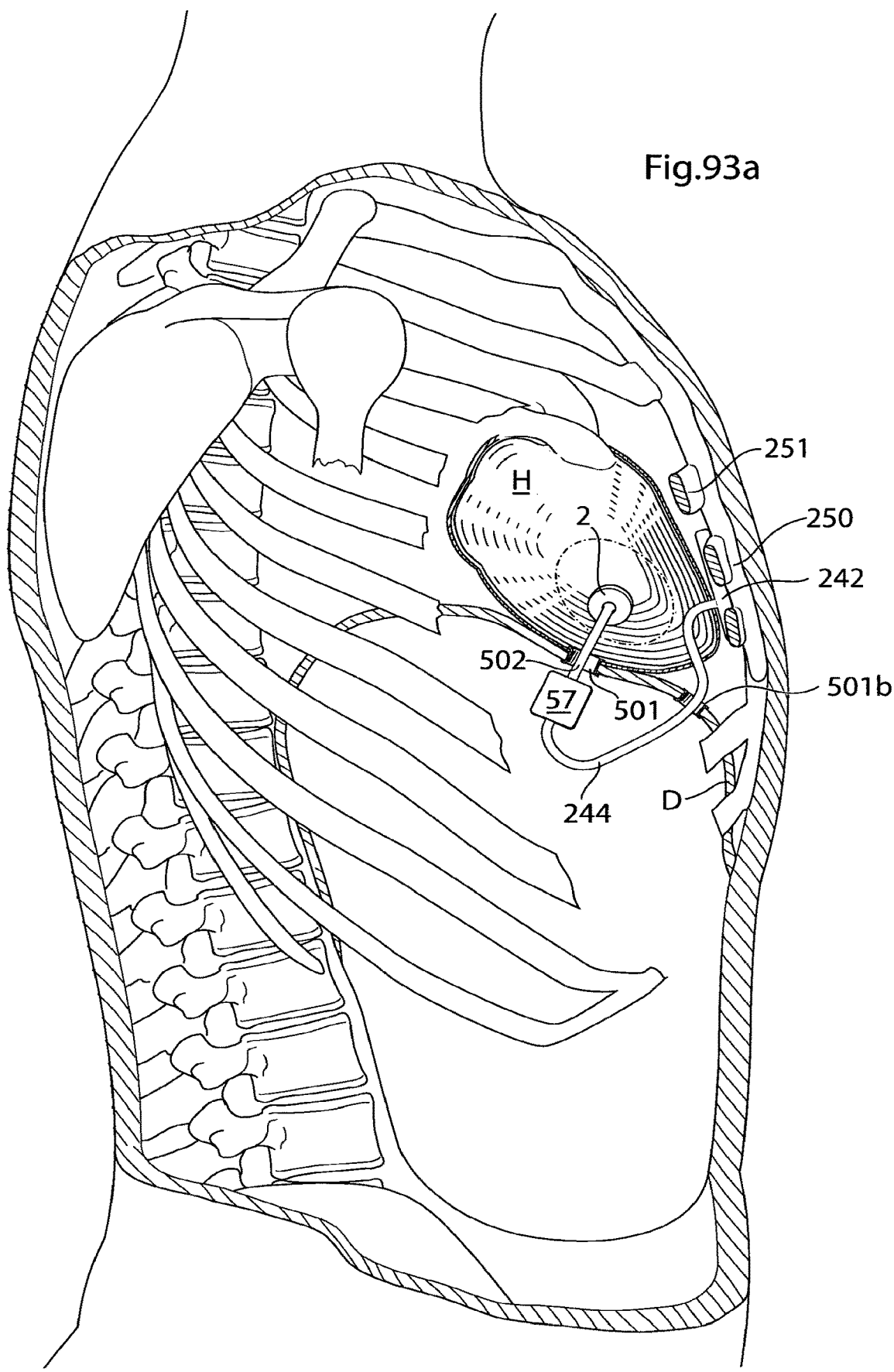

Fig.94
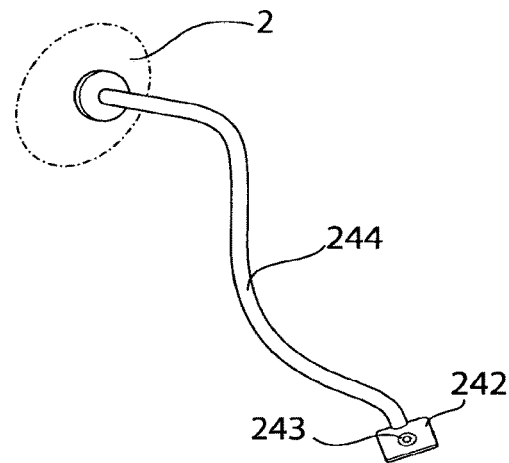
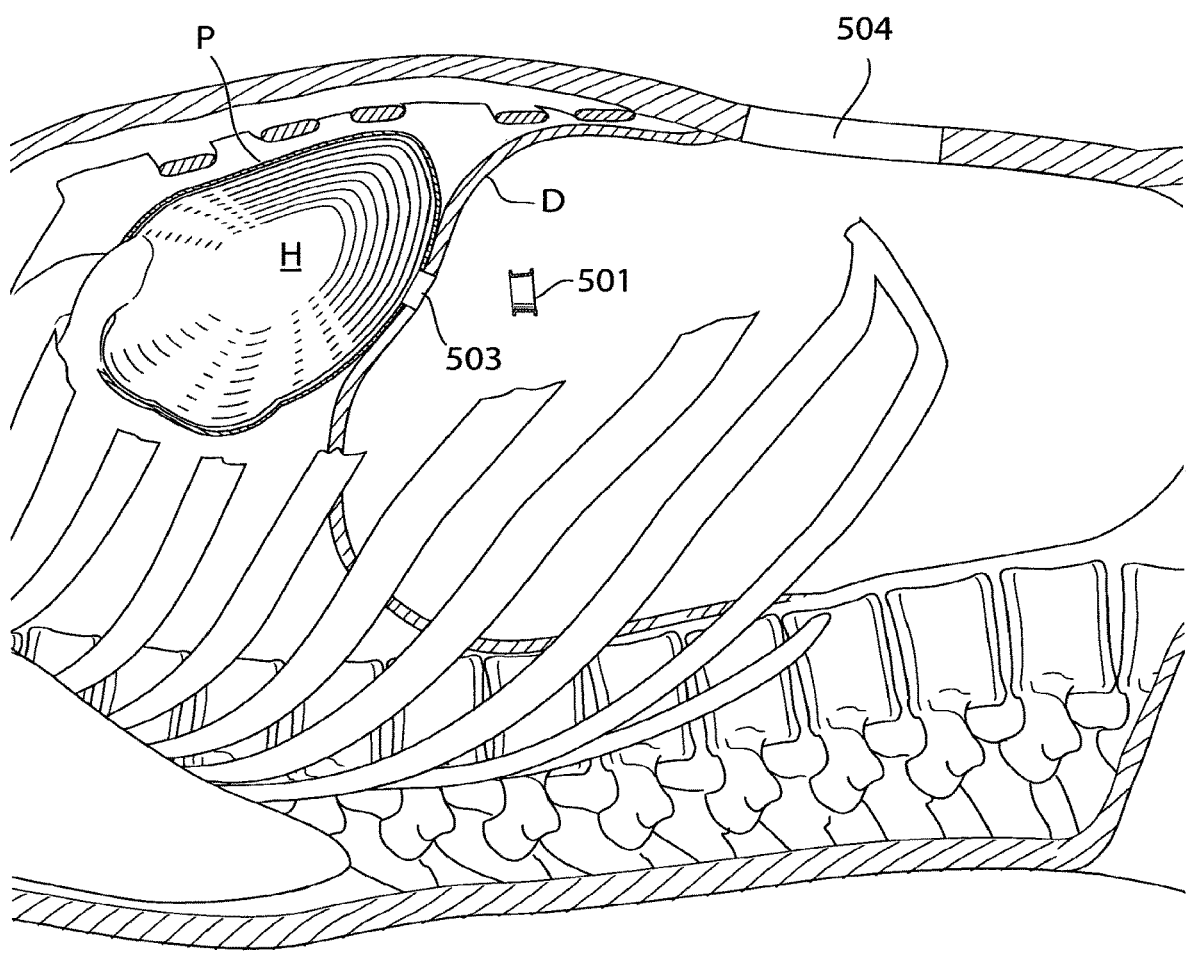

Fig.109
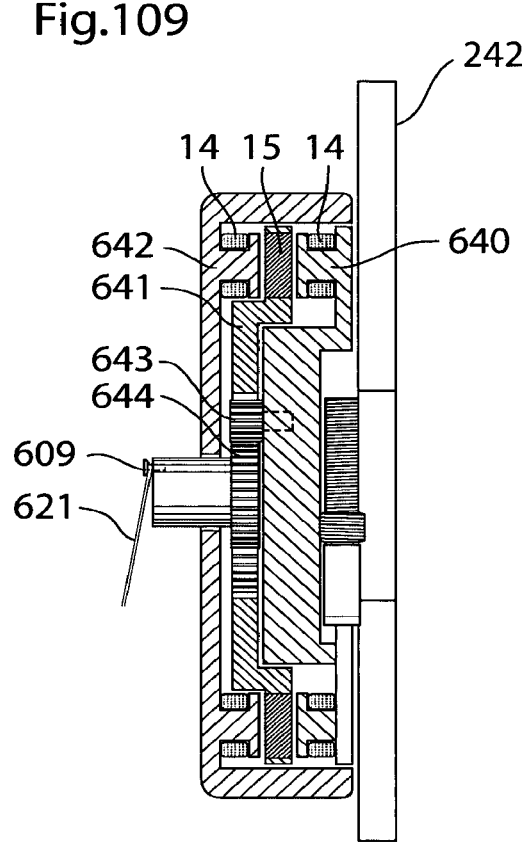
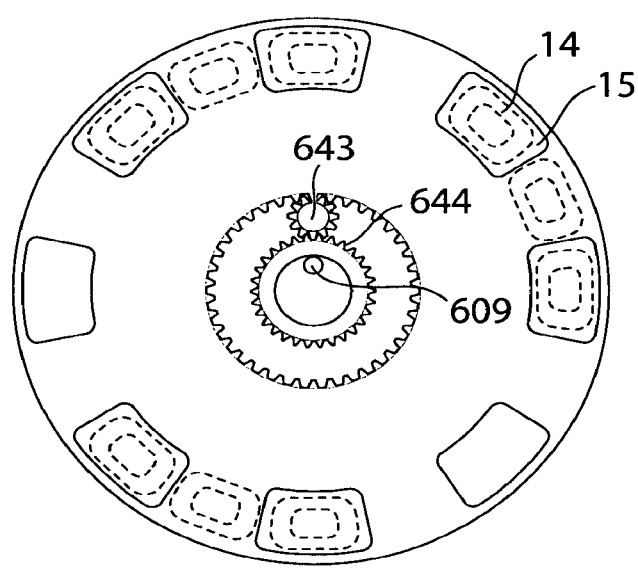

Fig.113

1
Dissecting a part of the human body comprising bone,

2
Fixating said fixation member to the bone, such that said fixation member is in contact with said connection arm.

3
Creating an opening in the thoracic diaphragm,

4
Inserting said connecting arm into the thorax through the opening in the thoracic diaphragm.

5
Placing an operating device in the abdomen of the patient.

HEART HELP DEVICE, SYSTEM AND METHOD

CROSS-REFERENCE TO RELATED APPLICATIONS

This application is a Continuation of U.S. patent application Ser. No. 14/228,253, filed 28 Mar., 2014, which is a Divisional of U.S. patent application Ser. No. 13/123,586, filed 11 Apr. 2011, now U.S. Pat. No. 8,696,745, issued on 15 Apr. 2014, which is the U.S. national phase of International Application No. PCT/SE2009/000449, filed 12 Oct. 2009, which designated the U.S. and claims priority to SE 0802141-2 filed 10 Oct. 2008; SE 0802140-4 filed 10 Oct. 2008; SE 0802139-6 filed 10 Oct. 2008; SE 0802143-8 filed 10 Oct. 2008; SE 0802144-6 filed 10 Oct. 2008 and SE 0802142-0 filed 10 Oct. 2008, and which claims the benefit of 61/202,380 filed 24 Feb. 2009; 61/202,383 filed 24 Feb. 2009; 61/202,382 filed 24 Feb. 2009; 61/202,405 filed 25 Feb. 2009; 61/202,406 filed 25 Feb. 2009; 61/202,407 filed 25 Feb. 2009; 61/202,404 filed 25 Feb. 2009 and 61/202,393 filed 25 Feb. 2009, the entire contents of each of which are hereby incorporated by reference.

BACKGROUND

A device for improving the pump function of the heart of a human patient is provided. A device for placing and fixating said heart help device in a human patient is also provided.

Cardiac compression is a known method of assisting a failing heart and has been used for many years. In its most simple form it is applied on the chest either manually or using an automatic chest compression device. The external methods are basically simple life-saving methods and can only be used to alleviate acute heart failures.

However, long lasting heart failure is ever increasing, despite the advancements in cardiology. Implantable mechanical heart compression devices could potentially provide treatment for many patients suffering from a failing heart.

On average a human heart beats 31 million times per year which gives an enormous strain in on any mechanical element that wishes to assist or replace the natural heart. Therefore it is desirable o have a heart help device with few moving parts, and where the moving parts are made of an extremely durable material. This way the device can operate for a long time without needing maintenance. Furthermore it would be preferable to have a fixation device and method for fixating said heart help device and occasionally existing motor, energizing members and control logic.

SUMMARY

A first object is to provide an implantable device for improving the pump function of the heart of a human patient by applying an external force on the heart muscle, said device comprising at least one pump device comprising: a first part having a first surface, and a second part having a second surface. Wherein said first part is displaceable in relation to the second part, said first and second surfaces abut each other, at least partially, and said second part exerts, directly or indirectly, force on an external part of said heart muscle.

According to one embodiment the implantable device furthermore comprises a second pump device. In which case it is conceivable that said first pump device is adapted to operate on the anterior side of said heart and said second pump device is adapted to operate on the posterior side of said heart.

According to one embodiment the implantable pump device further comprises a heart contacting organ in direct contact with said heart and in direct or indirect contact with at least one of: said first part and said second part.

According to one embodiment the said first surface is substantially parallel to said second surface. It is also conceivable that said heart contacting organ comprises at least one arm, in which case said arm could be replaceable.

According to one embodiment the implantable device could comprise according at least one plate, which could be substantially circular or substantially rectangular.

Drive

To operate the implantable device an operating device could be provided. The operating device could use magnetic power. According to one embodiment the operating device is the implantable device wherein the first part comprises coils and said second part comprises magnets. The device could then be operated by successive energizing of said coils which in connection with the magnets creates movements. The successive energizing could be performed from outside of the patient's body. The first part could be adapted to be rotationally or reciprocally movable in relation to said second part.

Fixation

To achieve a sturdy fixation it is conceivable that the first or second pump device of the implantable device is adapted to be fixated to the sternum, at least one rib or to at least one vertebra. The fixation could be done using a fixating member that could comprise screws, adhesive at least one plate or other mechanical fixating members.

Material

According to one embodiment the implantable device comprises ceramic or carbon material. It is also conceivable that said first and or second part comprises ceramic or carbon material. According to one embodiment the heart contacting organ comprises ceramic or carbon material.

Pressing Position

To affect the heart muscle in a good way, the implantable device could have a heart contacting organ adapted to exert an external force on the left and/or the right ventricle of said heart. It is also conceivable that the heart contacting organ is adapted to exert an external force on two different sides of the left and/or the right ventricle of said heart.

According to one embodiment the heart contacting organ could be adapted to be movable to change the position of said force exerted on said external part of said heart muscle. The heart contacting organ could be movable using a motor which could be a motor of any of the types previously discussed and could be operable form outside of the human body. It is also conceivable that the heart contacting organ is located on an arm which in turn is operable to change the position of the force exerted on the heart.

System

According to one embodiment an implantable device system for improving the pump function of the heart of a human patient is provided. The system operates by applying an external force on the heart muscle. The implantable device system comprises: at least one pump device which in turn comprises: a first part having a first surface, and a second part having a second surface. Said first part is displaceable in relation to the second part, said first and second surfaces abut each other, at least partially, and said second part exerts, directly or indirectly, force on an external part of said heart muscle. The system further comprises at least one fixating member adapted to fixate said at least one pump device to said human patient.

According to one embodiment the implantable device system comprises at least one fixating member adapted to fixate said at least one pump device to the sternum, at least one rib and/or at least one vertebra of said human patient.

According to one embodiment said at least one pump device is a adapted to compress at least one portion of a tissue wall of said heart. The pump device is further adapted to stimulate at least a portion of said tissue wall of said heart to further compress said tissue wall. The stimulation of the tissue wall of the heart could be performed using electrical stimulation. The implantable device could further comprises a control unit adapted to control said compression and/or said stimulation of said tissue wall of said heart, the control unit could be adapted to control the compression and/or stimulation from outside of the human body.

Another object is to provide a method of improving the pump function of the heart of a human patient by applying an external force on the heart muscle using the implantable device. The method comprising the steps of: displacing the first part of the pump device in relation to said second part and exerting force on an external part of said heart muscle, directly or indirectly using said second part.

According to one embodiment the device is a part of a system that may comprise a switch for manually and non-invasively controlling the device. The switch is according to one embodiment an electric switch and designed for subcutaneous implantation.

According to another embodiment the system further comprises a hydraulic device having a hydraulic reservoir, which is hydraulically connected to the device. The device could be manually regulated by pressing the hydraulic reservoir or automatically operated using a wireless remote control.

The wireless remote control system comprises, according to one embodiment, at least one external signal transmitter and an internal signal receiver implantable in the patient for receiving signals transmitted by the external signal transmitter. The system could operate using a frequency, amplitude, or phase modulated signal or a combination thereof.

According to one embodiment the wireless control signal comprises an analogue or a digital signal, or a combination of an analogue and digital signal. It is also conceivable that the signal comprises an electric or magnetic field, or a combined electric and magnetic field. According to another embodiment the wireless remote control further transmits a carrier signal for carrying the wireless control signal, said signal could comprise a digital, analogue or a combination of digital and analogue signals.

For supplying the system with energy it comprises, according to one embodiment, a wireless energy-transmission device for non-invasively energizing said device. According to said embodiment the energy-transmission device transmits energy by at least one wireless energy signal, which for example comprises a wave signal such as an ultrasound wave signal, an electromagnetic wave signal, an infrared light signal, a visible light signal, an ultra violet light signal, a laser light signal, a micro wave signal, a radio wave signal, an x-ray radiation signal and a gamma radiation signal.

It is further conceivable that the energy signal comprises an electric or magnetic field, or a combined electric and magnetic field, which can be transmitted using a carrier signal such as a digital, analogue or a combination of digital and analogue signals.

According to one embodiment the system further comprises an energy source for powering said device, which can be an implantable or external energy source or a combination thereof, in which case the internal and external energy sources can be in electric communication.

In an embodiment in which the system comprises an internal energy source, a sensor sensing a functional parameter correlated to the transfer of energy for charging the internal energy source may be provided, it is furthermore conceivable that a feedback device for sending feedback information from the inside to the outside of the patient's is provided.

According to another embodiment the system further comprises a sensor sensing a parameter such as a functional or physical parameter. Said functional parameter is, according to one embodiment, correlated to the transfer of energy for charging an internal energy source implantable in the patient. Said embodiment could furthermore comprise a feedback device for sending feedback information from inside to the outside of the patient's body and an implantable internal control unit for controlling the sensing. Above mentioned physical parameter could be one of body temperature, blood pressure, blood flow, heartbeats and breathing, and the sensor could be a pressure or motility sensor.

According to one embodiment the system could further comprise an external data communicator and an implantable internal data communicator communicating with the external data communicator, wherein the internal communicator feeds data related to said device or the patient to the external data communicator and/or the external data communicator feeds data to the internal data communicator. It is also conceivable that the system further comprises an operation device for operating said device, such as a motor or a pump, which can be electrically, hydraulically or pneumatically operated.

According to another embodiment the system has an energy-transmission device for transmitting wireless energy, wherein the wireless energy is used to directly power the operation device through for example creating kinetic energy for the operation of said device.

In embodiments where the system comprises an energy-transmission device for transmitting wireless energy, an energy-transforming device for transforming the wireless energy from a first form into a second form may be provided. Said energy-transforming device may directly power by the second form of energy. The energy could be in the form of a direct current or pulsating direct current, or a combination of a direct current and pulsating direct current, or an alternating current or a combination of a direct and alternating current, it is also conceivable that the energy is in the form of magnetic energy, kinetic energy, sound energy, chemical energy, radiant energy, electromagnetic energy, photo energy, nuclear energy or thermal energy. The system may further comprise an implantable accumulator for storing energy.

To prevent damage of the system it is conceivable that it comprises implantable electrical components including at least one voltage level guard and/or at least one constant current guard.

An operation method for surgically placing an implantable device for improving the pump function of the heart of a human patient by applying an external force on the heart muscle is further provided. The device comprises at least one heart contacting organ, comprising: a first part having a first surface, and a second part having a second surface, wherein said first part is displaceable in relation to the second part, said first and second surfaces abut each other, at least partially, and said second part exerts, directly or indirectly, force on an external part of said heart muscle. The method performed via a laparoscopic thoracic approach, the method comprising the steps of: inserting a needle or a tube like instrument into the thorax of the patient's body, using the needle or a tube like instrument to fill the thorax with gas thereby expanding the thoracic cavity, placing at least two laparoscopic trocars in the patient's body, inserting a camera through one of the laparoscopic trocars into the thorax, inserting at least one dissecting tool through one of said at least two laparoscopic trocars and dissecting an intended placement area in the area of the heart of the patient, placing the movable heart contacting organ onto the heart of the patient, placing the operating device, operating said heart contacting organ to periodically exert force on the outside of said heart, withholding force from the sternum or ribs or vertebra, connecting a source of energy for powering said implantable device for improving the pump function of the heart, operating at least one of said first and second surfaces abutting each other, at least partially, having said second part, exerting, directly or indirectly, force on an external part of said heart muscle. The exerted force could be controlled from outside the body non-invasively.

An operation method for surgically placing an implantable device for improving the pump function of the heart of a human patient by applying an external force on the heart muscle is further provided, the device comprising at least one heart contacting organ, comprising: a first part having a first surface, and a second part having a second surface, wherein the first part is displaceable in relation to the second part, said first and second surfaces abut each other, at least partially, and the second part exerts, directly or indirectly, force on an external part of said heart muscle, a method performed via thorax. The method comprises the steps of: cutting the skin and opening the thorax, dissecting an intended placement area in the area of the heart of the patient, placing the movable heart contacting organ onto the heart of the patient, placing the operating device, operating said heart contacting organ to periodically exert force on the outside of said heart, withholding force from the sternum or ribs or vertebra, connecting a source of energy for powering said implantable device for improving the pump function of the heart operating at least one of said first and second surfaces abutting each other, at least partially, having said second part, exerting, directly or indirectly, force on an external part of said heart muscle. The exerted force could be controlled from outside the body non-invasively.

According to the preferred embodiment of the invention an implantable device for improving the pump function of the heart of a human patient by applying an external force on the heart muscle, said device comprising at least one heart contacting organ, periodically exerting force onto the heart muscle following the heart contractions and adding force thereto, said implantable device adapted to have a drive unit to create kinetic movement to be used by the heart contacting organ, wherein said implantable device comprising a fixation device adapted to be mounted in a stable position to human bone allowing said drive unit and kinetic movement to get necessary contra force, wherein said drive unit further comprising a respiration movement compensator for compensating for the respiratory movement of the heart in relation to the stable bone position, wherein said drive unit is adapted to allow a movement to compensate for the respiratory movement in relation between said heart contacting organ and said bone.

Said respiration movement compensator may comprise a hydraulic, mechanical or pneumatic construction or a combination thereof, for to compensate for the respiratory movement.

The respiration movement compensator may comprise at least one of; a suspension involving a compressible cuff of air, for to compensate for the respiratory movement, a spring suspension, for to compensate for the respiratory movement and a guided movement using only frictional resistance, for to compensate for the respiratory movement.

In yet another embodiment the drive unit is adapted to be placed at least partly in the abdomen allowing the heart contacting organ to reach the heart, for creating said kinetic movement of the heart contacting organ, wherein preferable said drive unit is adapted to entering from the abdomen through the diaphragm muscle.

In another embodiment said fixation device is adapted to be mounted on the outside of the sternum, wherein said drive unit comprising an arm for passing subcutaneously from the outside of the sternum into the abdomen adapted to hold the drive unit, wherein said drive unit entering through the diaphragm muscle holding said heart contacting organ.

In another embodiment said drive unit further comprising a fibrotic tissue movement structure adapted to allow the respiratory movement of the heart in relation to the stable bone position, without interference from surrounding fibrotic tissue, when implanted in the body.

The fibrotic tissue movement structure may comprise a bellow allowing movement without stretching surrounding fibrosis, when implanted.

In yet another embodiment the heart contacting organ can change from exerting force to a first area of the heart to exerting force to a second area of the heart, after said implantable device has been implanted in said human patient, wherein said at least one heart contacting organ preferable comprises at least one hydraulic or pneumatic cushion.

In another embodiment the heart contacting organ further comprises a mechanical element, adapted to be movable to change the position of said force exerted on the heart of the human heart after said implantable device has been implanted in the human patient.

The implantable device may include a plate, and wherein said at least one hydraulic or pneumatic cushion is placed in connection to said plate, and wherein said plate enables movement of said cushion in relation to said plate to change the position of said hydraulic or pneumatic cushion and thereby change the position of said force exerted on the heart of the human patient after said implantable device has been implanted in the human patient.

The heart assistant device may be adapted to; pass through a laparoscopic trocar in the patient's body and/or pass through an opening in the diaphragm muscle from the abdominal side.

Preferable said drive unit is adapted to supply wireless or magnetic energy and said heart assistant device adapted to receive said wireless or magnetic energy to cause movements of said heart assistant device.

The heart assistant device may include an energy receiver or energy source adapted to be placed in the abdomen.

The heart assistant device preferable, comprising an electric wire adapted to connect said heart assistant device or drive unit to an internal energy source, said wire adapted to pass into the right atrium of the heart and further up in the venous blood vessel system, exiting the blood vessel system in or closer to the subcutaneous area, wherein said internal energy source is adapted to be connected to said wire via the subcutaneous area.

The heart assistant device preferable comprising:
an internal control unit,
a sensor sensing physiological electrical pulses or muscle contractions of the heart,
wherein said control unit controls said heart assistant device according to the sensed information.

The heart assistant device according to claim 10, wherein said internal energy source, comprising an internal control unit adapted to transmit energy pulses to said electrode for achieving heart muscle contractions and controlling heart contractions, wherein said control unit is adapted to coordinate the heart assistant device with the heart contractions. Method In the preferred embodiment a method of surgically placing an active heart assistant device outside a patient's heart via a laparoscopic thoracic approach, the method comprising the steps of:
inserting a needle or a tube like instrument into the thorax of the patient's body,
using the needle or a tube like instrument to fill the thorax with gas thereby expanding the thoracic cavity,
placing at least two laparoscopic trocars in the patient's body,
inserting a camera through one of the laparoscopic trocars into the thorax,
inserting at least one dissecting tool through one of said at least two laparoscopic trocars and dissecting an intended placement area of the patient's heart,
placing the heart assistant device in the placement area in the thorax as one or more pieces comprising;
placing the heart contacting organ affecting the blood stream,
placing a drive unit creating kinetic movement to be used by the heart contacting organ,
mounting a fixation device in a stable position to human bone allowing said drive unit and kinetic movement to get necessary contra force,
placing a respiration movement compensator for compensating for the respiratory movement of the heart in relation to the stable bone position, and
placing and connecting an implanted energy receiver or an internal source of energy for powering the heart assistant device to perform at least one of the following method steps;
at least partly compressing the heart and at least partly relaxing the heart assistant device to support the hearts pumping mechanism from the outside thereof.

In another embodiment an operation method for surgically placing an active heart assistant device in relation to a patient's heart, the method comprising the steps of:
cutting the patient's skin,
opening the thoracic cavity,
dissecting a placement area where to place the heart assistant device inside in relation to the heart,
placing the heart assistant device in the placement area in the thorax as one or more pieces comprising;
placing the heart contacting organ affecting the blood stream,
placing a drive unit creating kinetic movement to be used by the heart contacting organ,
mounting a fixation device in a stable position to human bone allowing said drive unit and kinetic movement to get necessary contra force,
placing a respiration movement compensator for compensating for the respiratory movement of the heart in relation to the stable bone position, and
placing and connecting an implanted energy receiver or a internal source of energy for powering the heart assistant device to perform at least one of the following method steps;
at least partly compressing the heart and at least partly relaxing the heart assistant device to support the hearts pumping mechanism from the outside thereof.

In yet another embodiment a method of surgically placing an active heart assistant device in relation to a patient's heart via a laparoscopic abdominal approach, the method comprising the steps of:
inserting a needle or a tube like instrument into the abdomen of the patient's body,
using the needle or a tube like instrument to fill the abdomen with gas thereby expanding the abdominal cavity,
placing at least two laparoscopic trocars in the patient's abdomen
inserting a camera through one of the laparoscopic trocars into the abdomen,
inserting at least one dissecting tool through one of said at least two laparoscopic trocars and
dissecting and creating an opening in the diaphragm muscle,
dissecting an intended placement area of the patient's heart through said opening,
placing the heart assistant device in the placement area in the thorax as one or more pieces comprising;
placing the heart contacting organ affecting the blood stream,
placing a drive unit creating kinetic movement to be used by the heart contacting organ,
mounting a fixation device in a stable position to human bone allowing said drive unit and kinetic movement to get necessary contra force,
placing a respiration movement compensator for compensating for the respiratory movement of the heart in relation to the stable bone position, and
placing and connecting an implanted energy receiver or an internal source of energy for powering the heart assistant device to perform at least one of the following method steps;
at least partly compressing the heart and at least partly relaxing the heart assistant device to support the hearts pumping mechanism from the outside thereof.

Alternatively an operation method for surgically placing an active heart assistant device in relation to a patient's heart, the method comprising the steps of:
cutting the patient's skin,
opening the abdominal cavity,
dissecting and creating an opening in the diaphragm muscle,
dissecting a placement area where to place the heart assistant device through said opening,
placing the heart assistant device in the placement area in the thorax as one or more pieces comprising;
placing the heart contacting organ affecting the blood stream,
placing a drive unit creating kinetic movement to be used by the heart contacting organ,
mounting a fixation device in a stable position to human bone allowing said drive unit and kinetic movement to get necessary contra force, placing a respiration movement compensator for compensating for the respiratory movement of the heart in relation to the stable bone position, and placing and connecting an implanted energy receiver or an internal source of energy for powering the heart assistant device to perform at least one of the following method steps;

at least partly compressing the heart and at least partly relaxing the heart assistant device to support the heart's pumping mechanism from the outside thereof.

The four operation methods above, wherein the step of placing the heart assistant device additionally may comprise the step of:

supplying kinetic power from said drive unit to said heart assistant device causing movement of said heart contacting organ.

The four operation methods additionally may comprise the method step of:

connecting the drive unit with an implantable energy receiver or an internal energy source for powering said drive unit.

The operation method for surgically placing a heart assistant device in a patient's heart or blood vessel combining the methods with a thoracic approach and a abdominal approach is a preferred embodiment.

The operation method, wherein the drive unit further comprising a stator and a rotor adapted to be driving at least a part of the heart assistant device with rotational energy is yet another alternative, the method further comprising the steps of:

placing said stator and rotor in the abdomen or thorax, wherein said rotor is connecting to said heart assistant device, supplying energy to said stator to rotate said rotor and thereby causing kinetic energy to be transported to said heart assistant device.

The operation method may comprise that an opening is performed from the abdomen through the thoracic diaphragm for placing the energy receiver or energy source in the abdomen.

The operation method, wherein said opening is performed in the thoracic diaphragm, is preferable positioned at the place where the pericardium is attached to the thoracic diaphragm.

In yet another method the heart assistant device or drive unit is using energy, direct or indirect, from an external energy source, supplying energy non-invasively, without any penetration through the patient's skin, for powering the heart assistant device or drive unit.

Alternatively said heart assistant device or drive unit is connected to an internal energy source via a cable, the method of placement further comprising:

dissecting and placing a wire connected to the heart assistant device or drive unit into the right atrium of the heart and further up in the venous blood vessel system, exiting the blood vessel system in or closer to the subcutaneous area, such as in the vena subclavia, vena jugularis or vena brachialis placing an internal energy source in the subcutaneous area or close thereto or in the thorax or abdomen, supplying from an external energy source energy non-invasively, without any penetration through the patient's skin, to power the internal energy source for indirect or direct power the heart assistant device or drive unit.

The operation method of placement may further comprise:

placing an electrode in the right atrium or ventricle of the heart placing the wire to the electrode via the right atrium of the heart and further up in the venous blood vessel system, exiting the blood vessel system in or closer to the subcutaneous area, such as in the vena subclavia, vena jugularis or vena brachialis, placing an internal control unit in the subcutaneous area or close thereto or in the thorax or abdomen, the method further comprising at least one of the following steps;

transmitting energy pulses from said electrode for controlling heart contractions, and coordinating the heart assistant device or drive unit.

In yet another embodiment the operation method of placement further comprising;

placing an electrode in the right atrium or ventricle of the heart placing the wire to the electrode via the right atrium of the heart and further up in the venous blood vessel system, exiting the blood vessel system in or closer to the subcutaneous area, such as in the vena subclavia, vena jugularis or vena brachialis, placing an internal control unit in the subcutaneous area or close thereto or in the thorax or abdomen, the method further comprising at least one of the following steps;

receiving sensor input relating to electrical pulses or muscle contractions of the heart, coordinating the heart assistant device or drive unit based on said sensor input.

A method of surgically placing an active heart assistant device outside a patient's heart via a laparoscopic thoracic approach is further provided by inserting a needle or a tube like instrument into the thorax of the patient's body. The needle or a tube like instrument is used to fill the thorax with gas thereby expanding the thoracic cavity. At least two laparoscopic trocars can be placed in the patient's body and a camera can be inserted into the thorax through one of the laparoscopic trocars. At least one dissecting tool can be inserted through one of said at least two laparoscopic trocars and dissecting an intended placement area of the patient's heart. A heart assistant device can be placed affecting the blood stream. An implanted energy receiver or an internal source of energy for powering the heart assistant device can be placed and connected to perform at least one of the following method step of at least partly compressing the heart and at least partly relaxing the heart assistant device to support the hearts pumping mechanism from the outside thereof.

One embodiment discloses a method for surgically placing an active heart assistant device in relation to a patient's heart further provided by cutting the patient's skin and opening the thoracic cavity. A placement area where to place the heart assistant device inside in relation to the heart is dissected and the heart assistant device is placed in the placement area in the thorax. Further an implanted energy receiver or a internal source of energy for powering the heart assistant device can be placed to perform at least one of the following method steps of at least partly compressing the heart and at least partly relaxing the heart assistant device to support the hearts pumping mechanism from the outside thereof.

Another embodiment discloses a method of surgically placing an active heart assistant device in relation to a patient's heart via a laparoscopic abdominal approach. The method can further be provided by inserting a needle or a tube like instrument into the abdomen of the patient's body and using the needle or a tube like instrument to fill the abdomen with gas thereby expanding the abdominal cavity. At least two laparoscopic trocars can be placed the patient's abdomen, through one a camera can be inserted. Further, at least one dissecting tool can be inserted through one of said at least two laparoscopic trocars. The dissecting tool can be used to dissect and create an opening in the diaphragm muscle and/or to dissect an intended placement area of the patient's heart through said opening. The heart assistant device is placed in the placement area in the thorax and an implanted energy receiver or an internal source of energy for powering the heart assistant device is placed and connected to perform at least one of the following method steps to at least partly compressing the heart and at least partly relaxing the heart assistant device to support the hearts pumping mechanism from the outside thereof.

In a further embodiment, a method for surgically placing an active heart assistant device in relation to a patient's heart can be provided by cutting the patient's skin and opening the abdominal cavity. An opening in the thoracic diaphragm is dissected and created and through said opening a placement area where to place the heart assistant device is dissected. The heart assistant device can be placed in the placement area and an implanted energy receiver or an internal source of energy for powering the heart assistant device can also be placed and connected to perform at least one of the following method steps of at least partly compressing the heart and at least partly relaxing the heart assistant device to support the hearts pumping mechanism from the outside thereof.

In a further embodiment the method also includes the step of placing the heart assistant device additionally by placing a drive unit for at least partly powering the heart assistant device with kinetic movements in the thorax or abdomen area and to supply kinetic power from said drive unit to said heart assistant device causing movement of said heart assistant device.

In another method steps can also include the connection of the drive unit with an implantable energy receiver or an internal energy source for powering said drive unit.

In another embodiment the different methods for surgically placing a heart assistant device in a patient's heart or blood vessel is combined.

Another method can also include a drive unit further comprising a stator and a rotor adapted to be driving at least a part of the heart assistant device with rotational energy. This method further comprising the steps of placing said stator and rotor in the abdomen or thorax. Said rotor is connecting to said heart assistant device to supply energy to said stator to rotate said rotor and thereby causing kinetic energy to be transported to said heart assistant device.

In one additional method an opening is performed from the abdomen through the thoracic diaphragm for placing the energy receiver or energy source in the abdomen. Said opening can be performed in the thoracic diaphragm at the section of the thoracic diaphragm in which the pericardium is fixated to the thoracic diaphragm.

In one further method the heart assistant device or drive unit is using energy, direct or indirect, from an external energy source, supplying energy non-invasively, without any penetration through the patient's skin, for powering the heart assistant device or drive unit.

In one further method said heart assistant device or drive unit is connected to an internal energy source via a cable. The method of placement further comprising the steps of dissecting and placing a wire connected to the heart assistant device or drive unit into the right atrium of the heart and further up in the venous blood vessel system, exiting the blood vessel system in or closer to the subcutaneous area, such as in the vena subclavia, vena jugularis or vena brachialis, placing an internal energy source in the subcutaneous area or close thereto or in the thorax or abdomen and to from an external energy source supply energy non-invasively, without any penetration through the patient's skin, to power the internal energy source for indirect or direct power the heart assistant device or drive unit.

One method of placement can further comprise the steps of placing an electrode in the right atrium or ventricle of the heart and to placing the wire to the electrode via the right atrium of the heart and further up in the venous blood vessel system. The blood vessel system is exited in or closer to the subcutaneous area, such as in the vena subclavia, vena jugularis or vena brachialis. An internal control unit is placed in the subcutaneous area or close thereto or in the thorax or abdomen. The method further comprising at least one of the following steps: to receive a sensor input relating to electrical pulses or muscle contractions of the heart, to transmit energy pulses from said electrode for controlling heart contractions or to coordinate the heart assistant device or drive unit.

One embodiment disclosed is a heart help device adapted to pass through a laparoscopic trocar in the patient's body.

A further embodiment is a heart help device adapted to pass through an opening in the thoracic diaphragm from the abdominal side of the thoracic diaphragm.

A further embodiment is a heart help device comprising a drive unit for at least partly powering movements of the heart help device. Said drive unit is adapted to supply wireless or magnetic energy and said heart assistant device is adapted to receive said wireless or magnetic energy to cause movements of said heart assistant device.

A further embodiment is a heart help device comprising an energy receiver or energy source, adapted to be implanted in the abdomen.

A further embodiment is a heart help device comprising an electric wire adapted to connect said heart help device or drive unit to said energy source. Said wire is adapted to pass into the right atrium of the heart and further up in the venous blood vessel system, exiting the blood vessel system in or closer to the subcutaneous area, wherein said internal energy source is adapted to be connected to said wire via the subcutaneous area.

A further embodiment is a heart help device further comprising an internal control unit and a sensor sensing physiological electrical pulses or muscle contractions of the heart. Said control unit controls said heart help device according to the sensed information.

A further embodiment is a heart help device with an energy source comprising an internal control unit adapted to transmit energy pulses to said electrode for achieving heart muscle contractions and controlling heart contractions. The control unit is being adapted to coordinate the heart assistant device with the heart contractions.

A method of surgically placing an active heart assistant device outside a patient's heart via a laparoscopic thoracic approach is further provided by inserting a needle or a tube like instrument into the thorax of the patient's body. The needle or a tube like instrument is used to fill the thorax with gas thereby expanding the thoracic cavity. At least two laparoscopic trocars can be placed in the patient's body and a camera can be inserted into the thorax through one of the laparoscopic trocars. At least one dissecting tool can be inserted through one of said at least two laparoscopic trocars and dissecting an intended placement area of the patient's heart. A heart assistant device can be placed affecting the blood stream. An implanted energy receiver or an internal source of energy for powering the heart assistant device can be placed and connected to perform at least one of the following method step of at least partly compressing the heart and at least partly relaxing the heart assistant device to support the hearts pumping mechanism from the outside thereof.

One embodiment discloses a method for surgically placing an active heart assistant device in relation to a patient's heart further provided by cutting the patient's skin and opening the thoracic cavity. A placement area where to place the heart assistant device inside in relation to the heart is dissected and the heart assistant device is placed in the placement area in the thorax. Further an implanted energy receiver or a internal source of energy for powering the heart assistant device can be placed to perform at least one of the following method steps of at least partly compressing the heart and at least partly relaxing the heart assistant device to support the hearts pumping mechanism from the outside thereof.

Another embodiment discloses a method of surgically placing an active heart assistant device in relation to a patient's heart via a laparoscopic abdominal approach. The method can further be provided by inserting a needle or a tube like instrument into the abdomen of the patient's body and using the needle or a tube like instrument to fill the abdomen with gas thereby expanding the abdominal cavity. At least two laparoscopic trocars can be placed the patient's abdomen, through one a camera can be inserted. Further, at least one dissecting tool can be inserted through one of said at least two laparoscopic trocars. The dissecting tool can be used to dissect and create an opening in the diaphragm muscle and/or to dissect an intended placement area of the patient's heart through said opening. The heart assistant device is placed in the placement area in the thorax and an implanted energy receiver or an internal source of energy for powering the heart assistant device is placed and connected to perform at least one of the following method steps to at least partly compressing the heart and at least partly relaxing the heart assistant device to support the hearts pumping mechanism from the outside thereof.

In a further embodiment, a method for surgically placing an active heart assistant device in relation to a patient's heart can be provided by cutting the patient's skin and opening the abdominal cavity. An opening in the thoracic diaphragm is dissected and created and through said opening a placement area where to place the heart assistant device is dissected. The heart assistant device can be placed in the placement area and an implanted energy receiver or an internal source of energy for powering the heart assistant device can also be placed and connected to perform at least one of the following method steps of at least partly compressing the heart and at least partly relaxing the heart assistant device to support the hearts pumping mechanism from the outside thereof.

In a further embodiment the method also includes the step of placing the heart assistant device additionally by placing a drive unit for at least partly powering the heart assistant device with kinetic movements in the thorax or abdomen area and to supply kinetic power from said drive unit to said heart assistant device causing movement of said heart assistant device.

In another method steps can also include the connection of the drive unit with an implantable energy receiver or an internal energy source for powering said drive unit.

In another embodiment the different methods for surgically placing a heart assistant device in a patient's heart or blood vessel is combined.

Another method can also include a drive unit further comprising a stator and a rotor adapted to be driving at least a part of the heart assistant device with rotational energy. This method further comprising the steps of placing said stator and rotor in the abdomen or thorax. Said rotor is connecting to said heart assistant device to supply energy to said stator to rotate said rotor and thereby causing kinetic energy to be transported to said heart assistant device.

In one additional method an opening is performed from the abdomen through the thoracic diaphragm for placing the energy receiver or energy source in the abdomen. Said opening can be performed in the thoracic diaphragm at the section of the thoracic diaphragm in which the pericardium is fixated to the thoracic diaphragm.

In one further method the heart assistant device or drive unit is using energy, direct or indirect, from an external energy source, supplying energy non-invasively, without any penetration through the patient's skin, for powering the heart assistant device or drive unit.

In one further method said heart assistant device or drive unit is connected to an internal energy source via a cable. The method of placement further comprising the steps of dissecting and placing a wire connected to the heart assistant device or drive unit into the right atrium of the heart and further up in the venous blood vessel system, exiting the blood vessel system in or closer to the subcutaneous area, such as in the vena subclavia, vena jugularis or vena brachialis, placing an internal energy source in the subcutaneous area or close thereto or in the thorax or abdomen and to from an external energy source supply energy non-invasively, without any penetration through the patient's skin, to power the internal energy source for indirect or direct power the heart assistant device or drive unit.

One method of placement can further comprise the steps of placing an electrode in the right atrium or ventricle of the heart and to placing the wire to the electrode via the right atrium of the heart and further up in the venous blood vessel system. The blood vessel system is exited in or closer to the subcutaneous area, such as in the vena subclavia, vena jugularis or vena brachialis. An internal control unit is placed in the subcutaneous area or close thereto or in the thorax or abdomen. The method further comprising at least one of the following steps: to receive a sensor input relating to electrical pulses or muscle contractions of the heart, to transmit energy pulses from said electrode for controlling heart contractions or to coordinate the heart assistant device or drive unit.

One embodiment disclosed is a heart help device adapted to pass through a laparoscopic trocar in the patient's body.

A further embodiment is a heart help device adapted to pass through an opening in the thoracic diaphragm from the abdominal side of the thoracic diaphragm.

A further embodiment is a heart help device comprising a drive unit for at least partly powering movements of the heart help device. Said drive unit is adapted to supply wireless or magnetic energy and said heart assistant device is adapted to receive said wireless or magnetic energy to cause movements of said heart assistant device.

A further embodiment is a heart help device comprising an energy receiver or energy source, adapted to be implanted in the abdomen.

A further embodiment is a heart help device comprising an electric wire adapted to connect said heart help device or drive unit to said energy source. Said wire is adapted to pass into the right atrium of the heart and further up in the venous blood vessel system, exiting the blood vessel system in or closer to the subcutaneous area, wherein said internal energy source is adapted to be connected to said wire via the subcutaneous area.

A further embodiment is a heart help device further comprising an internal control unit and a sensor sensing physiological electrical pulses or muscle contractions of the heart. Said control unit controls said heart help device according to the sensed information.

A further embodiment is a heart help device with an energy source comprising an internal control unit adapted to transmit energy pulses to said electrode for achieving heart muscle contractions and controlling heart contractions. The control unit is being adapted to coordinate the heart assistant device with the heart contractions.

Please note that all the embodiments or features of an embodiment as well as any method or step of a method could be combined in any way if such combination is not clearly contradictory. Please also note that the description in general should be seen as describing both an apparatus or device adapted to perform a method as well as this method in itself.

BRIEF DESCRIPTION OF DRAWINGS

Embodiments now described, by way of example, with reference to the accompanying drawings, in which:

FIG. 9 shows an implantable device for improving the pump function of the heart in a lateral view.

FIG. 10 shows an implantable device for improving the pump function of the heart in a lateral view.

FIG. 11 shows an implantable device for improving the pump function of the heart in a frontal view.

FIG. 23 shows an implantable device for improving the pump function of the heart in a lateral view.

FIG. 24 shows an implantable device for improving the pump function of the heart in a frontal view.

FIG. 25 shows an implantable device for improving the pump function of the heart in a lateral view.

FIG. 58 shows a lateral view of the vertebral column of a human patient, with a fixating system applied.

FIG. 59 shows a lateral view of the vertebral column of a human patient, with a fixating system applied.

FIG. 60 shows a frontal view of a part of the vertebral column of a human patient, with a fixating system applied.

FIGS. 63-77 schematically show various embodiments of the system for wirelessly powering the apparatus shown in FIG. 1.

FIGS. 82-88 show various ways of arranging hydraulic or pneumatic powering of an apparatus implanted in a patient.

FIG. 82 shows a system comprising an implanted apparatus 10 and further a separate regulation reservoir, a one way pump and an alternate valve.

FIG. 83 shows the apparatus and a fluid reservoir.

FIG. 84 shows the apparatus, a two way pump and the regulation reservoir.

FIG. 85 shows a block diagram of a reversed servo system with a first closed system controlling a second closed system.

FIG. 86A shows a flexible subcutaneous regulation reservoir connected to a bulge shaped servo reservoir by means of a conduit. FIGS. 86a-c show the regulation reservoir placed subcutaneous under the patient's skin.

FIG. 86B shows a state wherein a user, such as the patient in with the apparatus is implanted, presses the regulation reservoir so that fluid contained therein is brought to flow through the conduit and into the servo reservoir 1050, which, thanks to its bellow shape, expands longitudinally.

FIGS. 87 and 88A-88C show an alternative embodiment of hydraulic or pneumatic operation. FIG. 87 shows a block diagram comprising a first closed system controlling a second closed system.

FIG. 88A shows the first closed system where the servo reservoir contains a minimum of fluid and most fluid is found in the regulation reservoir.

FIG. 88B shows that when a user pushes the regulation reservoir, thereby displacing fluid from the regulation reservoir to the servo reservoir, the expansion of the servo reservoir will displace a larger volume of fluid from the larger adjustable reservoir to the apparatus.

FIG. 93a shows a lateral view of a patient when a heart help device is fixated to the sternum of the patient on the inside thereof, in a diaphragm penetrating way.

FIG. 94 shows a lateral view of a patient, when a diaphragm contacting part is placed.

FIG. 109 shows a magnetic operating device in section.

FIG. 113 shows a flow-chart of an operation method for fixation a heart help device.

DETAILED DESCRIPTION OF PREFERRED EMBODIMENTS

The invention will now be described in more detail in respect of preferred embodiments and in reference to the accompanying drawings. All examples herein should be seen as part of the general description and therefore possible to combine in any way in general terms. Again, individual features of the various embodiments may be combined or exchanged unless such combination or exchange is clearly contradictory to the overall function of the device.

The use of ceramic material is conceivable for entire device parts or parts exposed to wear, example of ceramic materials that can be used for this purpose is: zirconium ceramics or alumina ceramics, partially stabilised zirconia (PSZ), zirconium dioxide, titanium carbide, silicon carbide, sialons/silicon aluminium oxynitrides, boron nitride. The ceramic metarialb could further comprise a hydroxy-apatite coating.

Figure 1:
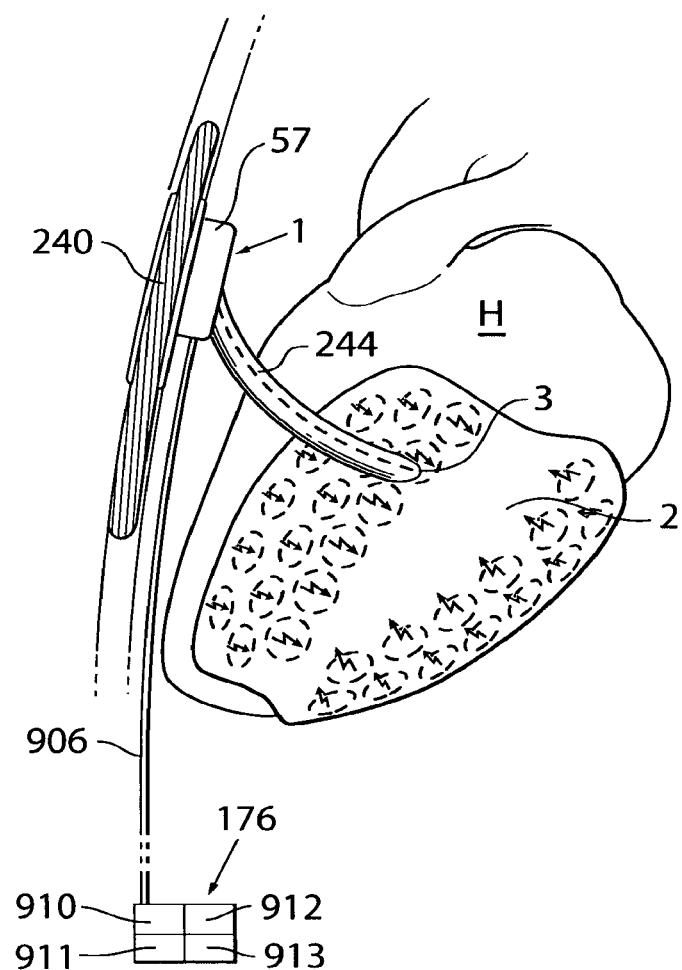
FIG. 1 shows an implantable device for improving the pump function of the heart in a lateral view.

FIG. 1 shows an implantable device 1 for improving the pump function of the heart H of a human patient by applying an external force on the heart muscle. The implantable device 1 comprises a pump device 3 which comprises an operating device 57 that creates movement of a connecting arm 244 in contact with a heart contacting organ 2. The implantable device is adapted to be fixated to a structure of the human body comprising bone 240. The operating device and occasionally occurring other elements that requires control, are controlled from a control unit 176. The control unit 176 could comprise an injection port 910 for calibrating a fluid level of a hydraulic system, a battery 911 for supplying energy to the implantable device 1, a wireless transfer system 912 for transferring energy and/or information to or from the control unit from outside of the human body and at least one sensor 913 for sensing a variable of the implantable device 1 or the patient. The control unit communicates with the pump device 3 and other elements of the implantable device 1 through a connecting member 906. However it is also conceivable that the communication could be wireless.

Figure 2:
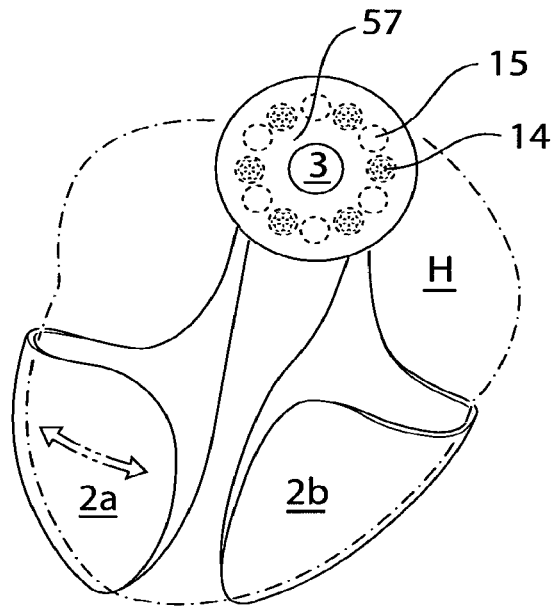
FIG. 2 shows an implantable device for improving the pump function of the heart in a frontal view.

FIG. 2 shows an implantable device 1 for improving the pump function of the heart H of a human patient by applying an external force on the heart muscle. The implantable device 1 comprises a pump device 3 which comprises an operating device 57 adapted to create a rotating movement through successive energizing coils 14 placed on a first plate 11 which is displaceable in relation to a second plate 12 comprising magnets 15. The magnetic field created between said coils 14 and said magnets 15 create a rotating movement of the second plate 12 in relation to the first plate 11. According to this embodiment the operating device is in connection with a first and second heart contacting organ 2a,b. The first heart contacting organ 2a is attached to the second plate 12 and thereby moves in relation to the second heart contacting organ 2b which is fixedly attached to the pump device 3. The second heart contacting organ 2b serves as a dolly. The first and second heart contacting organs 2a,b exerts a force on the heart H from the left and right sides of the heart H which compresses the heart H and assist the pump function of the heart H.

Figure 3:
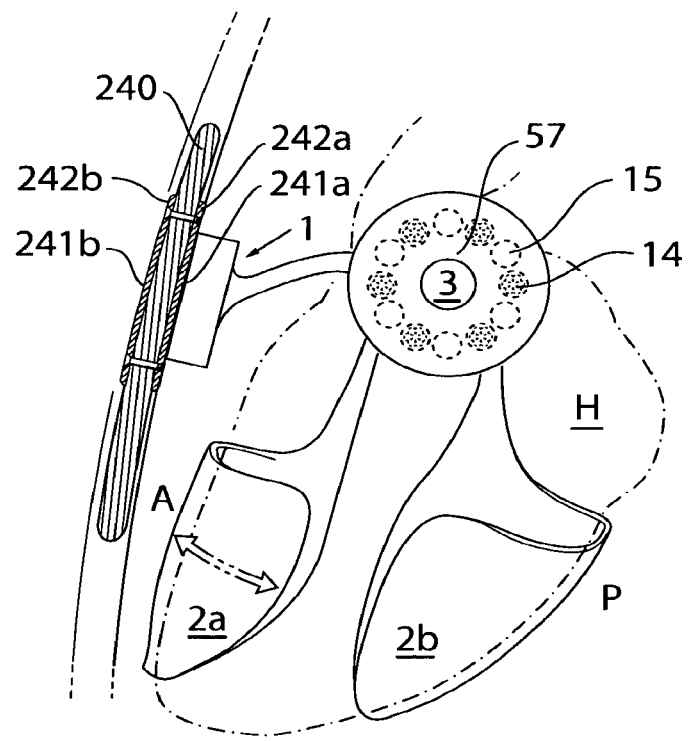
FIG. 3 shows an implantable device for improving the pump function of the heart in a lateral view.

FIG. 3 shows the implantable device 1 according to an embodiment where the pump device 3 is adapted to exert force on the heart H from the anterior A and posterior P side of the heart H. To enable the pump device 3 to exert force on the heart H from the anterior A and posterior P side of the heart H the implantable device 1 comprises a connecting arm 244 which attaches the pump device 3 to a fixating member 241a, which in turn is in contact with a first plate 242a, which is fixated to a second plate 242b of a second fixating member 241b located on the posterior side of a structure of the human body comprising bone 240. The first and second fixating members clamp the structure of the human body comprising bone 240 and thereby create the fixation of the implantable device 1. The first heart contacting organ 2a is attached to the second plate 12 and thereby moves in relation to the second heart contacting organ 2b which is fixedly attached to the pump device 3. The second heart contacting organ 2b serves as a dolly. The first and second heart contacting organs exerts a force on the heart H from the anterior A and posterior P sides of the heart H which compresses the heart H and assist the pump function of the heart H.

Figure 4:
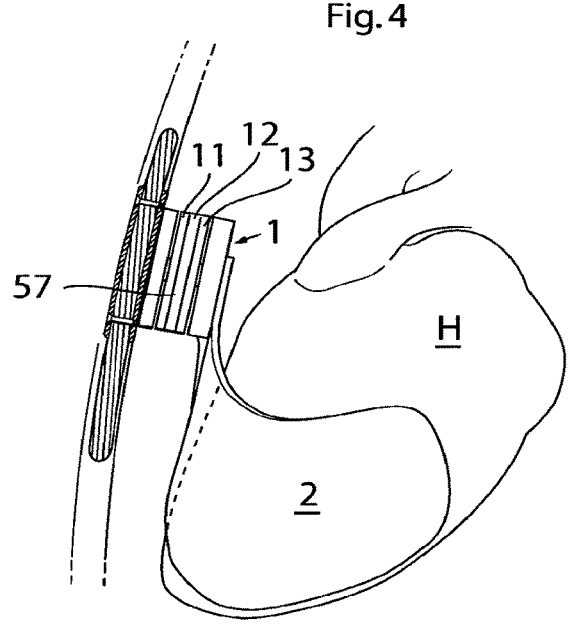
FIG. 4 shows an implantable device for improving the pump function of the heart in a lateral view.

FIG. 4 shows the implantable device 1 in a lateral view where the operating device 57 comprising a first plate 11 comprising magnets 15, a second plate 12 comprising coils and a third plate 13 comprising magnets 15. The successive energizing of the coils 14 of the second plate 12 creates rotational movement of both the first and third plate by the magnetic contact created between the coils 14 and the magnets 15. The movement is transferred to the heart contacting organ 2 which in turn exerts force on the heart H.

Figure 5:
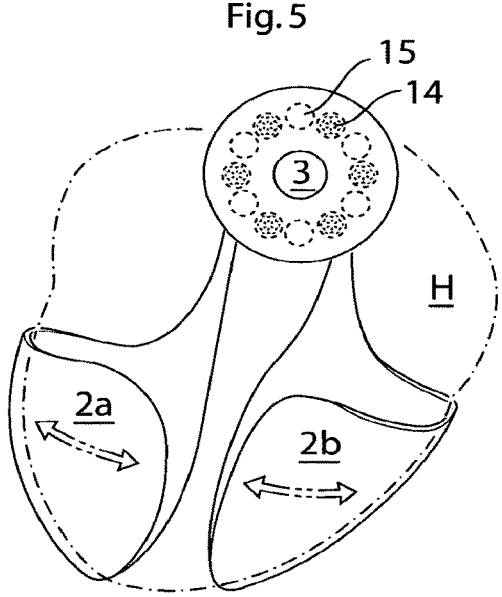
FIG. 5 shows an implantable device for improving the pump function of the heart in a frontal view.

FIG. 5 shows the implantable device 1 in a fontal view where the operating device 57 comprising a first plate 11 comprising magnets 15, a second plate 12 comprising coils and a third plate 13 comprising magnets 15. The successive energizing of the coils 14 of the second plate 12 creates rotational movement of both the first and third plate by the magnetic contact created between the coils 14 and the magnets 15. The first heart contacting organ 2a is fixated to the first plate 11, and the second heart contacting organ 2b is fixated to the third plate 13. The movement is transferred to the heart contacting organs 2a,b which in turn exerts force on the right and left sides of the heart H, which compresses the heart H and assist the pump function of the heart H.

Figure 6:
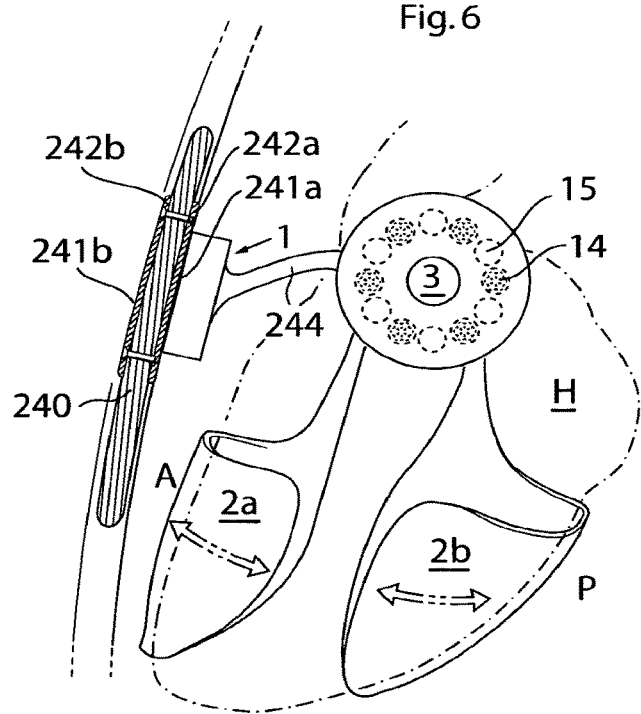
FIG. 6 shows an implantable device for improving the pump function of the heart in a lateral view.

FIG. 6 shows the implantable device 1 according to an embodiment where the pump device 3 is adapted to exert force on the heart H from the anterior A and posterior P side of the heart H. To enable the pump device 3 to exert force on the heart H from the anterior A and posterior P side of the heart H the implantable device 1 comprises a connecting arm 244 which attaches the pump device 3 to a fixating member 241a, which in turn is in contact with a first plate 242a, which is fixated to a second plate 242b of a second fixating member 241b located on the posterior side of a structure of the human body comprising bone 240. The first and second fixating members clamp the structure of the human body comprising bone 240 and thereby create the fixation of the implantable device 1. The first heart contacting organ 2a is fixated to the first plate, and the second heart contacting organ 2b is fixated to the third plate. The movement is transferred to the heart contacting organs 2a,b which in turn exerts force on the anterior A and posterior P sides of the heart H, which compresses the heart H and assist the pump function of the heart H.

Figure 7:
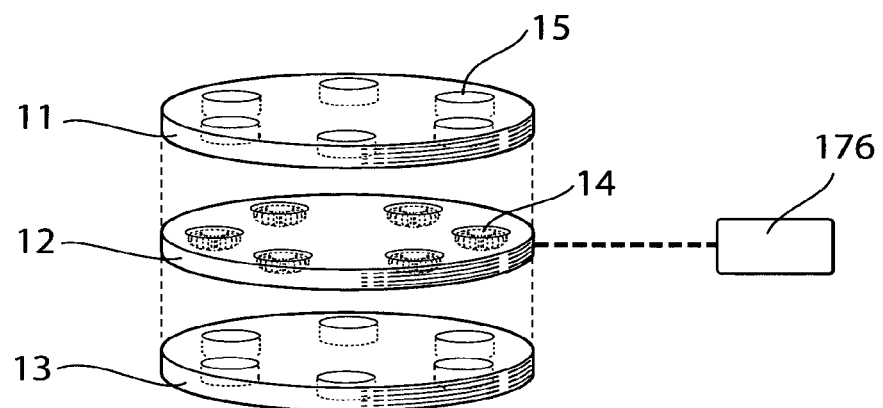
FIG. 7 shows an operating device in detail.

FIG. 7 shows the operating device 57 is further detail wherein the operating device 57 comprises a first part comprising a plate 11 with a first surface, a second part comprising a second plate 12 having a second surface and a third part comprising a third plate 13 having a third surface. The first, second and third parts are displaceable in relation to each other and adapted for rotating movement. The second plate 12 comprises coils 14 whereas the first and third plate comprises magnets 15. The coils can be successively energized, controlled from a control unit 176, which creates movement of the first and third plates by the magnetic connection between the coils 14 and magnets 15. The surfaces of the first and second plate 11,12 abut each other and is in substantially constant movement which hinders any growth of scar tissue that could interrupt the function of the operation device 57. To enable the operating device to resist the wear that constant movement of the abutting surfaces creates, the plates 11,12,13, or alternatively the surfaces, needs to be made of a highly durable material. Such a material could be a ceramic material, a carbon based material or a metallic material such as titanium or stainless steel. It is further conceivable that the plates or surfaces is made of a self lubricating material such as a fluorpolymer, alternatively the surfaces could be adapted to be lubricated by means of an implantable lubricating system. The implantable lubricating system could be adapted to lubricate the plates 11,12,13 or surfaces with a biocompatible lubricating fluid such as hyaluronic acid. A combination of mentioned materials is further conceivable. The operating device 57 is according to the embodiment in 7 adapter for rotational movement, however it is possible that the operation device is adapted for reciprocating movement.

Figure 8:
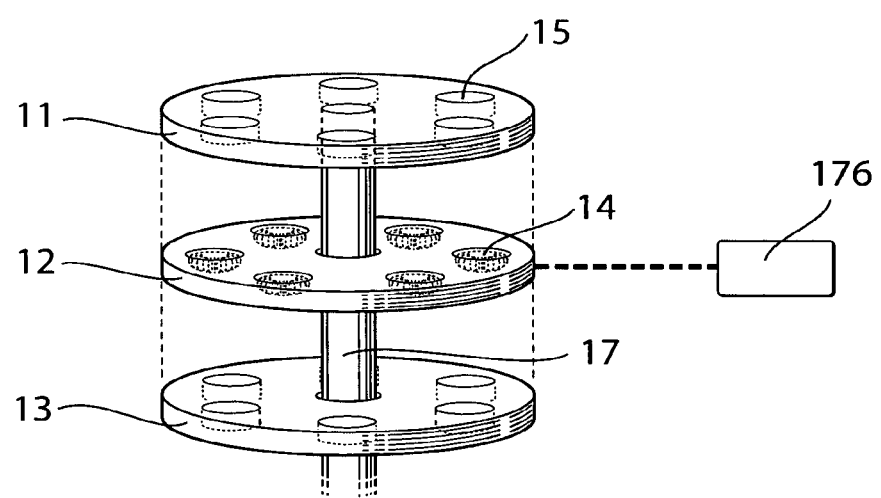
FIG. 8 shows an operating device in detail.

FIG. 8 shows the operating device 57 is further detail wherein the operating device 57 comprises a first part comprising a plate 11 with a first surface, a second part comprising a second plate 12 having a second surface and a third part comprising a third plate 13 having a third surface. The first, second and third parts are displaceable in relation to each other and adapted for rotational movement. The second plate 12 comprises coils 14 whereas the first and third plate comprises magnets 15. The coils can be successively energized, controlled from a control unit 176, which creates movement of the first and third plates by the magnetic connection between the coils 14 and magnets 15. The operating device further comprises a centre axis 17 which guides the rotational movement of the operating device 57.

FIG. 9 shows a lateral view of an embodiment where the implantable device 1 comprises a pump device 3. The pump device 3 comprises a piston 50 adapted for reciprocating movement placed in connection with an operating device 51 for operating the piston 50. The piston 50 is in turn in contact with a heart contacting organ 2 which in turn is in contact with the heart H of a human patient. The implantable device could in FIG. 9 further comprise a second pump device 53, the first and second pump devices are adapted to operate on the left and right side of the human heart H respectively, however in other embodiments the first and second pump devices 3,53 could be adapted to operate on the anterior and the posterior side of the heart H of a human patient. The implantable device 1 further comprises a first and second fixating member 241a,b adapted to fixate said implantable device 1 to a structure of the human body comprising bone 240. The fixating members comprises a first and second plate 242a,b which are fixated to each other using screws. To enable the pump device to resist the wear that constant movement of the abutting surfaces creates, affected parts or surfaces, needs to be made of a highly durable material. Such a material could be a ceramic material, a carbon based material or a metallic material such as titanium or stainless steel. It is further conceivable that parts or surfaces is made of a self lubricating material such as a fluorpolymer, alternatively the surfaces could be adapted to be lubricated by means of an implantable lubricating system. The implantable lubricating system could be adapted to lubricate parts or surfaces with a biocompatible lubricating fluid such as hyaluronic acid. A combination of mentioned materials is further conceivable. The device is in substantially constant movement which hinders any growth of scar tissue that could interrupt the function of the device.

FIG. 10 shows a lateral view of an embodiment where the implantable device 1 is adapted for exerting force on the anterior and posterior side of the human heart H. The two heart contacting organs 2a,b are adapted to exert force on the heart H through the connection with the piston 50a adapted for reciprocating movement. According to this embodiment both the heart contacting organ 2a and the heart contacting organ 2b is hinged 52 to the pump device 3 which enables both heart contacting organs 2a,b to move and exert force on the heart H. To enable the heart contacting organs 2a,b to exert force on the heart H from the anterior and posterior side of the heart H the pump device 3 is attached to a connecting arm 244 which in turn is connected to the first fixating member 241a attached to the first plate 242a which is fixated to a structure of the human body comprising bone 240 through the connection with the second plate 242b of the second fixating member 241b. The piston 50a is according to this embodiment a piston adapted to create movement in two directions, which enables two heart contacting organs 2a,b to be operable by means of only one pump device 3. It is however conceivable that the piston 50a is of a type adapted to create movement in one direction 50b in which case two pump devices 3,53 could be provided to enable two heart contacting organs 2a,b to be operable.

FIG. 11 shows a frontal view of the implantable device 1 according to the embodiment shown in FIG. 5A. The pump device 3 is here adapted to exert force on the heart H from the right and left side of the heart H through the heart contacting organs 2a,b hinged 52 to the pump device 3. The piston 50a is according to this embodiment a piston adapted to create movement in two directions, which enables two heart contacting organs 2a,b to be operable by means of only one pump device 3. It is however conceivable that the piston 50a is of a type adapted to create movement in one direction 50b in which case two pump devices 3,53 could be provided to enable two heart contacting organs 2a,b to be operable. According to this embodiment the first and second heart contacting organs 2a,b presses the heart towards each other which exerts a force on the heart H improving the pump function of the heart H.

Figure 12:
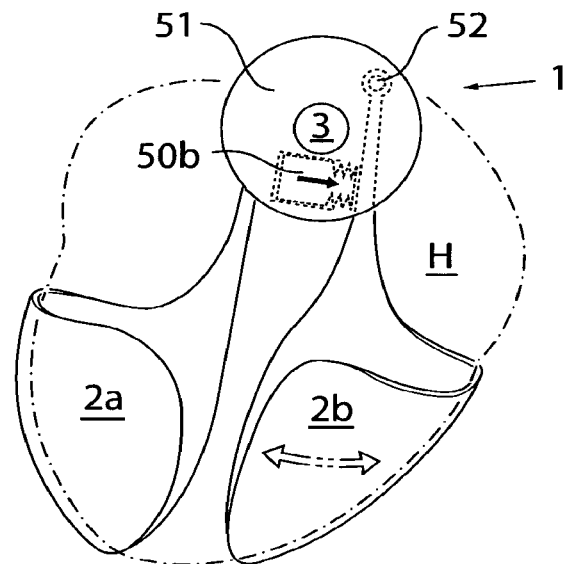
FIG. 12 shows an implantable device for improving the pump function of the heart in a frontal view.

FIG. 12 shows a frontal view of the implantable device 1 according to an embodiment where a piston 50b is adapted to create movement in one direction. According to this embodiment the second heart contacting organ 2b is hinged 52 to the implantable device 1, and the first heart contacting organ 2a is fixedly attached to the implantable device 1. According to this embodiment the second heart contacting organ 2b presses the heart towards the first heart contacting organ 2a which exerts a force on the heart H improving the pump function of the heart H.

Figure 13:
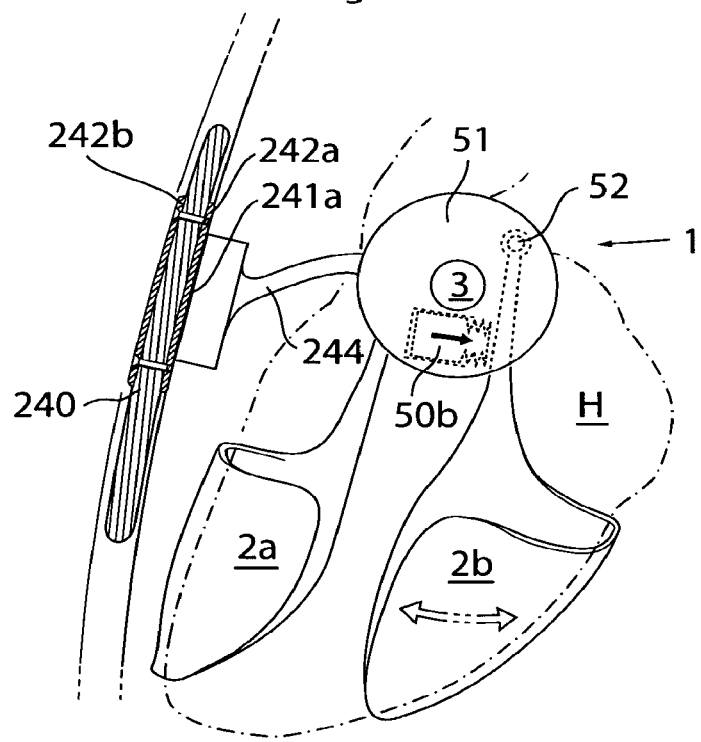
FIG. 13 shows an implantable device for improving the pump function of the heart in a lateral view.

FIG. 13 shows a lateral view of an embodiment where the implantable device 1 is adapted for exerting force on the anterior and posterior side of the human heart H. The second heart contacting organ 2b is hinged 52 to the implantable device 1, and the first heart contacting organ 2a is fixedly attached to the implantable device 1. The piston 50b is adapted to create movement in one direction and operates the second heart contacting organ 2b to exert force on the heart H from the anterior and posterior side of the heart through the second heart contacting organ 2b pressing the heart H against the first heart contacting organ 2a. To enable the exerting of force on the anterior and posterior side of the heart H the pump device 3 is attached to a connecting arm 244 which in turn is connected to the first fixating member 241a attached to the first plate 242a which is fixated to a structure of the human body comprising bone 240 through the connection with the second plate 242b of the second fixating member 241b.

Figure 14:
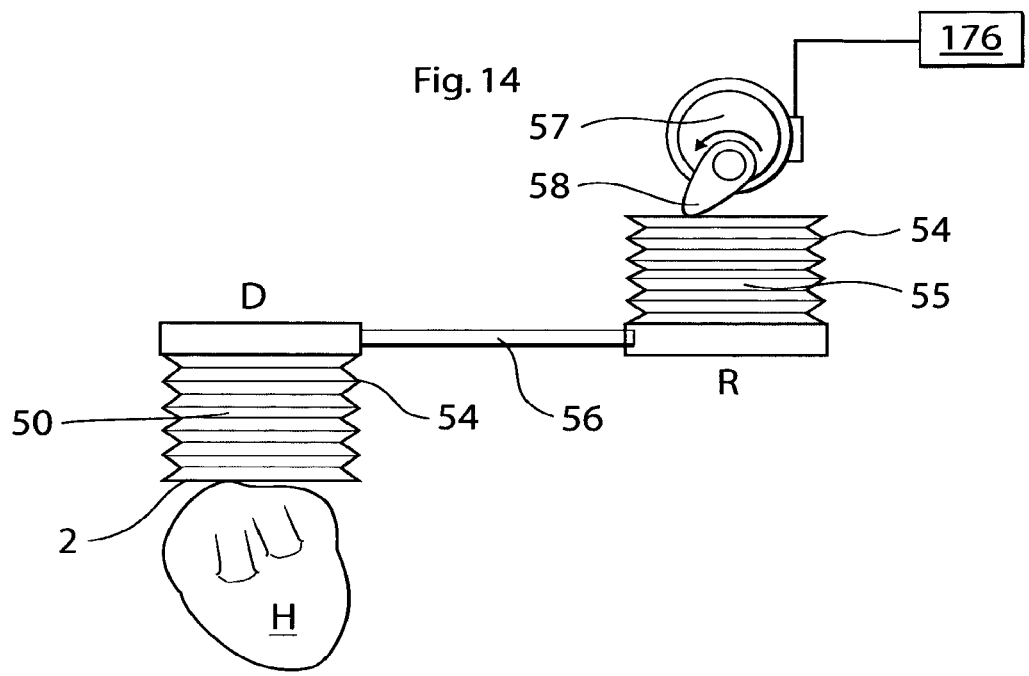
FIG. 14 shows, schematically, a system for transferring force.

FIG. 14 shows an embodiment where the implantable device 1 comprises a system for transferring of force from a remote location R to a distribution location D. The heart contacting organ 2 is a section of the force distributing piston 50 which exerts force on the heart H, the force is transferred via a force transferring system 56, which could be a hydraulic, mechanic or pneumatic force transferring system 56. The force is created using an operating device 57, in this embodiment the operating device 57 is an electric motor, however it is also conceivable that motor is a hydraulic or pneumatic motor. The force generated by the operating device is then transferred to an eccentric member 58 which creates a reciprocal movement in a second piston 55. The reciprocating movement created in the second piston 55 it then transferred through the force transferring system 56 to the first piston 50 which is placed in reciprocating movement, and in turn exerts force on the heart H through the connection with the heart contacting organ 2. The first and second pistons 50, 55 are protected by a protective layer 54 which is made of a flexible material. The protective layer 54 hinders scar tissue to form in proximity to the moving parts, which could hinder the operation of the pistons 50, 55. The operating device 57 and additional parts of the system that could require control is controlled through the control unit 176, which in turn could be adapted to be wirelessly controlled from outside of the human body.

Figure 15:
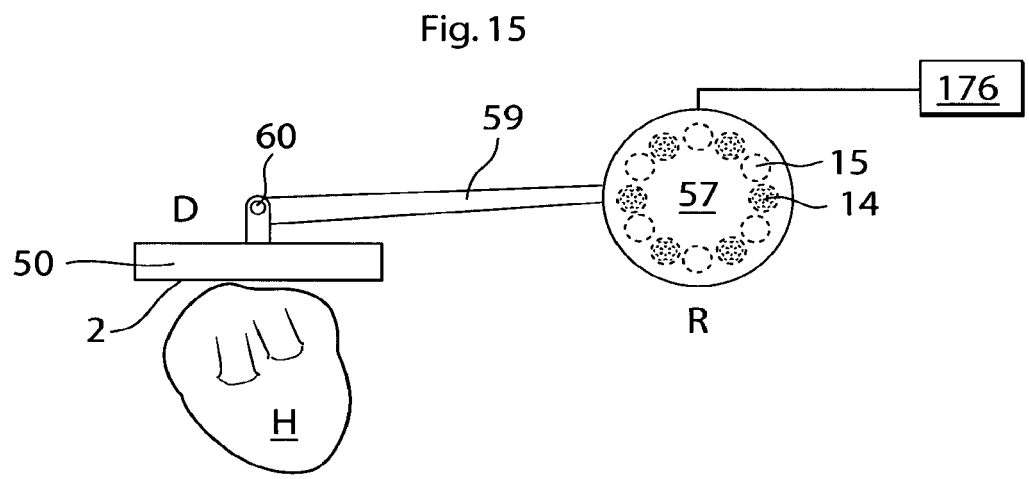
FIG. 15 shows, schematically, a system for transferring force.

FIG. 15 shows an embodiment where the operating device 57 is an operating device adapted to create a rotating movement through successive energizing coils 14 placed on a first plate which is displaceable in relation to a second plate comprising magnets 15. The magnetic field created between said coils 14 and said magnets 15 creates a rotating movement of the second plate in relation to the first plate. A mechanical force transferring member 59 is attached to the second plate and hinged 60 to the piston 50. The piston in turn comprises the heart contacting organ 2 which exerts force on the heart H through the connection with the operating device 57. A control unit 176 for controlling the operating device is also provided, which in turn could be adapted to be wirelessly controlled from outside of the human body.

Figure 16:
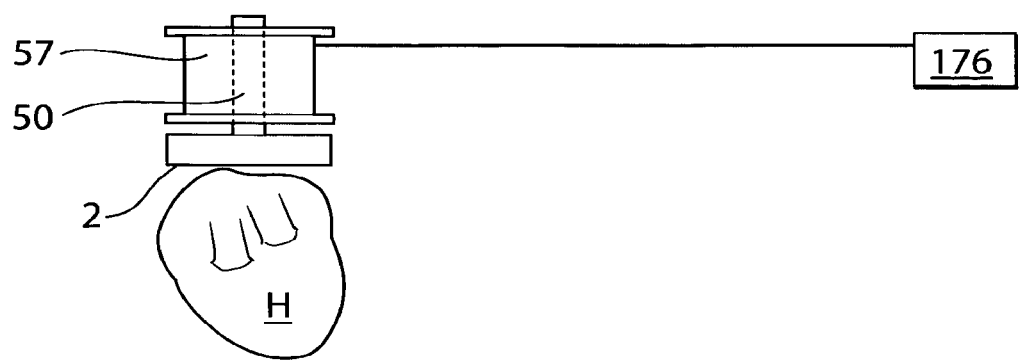
FIG. 16 shows, schematically, a system for transferring force.

FIG. 16 shows an embodiment where the operating device 57 is a solenoid adapted to create a reciprocating movement of the piston 50 in connection with the heart contacting organ 2 to exert a force on the heart H of a human patient. A control unit 176 for controlling the operating device 57 is also provided, which in turn could be adapted to be wirelessly controlled from outside of the human body.

Figure 17:
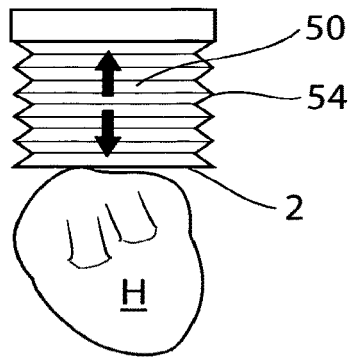
FIG. 17 shows, schematically, how force is exerted on a heart.

FIG. 17 shows, schematically, how a piston 50 housed in a protective layer 54 exerts force on the heart H of a human patient through the connection with a heart contacting organ 2. According to this embodiment the piston 50 is adapted to create reciprocating movement in two directions, the movement in the first direction is powered and the movement in the second direction could either be powered of created with a spring placed in relation to the piston 50.

Figure 18:
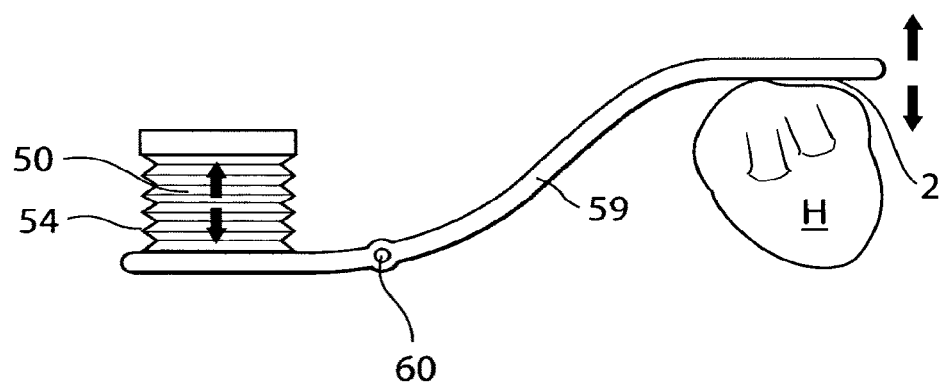
FIG. 18 shows, schematically, how force is exerted on a heart.

FIG. 18 shows, schematically, how a piston 50 housed in a protective layer 54 exerts force on the heart H of a human patient through a mechanical force transferring system 59 which comprises a hinged joint 60. The mechanical force transferring system comprises a heart contacting organ 2 which in turn exerts force on the heart of a human patient H through the connection with the mechanical force transferring system 59 and the piston 50 adapted for reciprocating movement.

Figure 19:
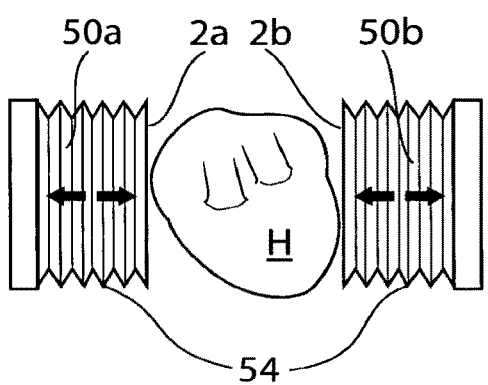
FIG. 19 shows, schematically, how force is exerted on a heart.

FIG. 19 shows, schematically, how two pistons 50a,b exerts force on the heart of a human patient H from the left and right side of the heart H. Each of the two pistons comprises a heart contacting organ 2a,b which exerts force on the heart H to compress the heart H to assist the pump function thereof. According to other embodiments the two pistons 2a,b could be adapted to be placed on the anterior and posterior side of the heart H, or be movable to enable postoperative change in the position of the force exerted on the heart H.

Figure 20:
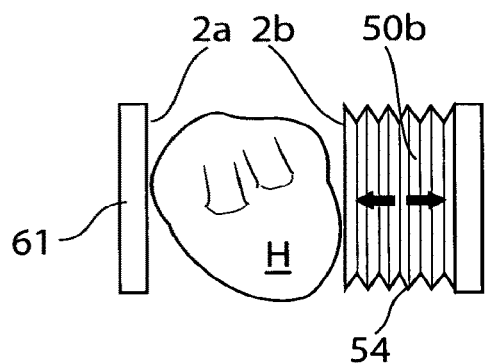
FIG. 20 shows, schematically, how force is exerted on a heart.

FIG. 20 shows, schematically, how a piston 50 exerts force on the heart of a human patient through the connection with a heart contacting organ 2a from one side of the heart H. A second heart contacting organ 2b if fixedly attached to the implantable device 1 and serves as a dolly 61 to enable the implantable device 1 to exert force on the heart H.

Figure 21:
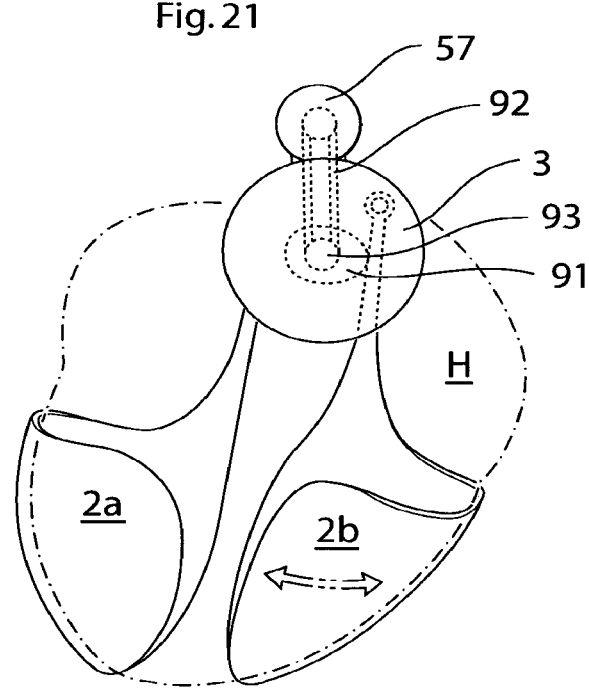
FIG. 21 shows an implantable device for improving the pump function of the heart in a frontal view.

FIG. 21 shows a frontal view of an implantable device 1 for improving the pump function of the heart of a human patient according to an embodiment wherein the implantable device comprises a pump device 3 comprises a rotating member 93 having a rotating centre. A driving member 91 is attached to the rotating member 93 and adapted to perform an eccentric movement in relation to the rotating center of said rotating member 93. The driving member 91 is in contact with a heart contacting organ 2a,b which in turn is adapted to exert force on the heart H of a human patient. The pump device further comprises an operating device 57 for operating the driving member 91. The operating device is in connection with the rotating member through a force transferring member 92 which for example could be a band, cord or chain. The operating device 57 could be an electric, hydraulic or pneumatic motor, and could be adapted to be controlled from outside of the human body. To enable the pump device to resist the wear that constant movement of the abutting surfaces creates, affected parts or surfaces, needs to be made of a highly durable material. Such a material could be a ceramic material, a carbon based material or a metallic material such as titanium or stainless steel. It is further conceivable that parts or surfaces is made of a self lubricating material such as a fluorpolymer, alternatively the surfaces could be adapted to be lubricated by means of an implantable lubricating system. The implantable lubricating system could be adapted to lubricate parts or surfaces with a biocompatible lubricating fluid such as hyaluronic acid. A combination of mentioned materials is further conceivable. The device is in substantially constant movement which hinders any growth of scar tissue that could interrupt the function of the device.

Figure 22:
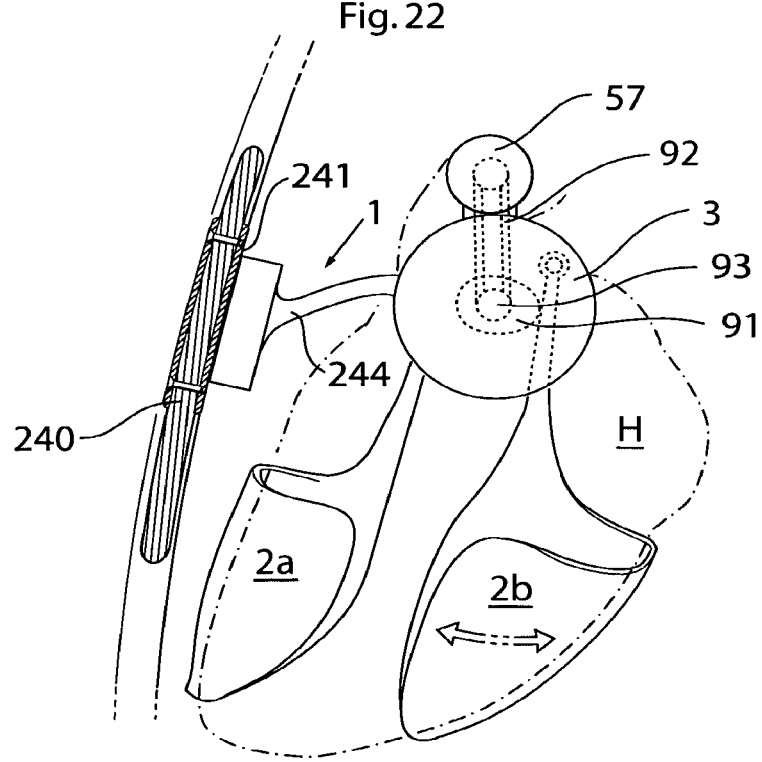
FIG. 22 shows an implantable device for improving the pump function of the heart in a lateral view.

FIG. 22 shows a lateral view of an implantable device 1 for improving the pump function of the heart of a human patient according to an embodiment wherein the implantable device comprises a pump device 3 comprises a rotating member 93 having a rotating centre. A driving member 91 is attached to the rotating member 93 and adapted to perform an eccentric movement in relation to the rotating center of said rotating member 93. The driving member 91 is in contact with a heart contacting organ 2a,b which in turn is adapted to exert force on the heart H of a human patient. The pump device further comprises an operating device 57 for operating the driving member 91. The operating device is in connection with the rotating member through a force transferring member 92 which for example could be a band, cord or chain. The operating device 57 could be an electric, hydraulic or pneumatic motor, and could be adapted to be controlled from outside of the human body. To enable the exerting of force on the anterior and posterior side of the heart H the pump device 3 is attached to a connecting arm 244 which in turn is connected to a fixating member 241 which is fixated to a structure of the human body comprising bone 240. According to this embodiment the first heart contacting organ is fixedly attached to the pump device 3 and serves as a dolly, whereas the second heart contacting organ is hinged to exert the force on the heart H.

FIG. 23 shows a lateral view of the implantable device 1 described in FIG. 21 where the pump device is adapted to exert force on the heart H from the right and left side of the heart H. The driving member 91 is in contact with an operating device 57.

FIG. 24 shows a frontal view of the pump device 3 wherein both the first heart contacting organ 2a and the second heart contacting organ 2b are hinged to the pump device 3 which enables the heart contacting organs 2a,b to exert force on the heart H, assisting the pump function thereof, from the right and left side of the heart H. The driving member 91 is according to this embodiment designed to operate two heart contacting organs 2a,b through the connection with the operating device 57.

FIG. 25 shows a lateral view of the pump device 3 wherein both the first heart contacting organ 2a and the second heart contacting organ 2b are hinged to the pump device 3, which enables the heart contacting organs 2a,b to exert force on the heart H, assisting the pump function thereof, from the anterior and posterior side the heart H. The driving member 91 is according to this embodiment designed to operate two heart contacting organs 2a,b through the connection with the operating device 57. To enable the exerting of force on the anterior and posterior side of the heart H the pump device 3 is attached to a connecting arm 244 which in turn is connected to a fixating member 241 which is fixated to a structure of the human body comprising bone 240.

Figure 26:
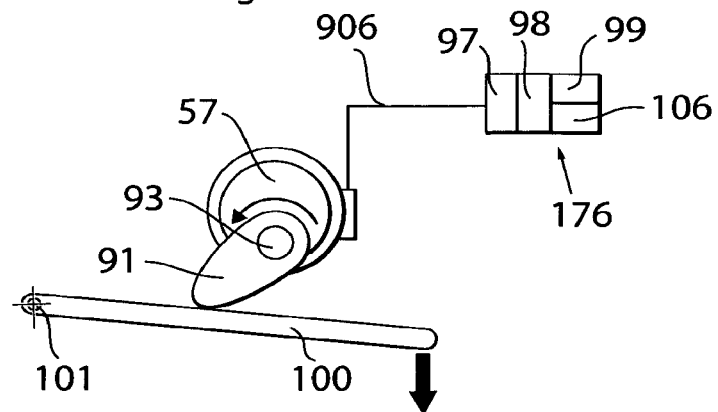
FIG. 26 shows, schematically, a system for transferring force.

FIG. 26 shows, schematically, an embodiment of a pump device according to any of the embodiments. An operating device 57 operates a rotating member 93 having a rotating centre which is attached to a driving member 91 adapted to create an eccentric movement. The driving member is in contact with a pivot 100 which is hinged 101. The pivot could serve as a mechanical transmitter of force, or as a heart contacting organ 2 adapter to exert force on the heart H of a human patient. The operating device is controlled using a control unit 176 connected to the operating device through a connecting member 906. The operating device could be an electric, magnetic, hydraulic or pneumatic motor. In any embodiment where hydraulics is used an injection port 97 could be provided to enable the calibration of fluid in the hydraulic system. The control unit 176 could further comprise at least one sensor 98 for sensing a variable of the device, or the patient. Furthermore the control unit 176 could comprise a wireless transfer unit 99 for transferring of wireless energy and/or information. At least one battery 106 could also be provided in the control unit.

Figure 27:
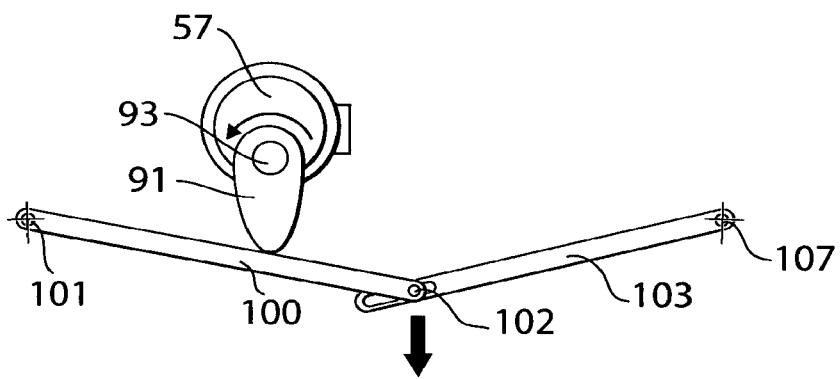
FIG. 27 shows, schematically, a system for transferring force.

FIG. 27 shows, schematically, an embodiment of a pump device according to any of the embodiments. An operating device 57 operates a rotating member 93 having a rotating centre which is attached to a driving member 91 adapted to create an eccentric movement. The driving member is in contact with a pivot 100 which is hinged 101 in one end, the other end is in contact with another pivot 103 which is hinged in its other end 107. The pivot system that the first and second pivot 100,103 could be used as a mechanical transmitter of force, or said first or second pivot could comprise a heart contacting organ 2 adapted to exert force on the heart H.

Figure 28:
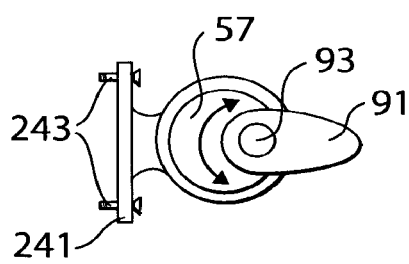
FIG. 28 shows, schematically, an operating device and a fixating member.

FIG. 28 shows, schematically, an embodiment of a pump device 3, where the pump device 3 comprises a fixating member 241 which is adapted to fixate the pump device 3 to a structure of the human body comprising bone 240. The fixating member is adapted to fixate the pump device 3 to a structure of the human body comprising bone 240 using screws 243.

Figure 29:
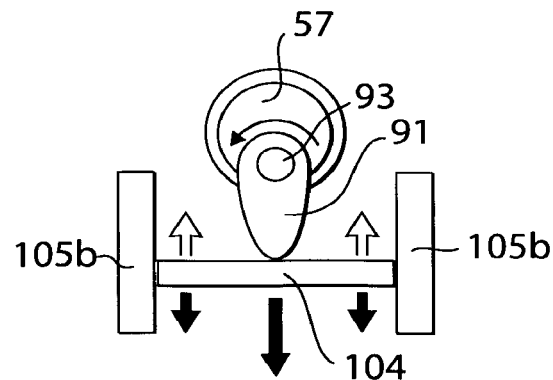
FIG. 29 shows, schematically, a system for transferring force.

FIG. 29 shows, schematically, an embodiment of a pump device according to any of the embodiments. An operating device 57 operates a rotating member 93 having a rotating centre which is attached to a driving member 91 adapted to create an eccentric movement. The driving member is in contact with a reciprocating member 104 which is guided by two guiding members 105a,b. The reciprocating member 104 could be used as a mechanical transmitter of force, or comprising a heart contacting organ 2 adapted to exert force on the heart H.

Figure 30:
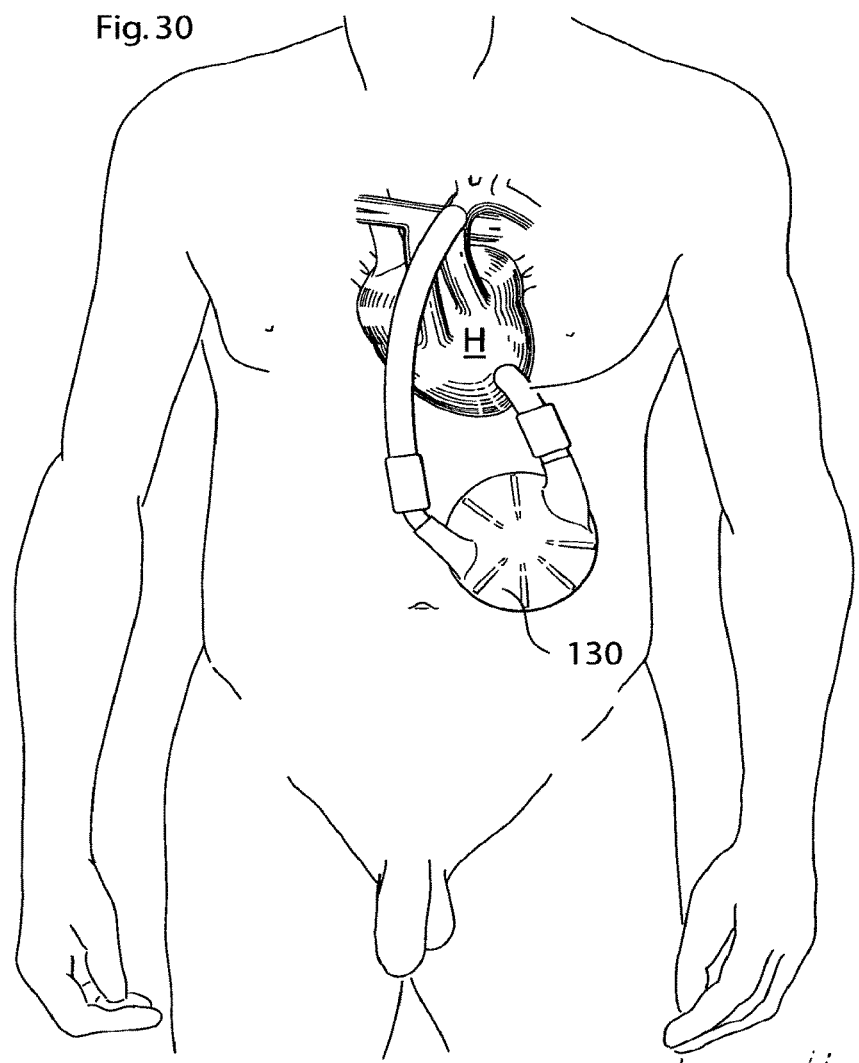
FIG. 30 shows a frontal view of a human patient with an LVAD.

FIG. 30 shows a frontal view of a human patient according to an embodiment where the implanted device 1 is an LVAD 130 (Left Ventricular Assist Device). The LVAD can be fixated to a structure of the human body comprising bone 240 according to any of the embodiments described.

Figure 31:
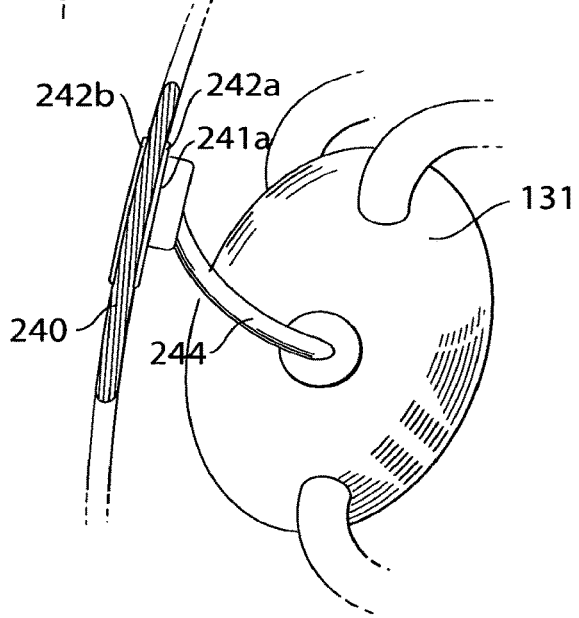
FIG. 31 shows an implanted artificial heart device in a lateral view.

FIG. 31 shows a frontal view of a human patient according to an embodiment where the implanted device 1 is an artificial heart device 131. The artificial heart device 131 can be fixated to a structure of the human body comprising bone 240 according to any of the embodiments described.

Figure 32:
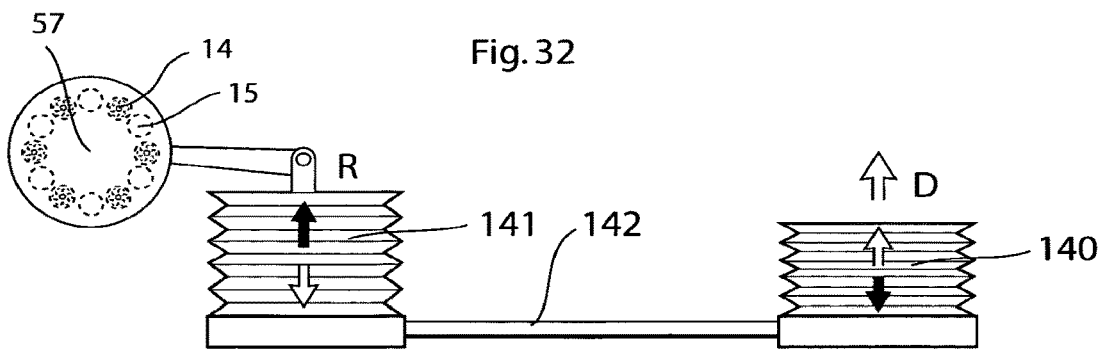
FIG. 32 shows, schematically, a system for transferring force.

FIG. 32 schematically shows a closed pneumatic or hydraulic implantable system for transferring force from a remote location R to a distribution location D. The system comprises a first reservoir in the form of a first bellows 141 in contact with an operating device 57, which in this embodiment is an operating device comprising coils 14 and magnets 15, which is described in further detail previously. The volume of the first bellows 141 is affected by the contact with the operating device 57 which causes a fluid to be transferred in the fluid connection 142, which in turn affects the second bellows 140 on the distribution location. The second bellows could be used as a mechanical force transmitter or could be provided with a heart contacting organ 2 for exerting force on the heart of a human patient H. The implantable system is adapted to allow free flow of fluid between said first bellows 141 and said second bellows.

Figure 33:
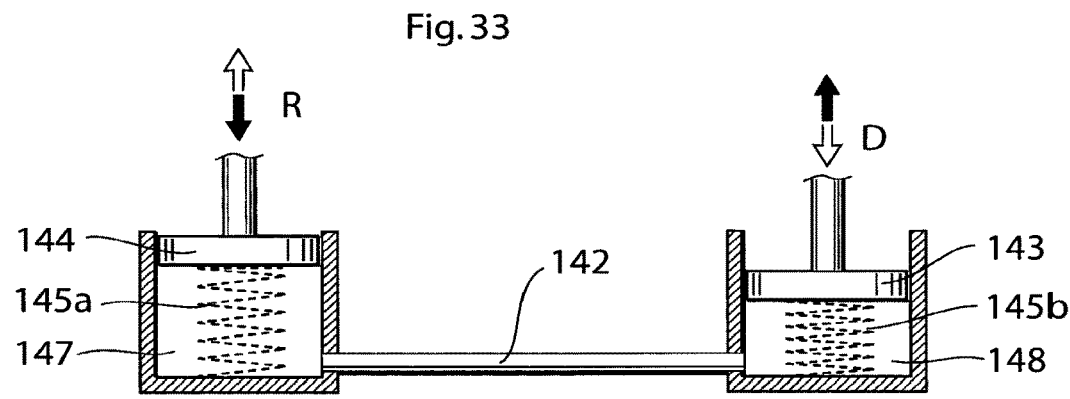
FIG. 33 shows, schematically, a system for transferring force.

FIG. 33 schematically shows a closed pneumatic or hydraulic implantable system for transferring force from a remote location R to a distribution location D. The system comprises a first reservoir in the form of a first piston 144. The volume in the cylinder 147 of the first piston 144 is affected by the contact with an operating device which causes a fluid to be transferred in the fluid connection 142, which in turn affects the second piston 143 on the distribution location, through the change of the fluid volume in the second cylinder 148. The second piston 143 could be used as a mechanical force transmitter or could be provided with a heart contacting organ 2 for exerting force on the heart of a human patient H. The implantable system is adapted to allow free flow of fluid between said first bellows 141 and said second bellows. The system could be adapted to operate using pressurized fluid in one direction and vacuum in the other direction, or pressurized fluid in both directions. It is also conceivable that the first and second pistons 143,144 operates by means of a spring 145*a,b* in one direction.

Figure 34:
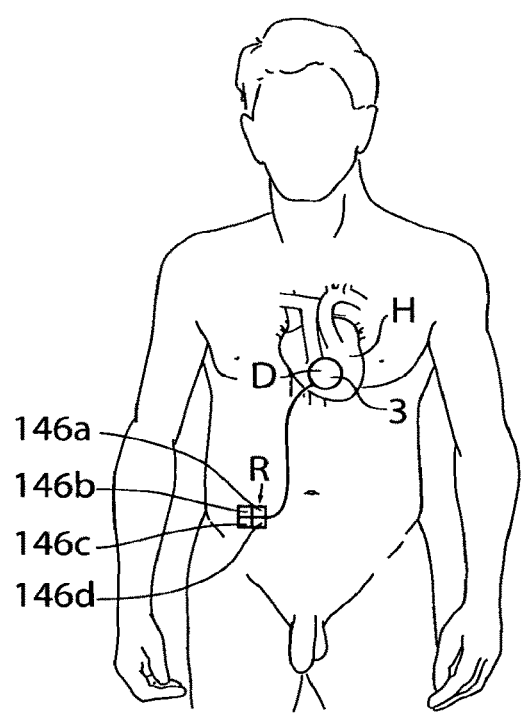
FIG. 34 shows a frontal view of a human patient with an implanted system for transferring force.

FIG. 34 shows a frontal view of a patient where the remote location R of the implantable system for transferring force from a remote location R to a distribution location D, is located in the abdominal region and the distribution location is located in connection with the heart H. The remote location comprises a control unit which in turn could comprise an operating device 146*a*, an injection port 146*b*, a battery 146*c* and at least one sensor 146*d* for sensing a variable of the implantable system or the patient.

Figure 35:
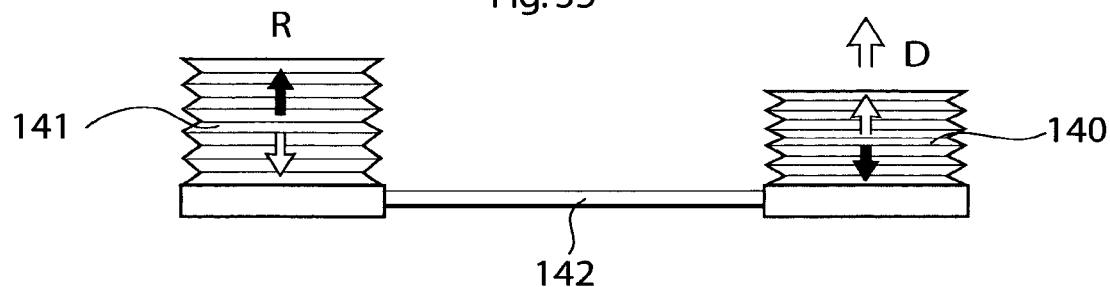
FIG. 35 shows, schematically, a system for transferring force.

FIG. 35 schematically shows a closed pneumatic or hydraulic implantable system for transferring force from a remote location R to a distribution location D. The system comprises a first reservoir in the form of a first bellows 141 an a second reservoir in form of a second bellows 140. The first and second bellows are connected through a fluid connection 142. The fluid connection is adapted to always allow free flow of fluid between the first and second reservoir.

Figure 36:
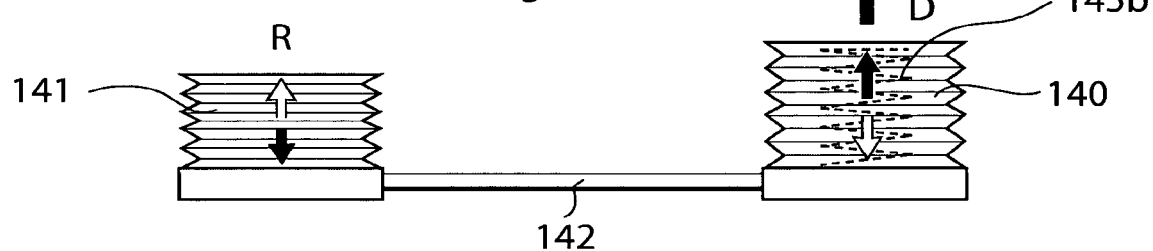
FIG. 36 shows, schematically, a system for transferring force.

FIG. 36 schematically shows a closed pneumatic or hydraulic implantable system for transferring force from a remote location R to a distribution location D. The system comprises a first reservoir in the form of a first bellows 141 an a second reservoir in form of a second bellows 140. The first and second bellows are connected through a fluid connection 142. The fluid connection is adapted to always allow free flow of fluid between the first and second reservoir. The system is operated using pressurized fluid in one direction and spring force from a spring 145*b* in the second bellows in opposite direction.

Figure 37:
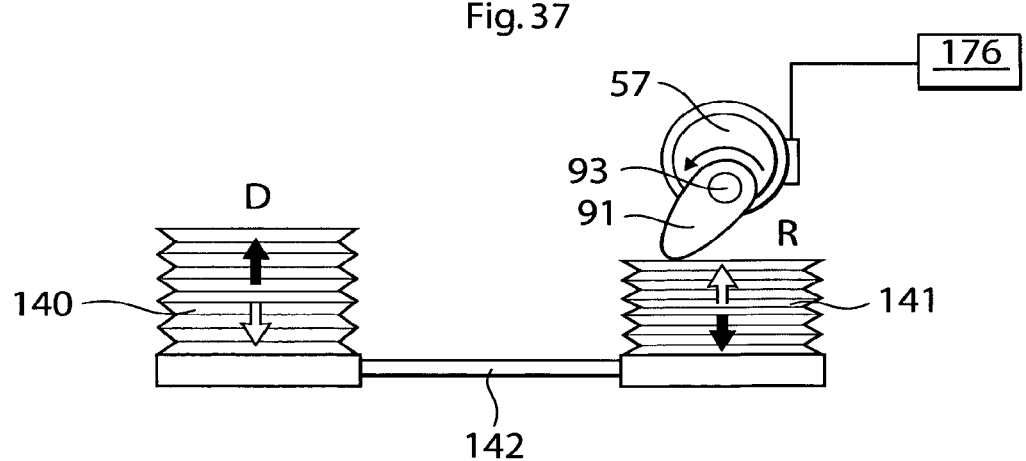
FIG. 37 shows, schematically, a system for transferring force.

FIG. 37 schematically shows a closed pneumatic or hydraulic implantable system for transferring force from a remote location R to a distribution location D. The system comprises a first reservoir in the form of a first bellows 141 in contact with an operating device 57, which in this embodiment is an operating device comprising a rotating member 93 having a rotating centre which is attached to a driving member 93 adapted to create an eccentric movement affecting the first bellows. The volume of the first bellows 141 is affected by the contact with the operating device 57 which causes a fluid to be transferred in the fluid connection 142, which in turn affects the second bellows 140 on the distribution location. The second bellows could be used as a mechanical force transmitter or could be provided with a heart contacting organ 2 for exerting force on the heart of a human patient H. The implantable system is adapted to allow free flow of fluid between said first bellows 141 and said second bellows 140.

A heart contacting organ 2, for example displayed in the embodiments above, could be adapted to change the position of the force exerted on the heart H of a human patient. This could be done by adjusting the position of the heart contacting organ 2 in relation to a fixating member 241 that fixates an implantable device 1 comprising the heart contacting organ 2 to a structure of the human body comprising bone 240. The adjustment could be performed by moving a connecting arm which is fixated to the fixating member 241 and the heart contacting organ 2. The object of moving the heart contacting organ 2 could be to increase the blood flow to area on which the heart contacting organ 2 exerts force. It could also be to improve the positioning of the heart contacting organ 2 such that the ability of the implantable device 1 to assist the pump function of the heart H. It could further be to relive the patient of any discomfort that the implantable device 1 might cause him/her.

Figure 38:
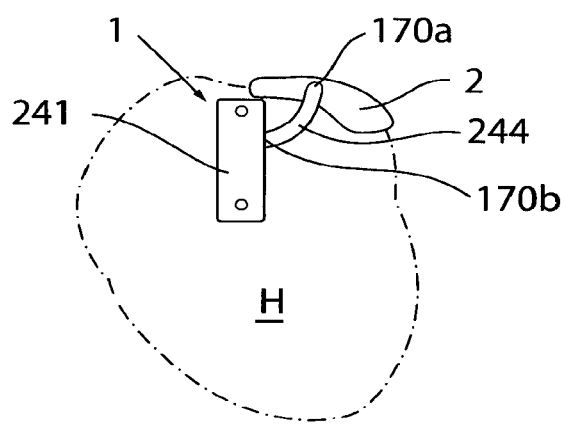
FIG. 38 shows a heart contacting organ in a first position.

FIG. 38 shows an embodiment in which the heart contacting organ 2 is attached to a connecting arm 244 in connection with the heart contacting organ 2 and the fixating member 241. The connecting arm 244 is hinged 170*a,b* to both the heart contacting organ 2 and the fixating member 241. However it is conceivable that the connecting arm 244 is hinged to one of the points 170*a* and 170*b* and fixedly attached to the other 170*a,b* respectively. The connecting arm 244 could be adapted to be operable either manually or powered. The connecting arm could be operable by means of an operation device 172 which could be an electric, a mechanical, a hydraulic or a pneumatic operating device 172. The operating device 172 could be placed in connection with the fixating member 241 and could be adapter to be remotely controlled from outside of the human body using a remote control. It is also conceivable that the connecting arm could be manually adjusted during a surgical or laparoscopic procedure in which case an adjusting member (not shown) could be provided to the implantable device 1. The adjusting member could be one that is adjustable by means of a surgical tool used in the surgical or laparoscopic procedure.

Figure 39:
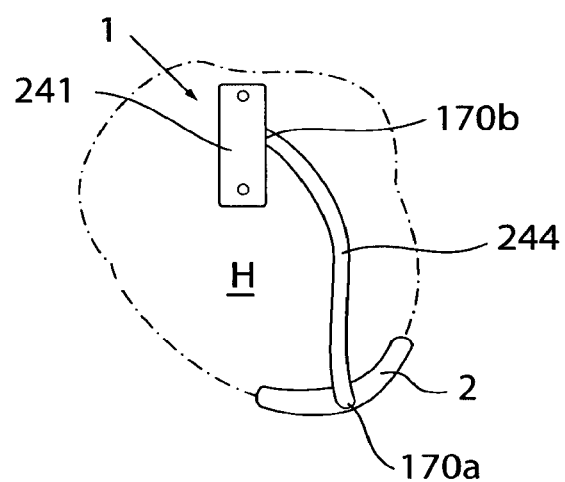
FIG. 39 shows a heart contacting organ in a second position.

FIG. 39 shows an embodiment where the heart contacting organ 2 has been moved from the position in which it is placed in FIG. 38. The position of the force exerted on the heart H is thereby moved.

An alternative approach to moving the position of the force exerted on the heart is to move elements on the heart contacting organ 2. The elements could be pistons 173 and/or cushions 171 which could be electrically, mechanically, hydraulically or pneumatically operated. The pistons 173 and/or cushions 171 could be adapter to be remotely controlled from outside of the human body using a remote control. It is also conceivable that the pistons 173 and/or cushions 171 could be manually adjusted during a surgical or laparoscopic procedure. The heart contacting organ could comprise cushions 171 exclusively, pistons 173 exclusively or a mixture thereof.

Figure 40:
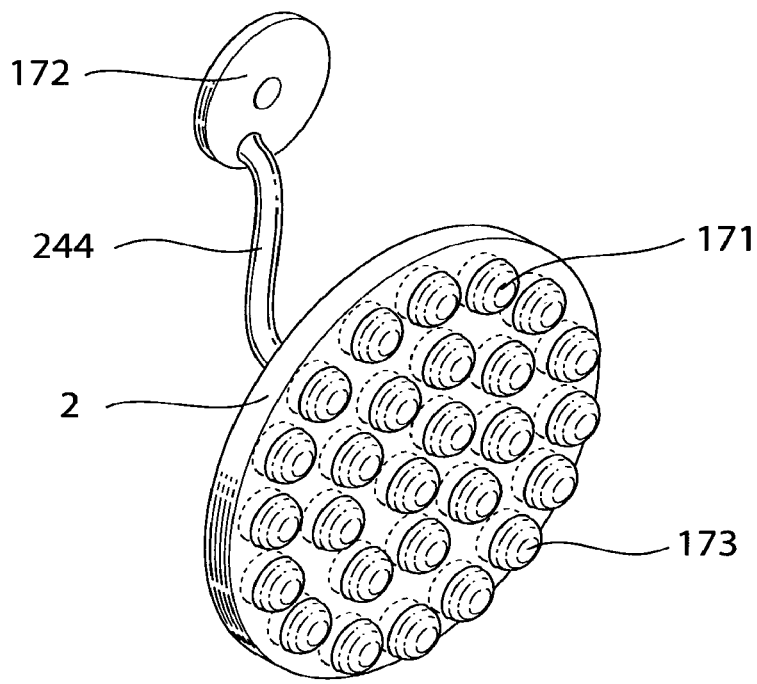
FIG. 40 shows a heart contacting organ in detail.

FIG. 40 shows an embodiment in which multiple cushions 171 are placed on the heart contacting organ 2. The cushions 171 could be raised and lowered in relation to the heart contacting organ 2 to change the position of the force exerted on the heart H. FIG. 17C further shows a connecting arm 244 in connection with an operating device 172 for adjusting the location of the heart contacting organ 2 in relation to the heart H. The operating device 172 could be electrically, mechanically, hydraulically or pneumatically operated and could be adapter to be remotely controlled from outside of the human body using a remote control. It is also conceivable that the connecting arm 244 could be manually adjusted during a surgical or laparoscopic procedure. In the embodiment where the cushions 171 or pistons 173 are hydraulic or pneumatically operated the implantable device could further comprise a hydraulic or pneumatic system (not shown) for changing the volume of the cushion 171 or the volume under the piston 173, by moving a hydraulic or pneumatic fluid to or from the cushion 171.

Figure 41:
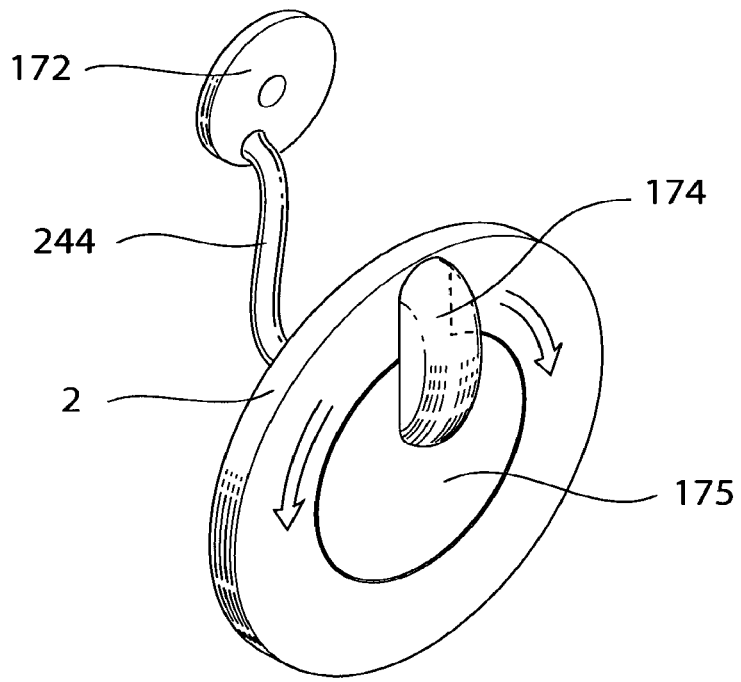
FIG. 41 shows a heart contacting organ in detail.

FIG. 41 shows an embodiment where the heart contacting organ 2 comprises a cushion 174 that exerts force in the heart H. The cushion 174 can be moved on the heart contacting organ 2 to change the position of the force exerted on the heart H. According to this embodiment the heart contacting organ further comprises a rotational element 175 that rotates to create the movement of the cushion 174 on the great contacting organ 2. The rotational element could be operable manually, electrically, mechanically, hydraulically or pneumatically, and can further be adapted to be remotely controlled from outside of the human body using a remote control. FIG. 17D further shows a connecting arm 244 in connection with an operating device 172 for adjusting the location of the heart contacting organ 2 in relation to the heart H. The operating device 172 could be electrically, mechanically, hydraulically or pneumatically operated and could be adapter to be remotely controlled from outside of the human body using a remote control.

Figure 42:
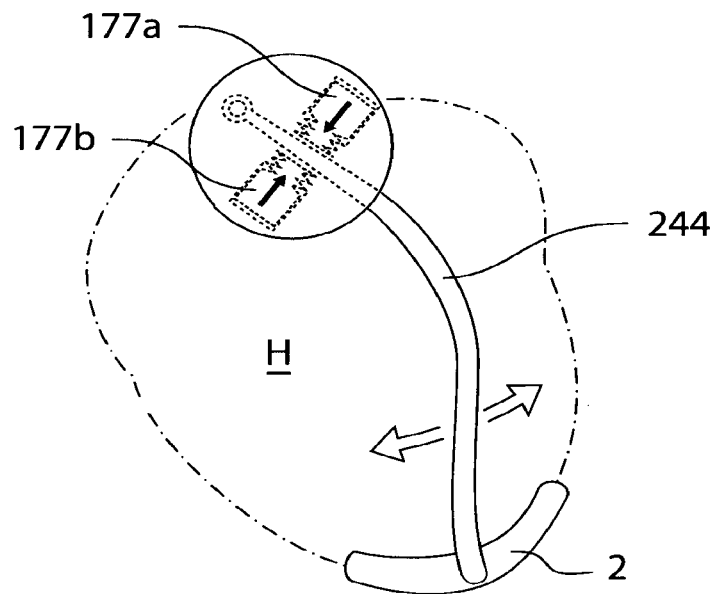
FIG. 42 shows a device for adjusting a heart contacting organ in a first position.

FIG. 42 shows the embodiment according to FIG. 38 when implanted in a human body. The heart contacting organ 2 comprising cushions 171 and/or pistons 173 which could be raised and lowered in relation to the heart contacting organ to change the position of the force exerted on the heart H. The implantable device further comprises a connecting arm 244 in contact with the heart contacting organ 2 and an operating device 172 for operating the connecting arm 244. The operating device is in contact with the plate of the first fixating member 242a that together with the second fixating member 242b fixates the implantable device to a structure of the human body comprising bone 240. The implantable device further comprises a control unit 176 for controlling the heart pump device, the operating device 172 and the cushions 171 and/or pistons 173 placed on the heart contacting organ 2.

Figure 43:
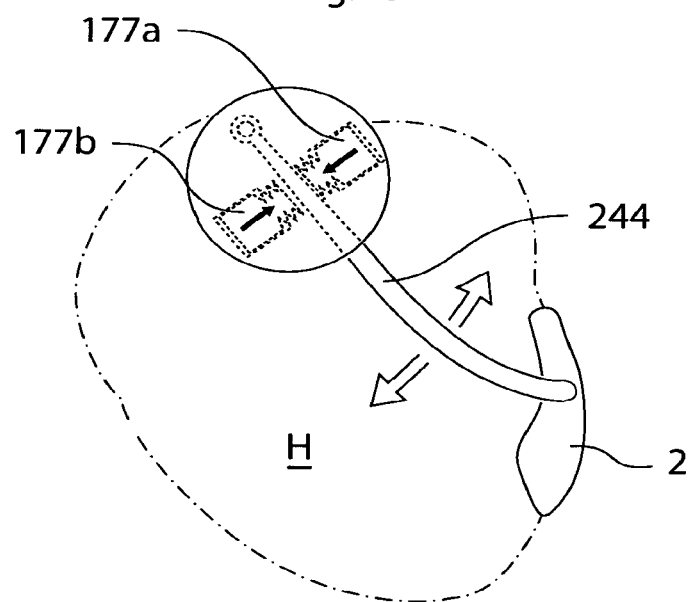
FIG. 43 shows a device for adjusting a heart contacting organ in a second position.

FIG. 43 shows an embodiment where the heart contacting organ 2 is operable to change the position of the force exerted on the heart H using two operating devices 177a,b the two operating devices could be mechanical, hydraulic or pneumatic devices. The heart contacting organ is operable through the connection with the operating device through the connecting arm 244 hinged to the heart contacting organ and the implantable device comprising the two operating devices 177a,b. According to other embodiments the connecting arm 244 is operable using only one operating device, in which case that operating device could be adapted for powered movement in two directions, or adapted for powered movement in one direction and spring loaded movement in the other direction.

Figure 44:
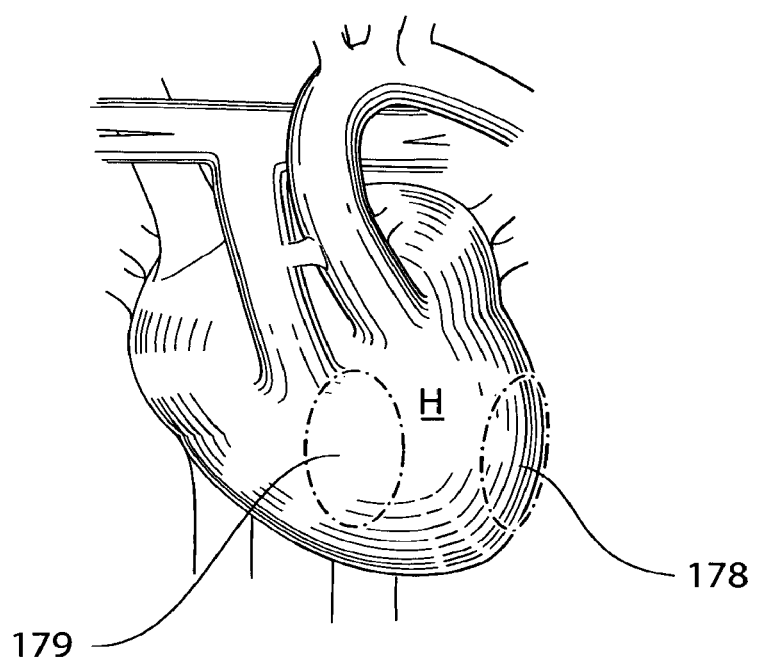
FIG. 44 shows a heart of a human patient in a frontal view.

FIG. 44 shows the heart H of a human patient H in a frontal view wherein 179 indicates the right ventricle which is a possible position for exerting force, and 178 indicates the left ventricle which also is a possible position for exerting force. It is also conceivable that force could be exerted on two different sides of the right 179 or left 178 ventricle, respectively.

Figure 45:
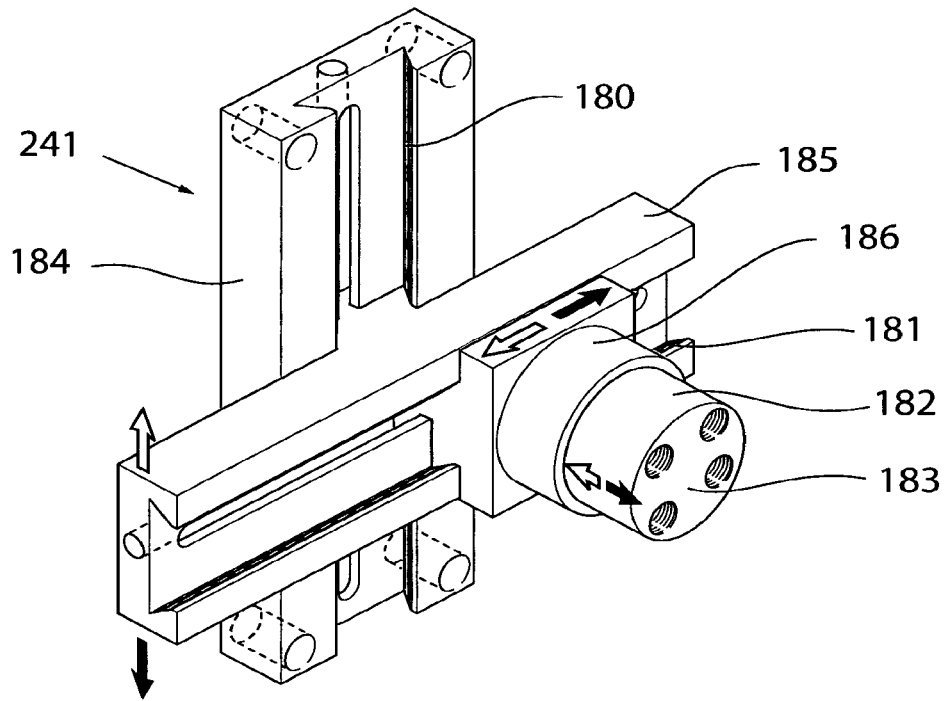
FIG. 45 shows a system for adjusting the position of a pump device in a first position.

FIG. 45 shows the implantable device 1 according to an embodiment where a pump device 3 is placed on an adjustment system comprising a first fixating member 241, a second fixating member 185 and a third fixating member 186. The first fixating member 241 is adapter for fixation in a structure of the human body comprising bone 240. The first fixating member comprises a first trench wherein the second fixating member 185 is adapted to move. The second fixating member 185 in turn comprises a second trench wherein the third fixating member 186 is adapted to move. The third fixating member 186 comprises a piston 182 which can be raised and lowered for adjusting the pump device 1 in a third axis. The third fixating member comprises a surface 183 to which the pump device 3 can be fixated. Using said adjustment system the pump device 3 can be adjusted three dimensionally which can change the position of the force exerted on the heart H. The adjustment system can be operable by means of an implantable motor, the motor could be an electric, hydraulic or pneumatic motor. The motor could be adapted to be remotely controlled from outside of the human body using a remote control. The pump device 3 could hence be post-operatively adjusted by the patient or by a physician. The position of the pump device 3 could be verified from the outside of the human body using x-ray or ultra-sound.

Figure 46:
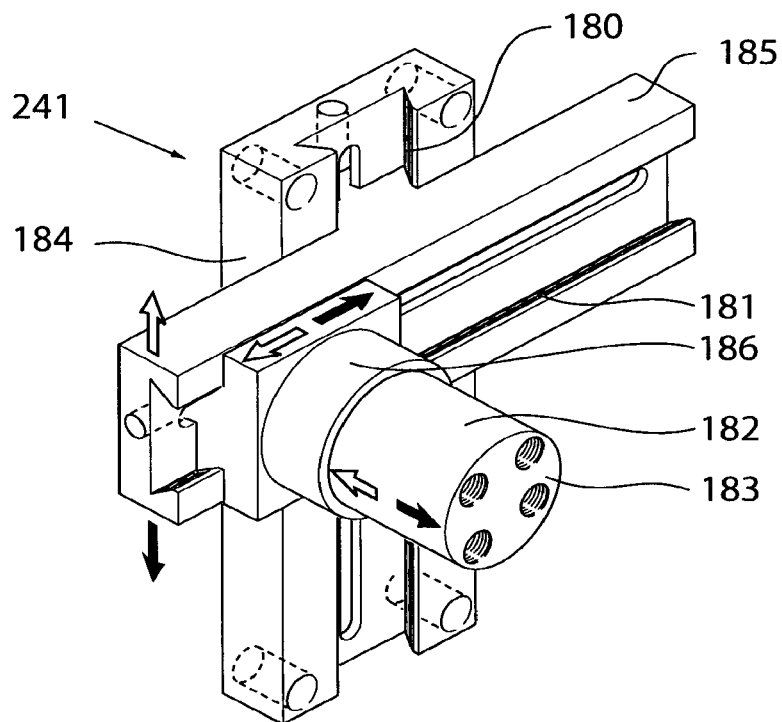
FIG. 46 shows a system for adjusting the position of a pump device in a second position.

FIG. 46 shows the adjustable system described in FIG. 17H in a second position.

The embodiments for changing the position of the force exerted on the heart H of a human patent described above could easily be combined with any of the embodiments of implantable devices described earlier.

FIGS. 47-60 show the fixation of an implantable device to a structure of the human body comprising bone 240. The structure could be the sternum, a part of the rib cage, comprising one or more ribs or a part of the vertebral column comprising at least one vertebra. According to one embodiment the implantable device 1 is fixated to the structure of the human body comprising bone 240 trough a fixating member 241 said fixating member could comprise a plate 242 which is in contact with the structure of the human body comprising bone 240. The implantable device 1 could also be fixated to the structure of the human body comprising bone 240 using a second fixating member 241b which also could comprise a plate 242b in which in turn could be in contact with the structure of the human body comprising bone 240.

Figure 47:
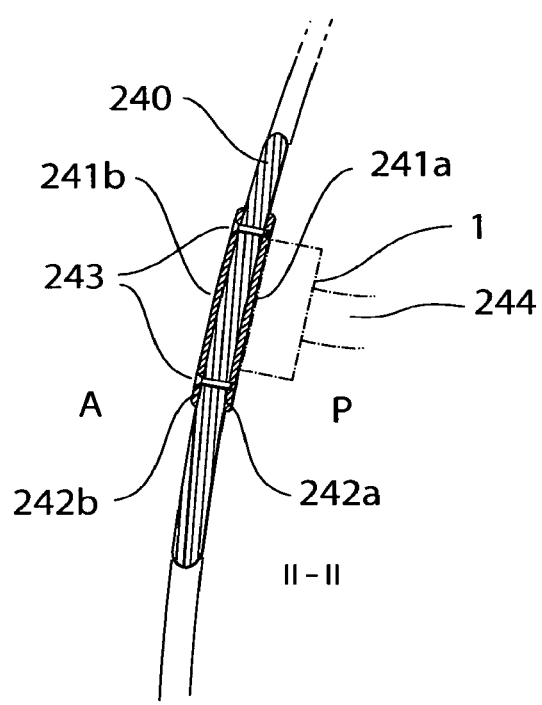
FIG. 47 shows a fixation system.

FIG. 47 shows an embodiment where the implantable device 1 is fixated to a structure of the human body comprising bone 240. The structure could be the sternum, a part of the rib cage comprising one or more ribs or a part of the vertebral column structure comprising at least one vertebra. According to the embodiment the implantable device 1 comprises a first fixating member 241a comprising a plate 242a and a second fixating member 241b comprising a plate 242b. The first and second fixating members are attached to each other using through-going screws 243 placed from the anterior side A of the structure of the human body comprising bone 240. An alternative embodiment could comprise screws placed from the posterior side P of the structure of the human body comprising bone 240. The first fixating member 241a and the second fixating member 241b clamp the structure of the human body comprising bone 240. The fixating member 241a could be in contact with a connecting arm 244 which in turn could be in contact with a heart pump device.

Figure 48:
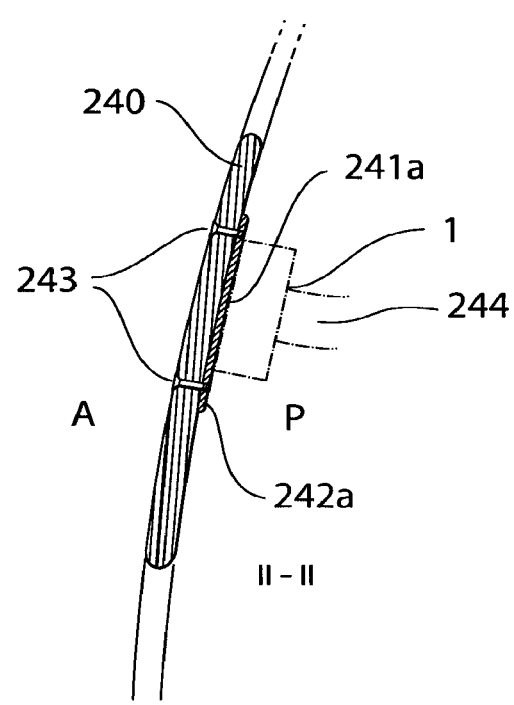
FIG. 48 shows a fixation system.

FIG. 48 shows an embodiment where the implantable device 1 is fixated to a structure of the human body comprising bone 240 using only one fixating member 241a comprising a plate 242a. The structure could be the sternum, a part of the rib cage comprising one or more ribs or a part of the vertebral column structure comprising at least one vertebra. Through-going screws 243 is placed form the anterior side A the structure of the human body comprising bone 240 and fixated in the plate 242a. An alternative embodiment could comprise screws placed from the posterior side P of the structure of the human body comprising bone 240 in which case the screws could be fixated in nuts placed in connection with the structure of the human body comprising bone, or fixated in directly in the bone of the structure of the human body comprising bone 240. The fixating member 241a could be in contact with a connecting arm 244 which in turn could be in contact with a heart pump device.

Figure 49:
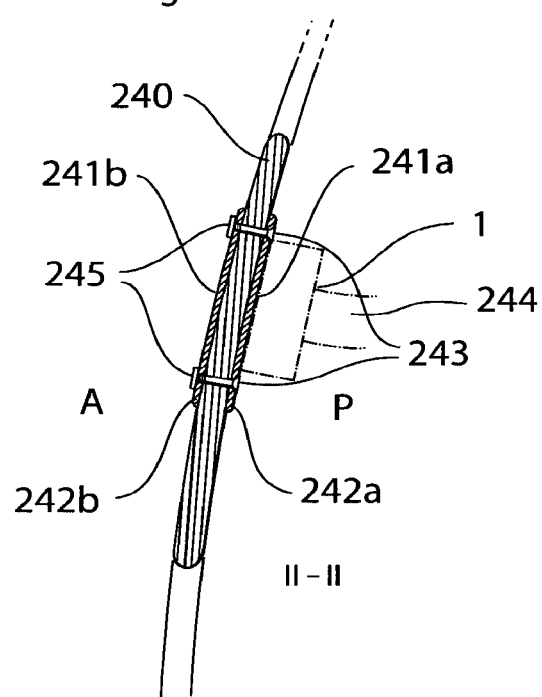
FIG. 49 shows a fixation system.

FIG. 49 shows an embodiment where the implantable device 1 is fixated to a structure of the human body comprising bone 240. The structure could be the sternum, a part of the rib cage comprising one or more ribs or a part of the vertebral column comprising at least one vertebra. According to the embodiment the implantable device 1 comprises a first fixating member 241a comprising a plate 242a and a second fixating member 241b comprising a plate 242b. The first and second fixating members are attached to each other using through-going screws 243 placed from the posterior side P of the structure of the human body comprising bone 240. The screws are fixated to nuts 245 placed on the anterior side of the structure comprising bone 240. An alternative embodiment could comprise screws placed from the anterior side A of the structure of the human body comprising bone 240, in which case the nuts is placed on the posterior side P of the structure comprising bone 240. The first fixating member 241a and the second fixating member 241b clamp the structure of the human body comprising bone 240. The fixating member 241a could be in contact with a connecting arm 244 which in turn could be in contact with a heart pump device.

Figure 50:
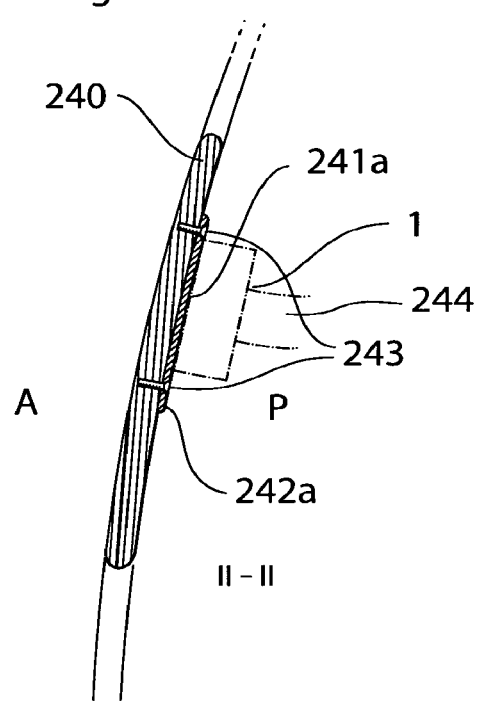
FIG. 50 shows a fixation system.

FIG. 50 shows an embodiment where the implantable device 1 is fixated to a structure of the human body comprising bone 240 using only one fixating member 241a comprising a plate 242a. The structure could be the sternum, a part of the rib cage comprising one or more ribs or a part of the vertebral column structure comprising at least one vertebra. Screws 243 that fixates the fixating member to the structure of the human body comprising bone is placed form the posterior side P the structure of the human body comprising bone 240. The screws fixates the fixating member to both the posterior and the anterior cortex of the structure of the human body comprising bone 240, however it is conceivable that the screws are fixated only to the anterior or posterior cortex. An alternative embodiment could comprise screws placed from the anterior side a of the structure of the human body comprising bone 240, in which case the fixating member 241a is placed on the anterior side A of the structure of the human body comprising bone 240.

Figure 51:
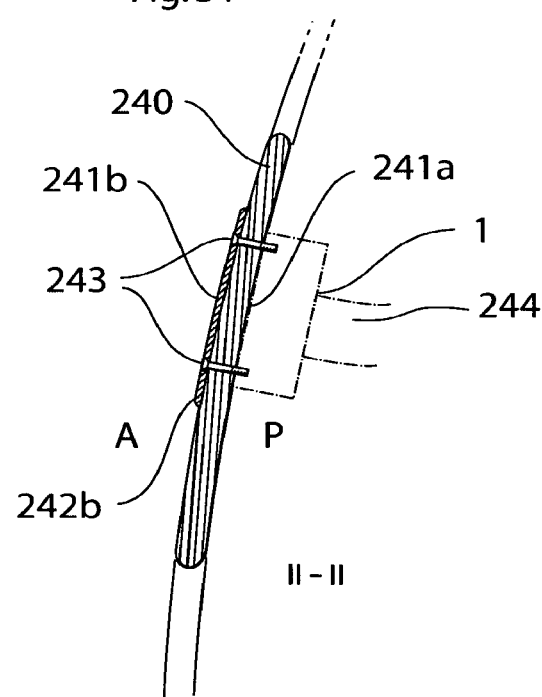
FIG. 51 shows a fixation system.

FIG. 51 shows an embodiment where the implantable device 1 is fixated to a structure of the human body comprising bone 240 using one fixating member 241b comprising a plate 242b, and one fixating member 241a without a plate. The structure could be the sternum, a part of the rib cage comprising one or more ribs or a part of the vertebral column structure comprising at least one vertebra. Screws 243 that fixates the fixating members 241a,b to the structure of the human body comprising bone 240 is placed form the anterior side A of the structure of the human body comprising bone 240 and fixated in the fixating member 241a. The first fixating member 241a and the second fixating member 241b clamp the structure of the human body comprising bone 240. The fixating member 241a could be in contact with a connecting arm 244 which in turn could be in contact with a heart pump device.

Figure 52:
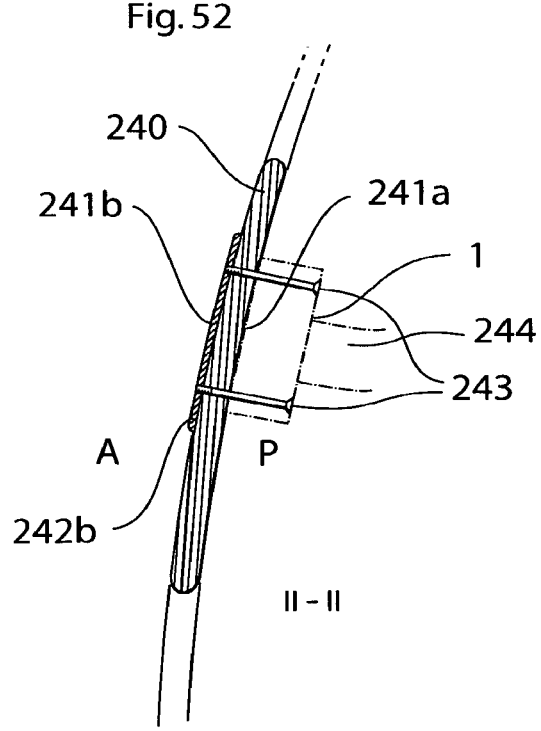
FIG. 52 shows a fixation system.

FIG. 52 shows an embodiment where the implantable device 1 is fixated to a structure of the human body comprising bone 240 using one fixating member 241b comprising a plate 242b, and one fixating member 241a without a plate. The structure could be the sternum, a part of the rib cage comprising one or more ribs or a part of the vertebral column structure comprising at least one vertebra. Screws 243 that fixates the fixating members 241a,b to the structure of the human body comprising bone 240 is placed form the posterior side P of the structure of the human body comprising bone 240 and fixated in the plate 242b of the fixating member 241b. The first fixating member 241a and the second fixating member 241b clamp the structure of the human body comprising bone 240. The fixating member 241a could be in contact with a connecting arm 244 which in turn could be in contact with a heart pump device.

Figure 53:
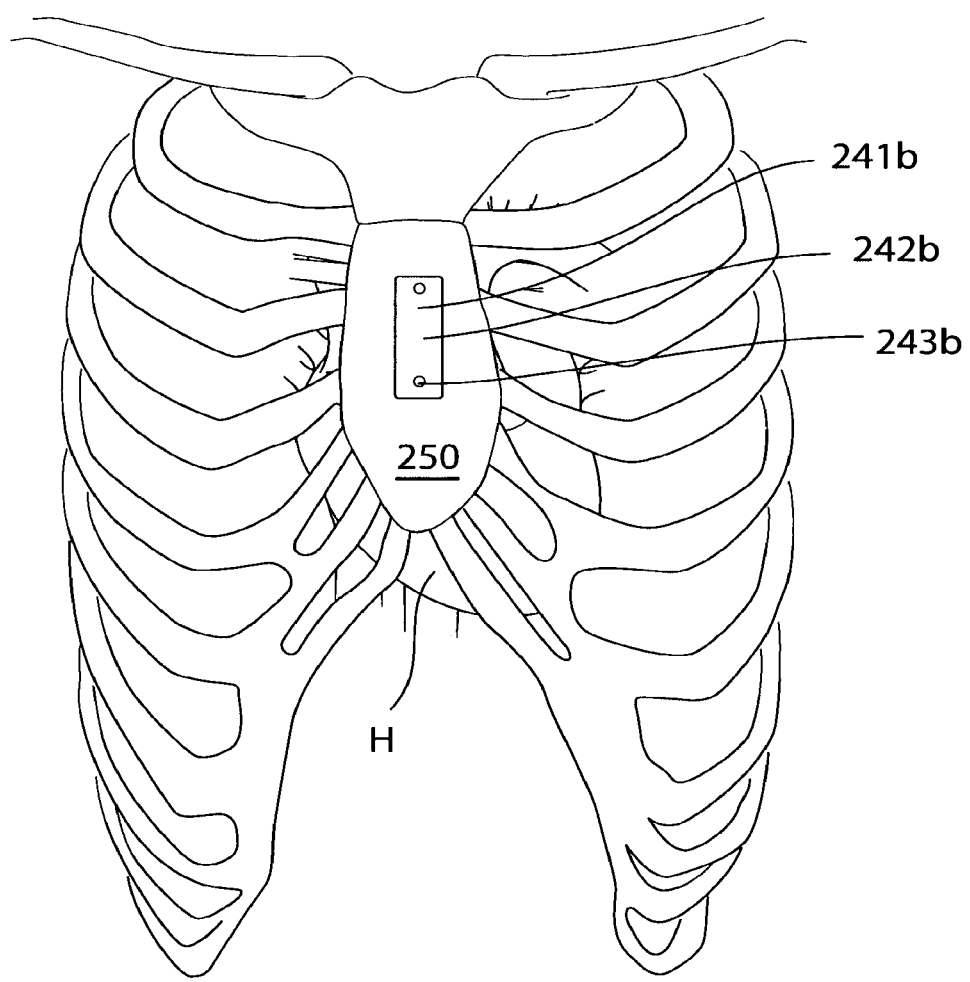
FIG. 53 shows a frontal view of the sternum of a human patient, with a fixating system applied.

FIG. 53 shows an embodiment where the implantable device 1 is adapted to be fixated to the sternum 250 of a human patient. The device is fixated using a fixating member 241b which is fixated to the sternum using screws 243. However the implantable device could be fixated to the sternum 250 of a human patent using any of the ways to place the fixating members described previously.

Figure 54:
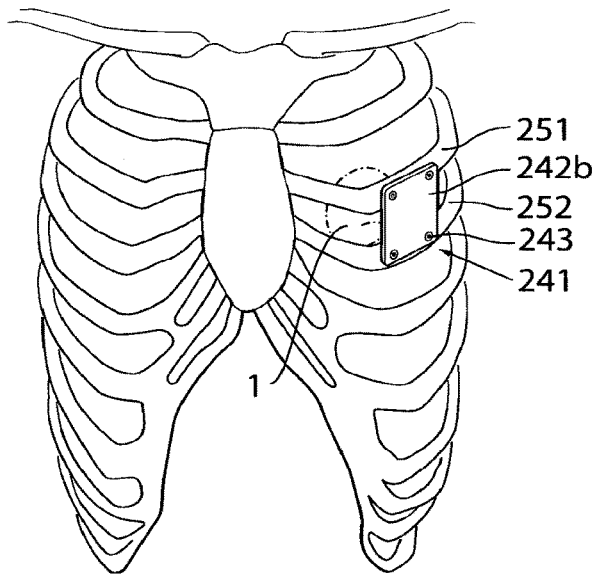
FIG. 54 shows a frontal view of the rib cage of a human patient, with a fixating system applied.

FIG. 54 shows an embodiment where the implantable device 1 is adapted to be fixated to two ribs 251, 252. A fixating member 241 comprising a plate 242b is fixated with screws adapted to fixate the fixating member to the cortex of the ribs.

Figure 55:
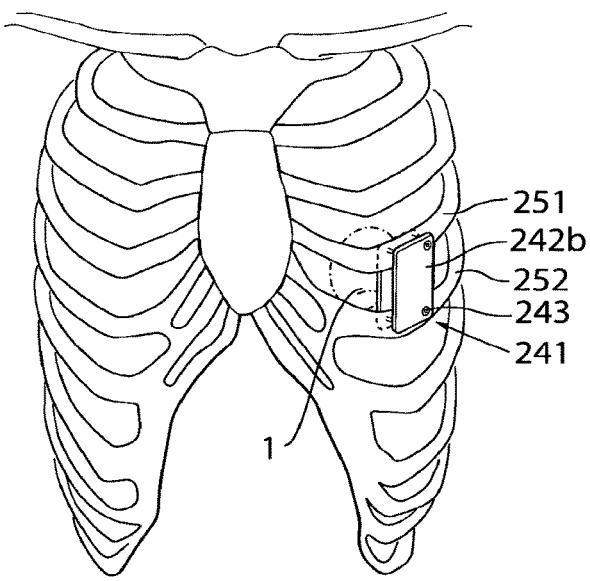
FIG. 55 shows a frontal view of the rib cage of a human patient, with a fixating system applied.

FIG. 55 shows an embodiment where the implantable device 1 is adapted to be fixated to two ribs 251, 252. A first plate 242a is provided on the posterior side of the rib cage, whereas a second plate 242b is provided in the anterior side of the rib cage. Screws 243 penetrate the ribs and fixates the first plate 242a to the second plate 242b. The tightening of the screws creates a clamping effect of the ribs 251,251 and provides the fixation of the implantable device 1. In another embodiment (not shown) the screws 243 are placed between the ribs 251,252 and that ways provides a clamping effect of the ribs 251,252.

Figure 56:
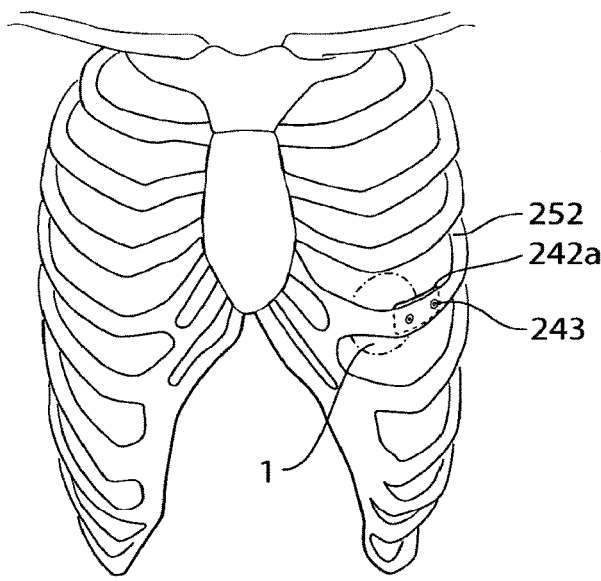
FIG. 56 shows a frontal view of the rib cage of a human patient, with a fixating system applied.

FIG. 56 shows an embodiment where the implantable device 1 is adapted to be fixated to one rib 252. A plate 242a is provided on the posterior side of the rib cage and screws 243 are provided from the outside thereof, penetrating the rib 252 and fixating the plate 242a to the rib 252.

Figure 57:
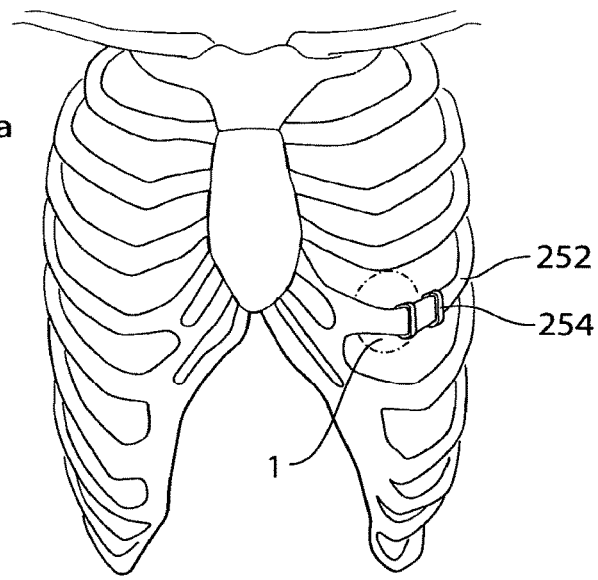
FIG. 57 shows a frontal view of the rib cage of a human patient, with a fixating system applied.

FIG. 57 shows an embodiment where the implantable device 1 is adapted to be fixated to one rib 252 using cord or band 254, this way there is no need to penetrate the rib 252. However the implantable device could be fixated to the ribcage of a human patent using any of the ways to place the fixating members described previously.

FIG. 58 shows an embodiment where the implantable device 1 is adapted to be fixated to a vertebra 255 of the vertebral column. A fixating member 241 is fixated to the vertebra 255 using screws 243. The implantable device further comprises a connecting connecting arm 244 that connects the implantable device 1 to the fixating member 241.

FIG. 59 shows an embodiment where the implantable device 1 is adapted to be fixated to two vertebras 255, 256 of the vertebral column. A fixating member 241 is fixated to the two vertebras 255, 256 using screws 243. The implantable device further comprises a connecting arm 244 that connects the implantable device 1 to the fixating member 241.

FIG. 60 shows an embodiment where the implantable device is adapted to be fixated to a vertebra 255 of the vertebral column by clamping said vertebra 255. Two fixating members 241a, 241b is placed on two sides of the vertebra and an attachment comprising screws 243 clamps the vertebra between the first and second fixating members 241a,b. The implantable device further comprises a connecting arm 244 that connects the implantable device 1 to the fixating member 241.

In all of the above-mentioned embodiments the means of attachment could be replaced with other mechanical attachments or an adhesive. Other mechanical attachments suitable could be: pop-rivets, nails, staples, band or cord. The mechanical fixating members could be of a metallic or ceramic material. Suitable metallic materials could be titanium or surgical steel.

Figure 61:
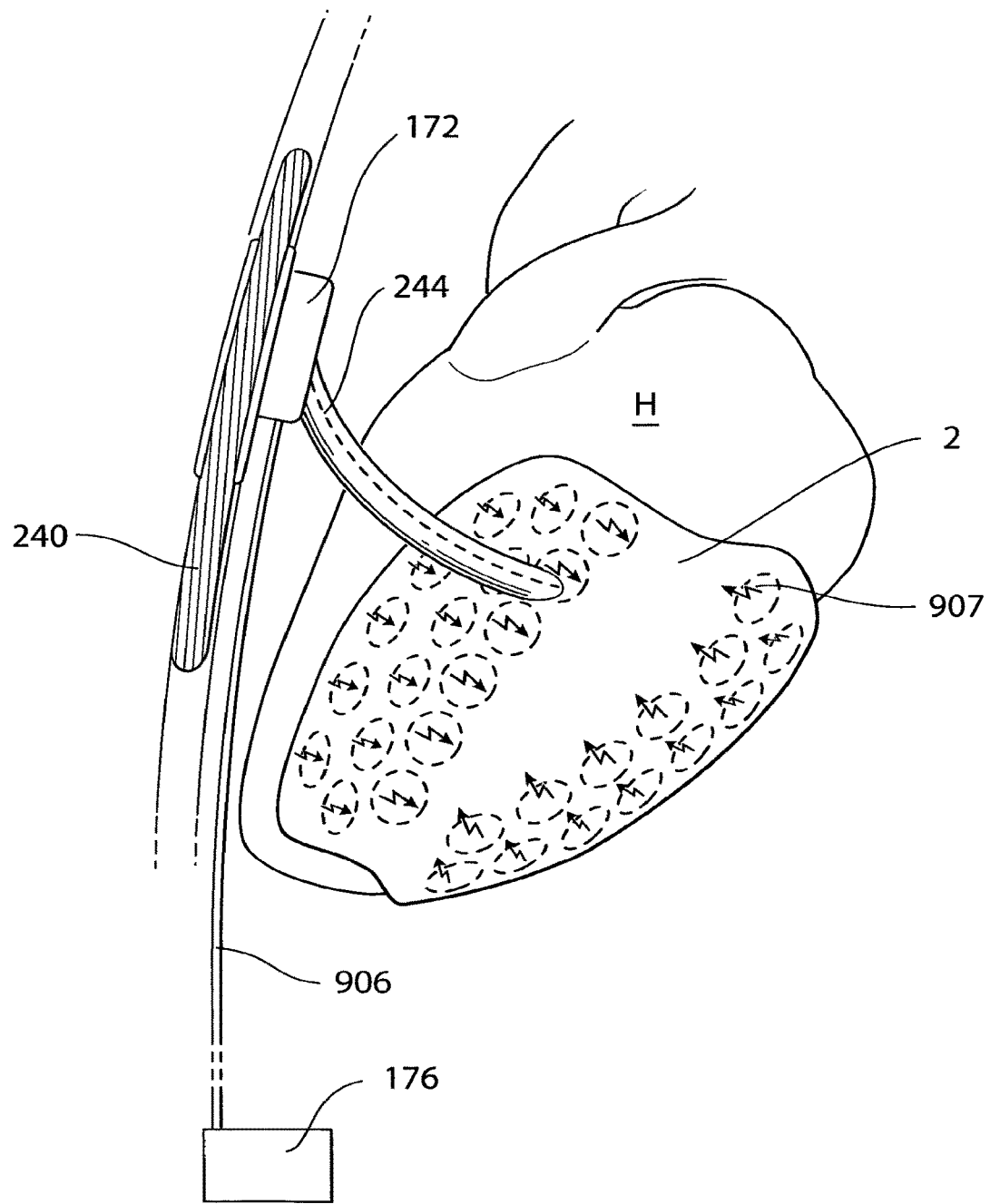
FIG. 61 shows an implantable device for improving the pump function of the heart in a lateral view.

FIG. 61 shows an embodiment where the heart contacting organ 2 is adapted to compress the heart H to assist the pump function thereof. A stimulation device 907 is attached to the heart contacting organ 2 and is adapted to stimulate the heart H to achieve an additional assistance of said pump function after the heart contacting organ 2 has placed the heart in the compressed state. According to an embodiment the heart contacting organ is attached to a connecting arm 244 which in turn is attached to a mechanical, electrical or hydraulic operating device 172 which operates the heart contacting organ 2. The operating device 172 is in turn attached a fixating member which fixates the device to a structure of the human body comprising bone 244 using mechanical fixating members such as screws, or adhesive. A control device 176 for controlling the operating device 172 in accordance with any of the embodiments described in this application is in connection with said operating device 172 though a connecting member 906. However it is also conceivable that the control device 176 communicates wirelessly with the operating device 172.

Figure 62:
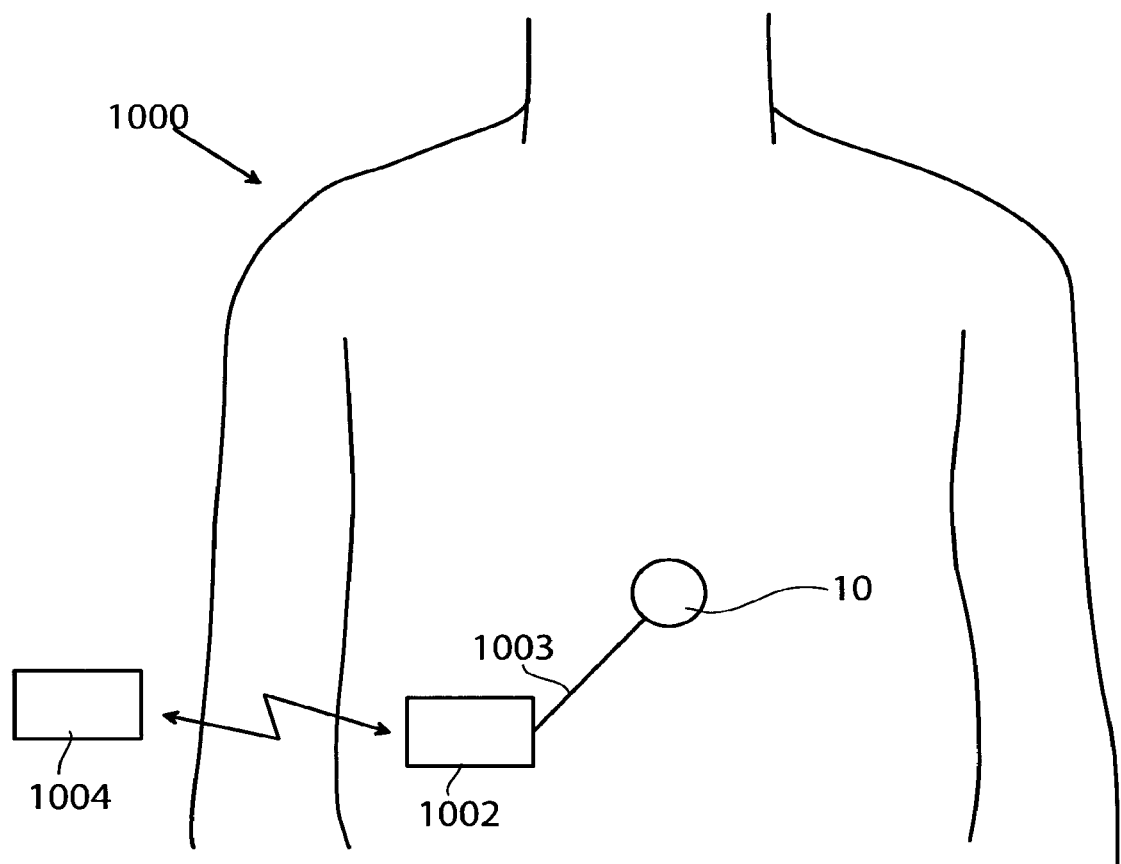
FIG. 62 illustrates a system for treating a disease, wherein the system includes an apparatus implanted in a patient.

FIG. 62 illustrates a system for treating a disease comprising an apparatus 10 placed in the abdomen of a patient. An implanted energy-transforming device 1002 is adapted to supply energy consuming components of the apparatus with energy via a power supply line 1003. An external energy-transmission device 1004 for non-invasively energizing the apparatus 10 transmits energy by at least one wireless energy signal. The implanted energy-transforming device 1002 transforms energy from the wireless energy signal into electric energy which is supplied via the power supply line 1003.

The implanted energy-transforming device 1002 may also comprise other components, such as: a coil for reception and/or transmission of signals and energy, an antenna for reception and/or transmission of signals, a microcontroller, a charge control unit, optionally comprising an energy storage, such as a capacitor, one or more sensors, such as temperature sensor, pressure sensor, position sensor, motion sensor etc., a transceiver, a motor, optionally including a motor controller, a pump, and other parts for controlling the operation of a medical implant.

The wireless energy signal may include a wave signal selected from the following: a sound wave signal, an ultrasound wave signal, an electromagnetic wave signal, an infrared light signal, a visible light signal, an ultra violet light signal, a laser light signal, a micro wave signal, a radio wave signal, an x-ray radiation signal and a gamma radiation signal. Alternatively, the wireless energy signal may include an electric or magnetic field, or a combined electric and magnetic field.

The wireless energy-transmission device 1004 may transmit a carrier signal for carrying the wireless energy signal. Such a carrier signal may include digital, analogue or a combination of digital and analogue signals. In this case, the wireless energy signal includes an analogue or a digital signal, or a combination of an analogue and digital signal.

Generally speaking, the energy-transforming device 1002 is provided for transforming wireless energy of a first form transmitted by the energy-transmission device 1004 into energy of a second form, which typically is different from the energy of the first form. The implanted apparatus 10 is operable in response to the energy of the second form. The energy-transforming device 1002 may directly power the apparatus with the second form energy, as the energy-transforming device 1002 transforms the first form energy transmitted by the energy-transmission device 1004 into the second form energy. The system may further include an implantable accumulator, wherein the second form energy is used at least partly to charge the accumulator.

Alternatively, the wireless energy transmitted by the energy-transmission device 1004 may be used to directly power the apparatus, as the wireless energy is being transmitted by the energy-transmission device 1004. Where the system comprises an operation device for operating the apparatus, as will be described below, the wireless energy transmitted by the energy-transmission device 1004 may be used to directly power the operation device to create kinetic energy for the operation of the apparatus.

The wireless energy of the first form may comprise sound waves and the energy-transforming device 1002 may include a piezo-electric element for transforming the sound waves into electric energy. The energy of the second form may comprise electric energy in the form of a direct current or pulsating direct current, or a combination of a direct current and pulsating direct current, or an alternating current or a combination of a direct and alternating current. Normally, the apparatus comprises electric components that are energized with electrical energy. Other implantable electric components of the system may be at least one voltage level guard or at least one constant current guard connected with the electric components of the apparatus.

Optionally, one of the energy of the first form and the energy of the second form may comprise magnetic energy, kinetic energy, sound energy, chemical energy, radiant energy, electromagnetic energy, photo energy, nuclear energy or thermal energy. Preferably, one of the energy of the first form and the energy of the second form is non-magnetic, non-kinetic, non-chemical, non-sonic, non-nuclear or non-thermal.

The energy-transmission device may be controlled from outside the patient's body to release electromagnetic wireless energy, and the released electromagnetic wireless energy is used for operating the apparatus. Alternatively, the energy-transmission device is controlled from outside the patient's body to release non-magnetic wireless energy, and the released non-magnetic wireless energy is used for operating the apparatus.

The external energy-transmission device 1004 also includes a wireless remote control having an external signal transmitter for transmitting a wireless control signal for non-invasively controlling the apparatus. The control signal is received by an implanted signal receiver which may be incorporated in the implanted energy-transforming device 1002 or be separate there from.

The wireless control signal may include a frequency, amplitude, or phase modulated signal or a combination thereof. Alternatively, the wireless control signal includes an analogue or a digital signal, or a combination of an analogue and digital signal. Alternatively, the wireless control signal comprises an electric or magnetic field, or a combined electric and magnetic field.

The wireless remote control may transmit a carrier signal for carrying the wireless control signal. Such a carrier signal may include digital, analogue or a combination of digital and analogue signals. Where the control signal includes an analogue or a digital signal, or a combination of an analogue and digital signal, the wireless remote control preferably transmits an electromagnetic carrier wave signal for carrying the digital or analogue control signals.

FIG. 63 illustrates the system of FIG. 62 in the form of a more generalized block diagram showing the apparatus 10, the energy-transforming device 1002 powering the apparatus 10 via power supply line 1003, and the external energy-transmission device 1004, The patient's skin 1005, generally shown by a vertical line, separates the interior of the patient to the right of the line from the exterior to the left of the line.

FIG. 64 shows an embodiment identical to that of FIG. 63, except that a reversing device in the form of an electric switch 1006 operable for example by polarized energy also is implanted in the patient for reversing the apparatus 10. When the switch is operated by polarized energy the wireless remote control of the external energy-transmission device 1004 transmits a wireless signal that carries polarized energy and the implanted energy-transforming device 1002 transforms the wireless polarized energy into a polarized current for operating the electric switch 1006. When the polarity of the current is shifted by the implanted energy-transforming device 1002 the electric switch 1006 reverses the function performed by the apparatus 10.

FIG. 65 shows an embodiment identical to that of FIG. 63, except that an operation device 1007 implanted in the patient for operating the apparatus 10 is provided between the implanted energy-transforming device 1002 and the apparatus 10. This operation device can be in the form of a motor 1007, such as an electric servomotor. The motor 1007 is powered with energy from the implanted energy-transforming device 1002, as the remote control of the external energy-transmission device 1004 transmits a wireless signal to the receiver of the implanted energy-transforming device 1002.

FIG. 66 shows an embodiment identical to that of FIG. 63, except that it also comprises an operation device is in the form of an assembly 1008 including a motor/pump unit 1009 and a fluid reservoir 1010 is implanted in the patient. In this case the apparatus 10 is hydraulically operated, i.e. hydraulic fluid is pumped by the motor/pump unit 1009 from the fluid reservoir 1010 through a conduit 1011 to the apparatus 10 to operate the apparatus, and hydraulic fluid is pumped by the motor/pump unit 1009 back from the apparatus 10 to the fluid reservoir 1010 to return the apparatus to a starting position. The implanted energy-transforming device 1002 transforms wireless energy into a current, for example a polarized current, for powering the motor/pump unit 1009 via an electric power supply line 1012.

Instead of a hydraulically operated apparatus 10, it is also envisaged that the operation device comprises a pneumatic operation device. In this case, the hydraulic fluid can be pressurized air to be used for regulation and the fluid reservoir is replaced by an air chamber.

In all of these embodiments the energy-transforming device 1002 may include a rechargeable accumulator like a battery or a capacitor to be charged by the wireless energy and supplies energy for any energy consuming part of the system.

As an alternative, the wireless remote control described above may be replaced by manual control of any implanted part to make contact with by the patient's hand most likely indirect, for example a press button placed under the skin.

Figure 67:
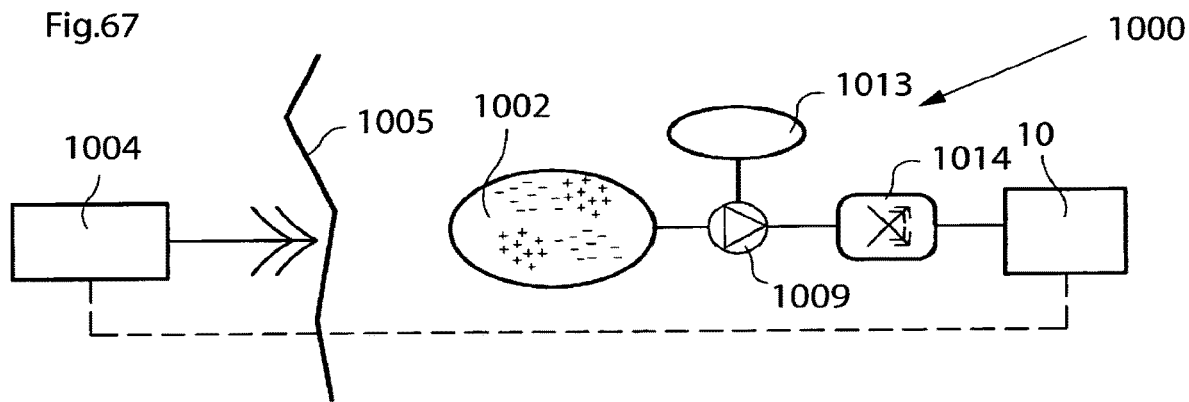

FIG. 67 shows an embodiment comprising the external energy-transmission device 1004 with its wireless remote control, the apparatus 10, in this case hydraulically operated, and the implanted energy-transforming device 1002, and further comprising a hydraulic fluid reservoir 1013, a motor/pump unit 1009 and an reversing device in the form of a hydraulic valve shifting device 1014, all implanted in the patient. Of course the hydraulic operation could easily be performed by just changing the pumping direction and the hydraulic valve may therefore be omitted. The remote control may be a device separated from the external energy-transmission device or included in the same. The motor of the motor/pump unit 1009 is an electric motor. In response to a control signal from the wireless remote control of the external energy-transmission device 1004, the implanted energy-transforming device 1002 powers the motor/pump unit 1009 with energy from the energy carried by the control signal, whereby the motor/pump unit 1009 distributes hydraulic fluid between the hydraulic fluid reservoir 1013 and the apparatus 10. The remote control of the external energy-transmission device 1004 controls the hydraulic valve shifting device 1014 to shift the hydraulic fluid flow direction between one direction in which the fluid is pumped by the motor/pump unit 1009 from the hydraulic fluid reservoir 1013 to the apparatus 10 to operate the apparatus, and another opposite direction in which the fluid is pumped by the motor/pump unit 1009 back from the apparatus 10 to the hydraulic fluid reservoir 1013 to return the apparatus to a starting position.

Figure 68:
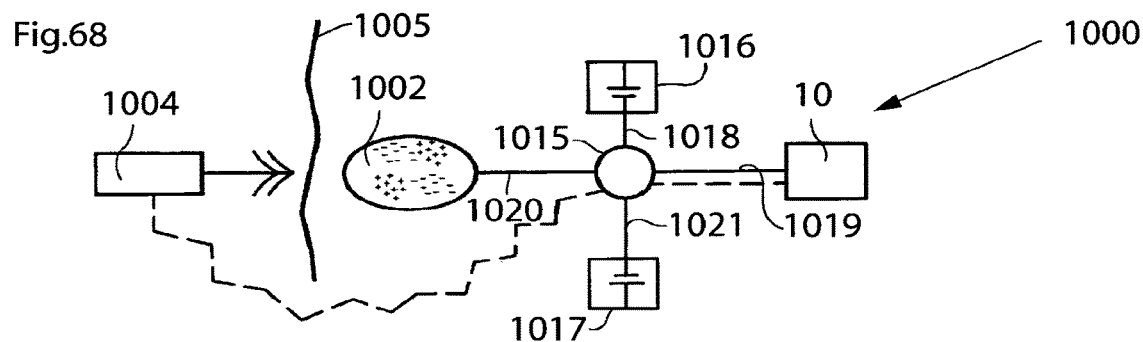

FIG. 68 shows an embodiment comprising the external energy-transmission device 1004 with its wireless remote control, the apparatus 10, the implanted energy-transforming device 1002, an implanted internal control unit 1015 controlled by the wireless remote control of the external energy-transmission device 1004, an implanted accumulator 1016 and an implanted capacitor 1017. The internal control unit 1015 arranges storage of electric energy received from the implanted energy-transforming device 1002 in the accumulator 1016, which supplies energy to the apparatus 10. In response to a control signal from the wireless remote control of the external energy-transmission device 1004, the internal control unit 1015 either releases electric energy from the accumulator 1016 and transfers the released energy via power lines 1018 and 1019, or directly transfers electric energy from the implanted energy-transforming device 1002 via a power line 1020, the capacitor 1017, which stabilizes the electric current, a power line 1021 and the power line 1019, for the operation of the apparatus 10.

The internal control unit is preferably programmable from outside the patient's body. In a preferred embodiment, the internal control unit is programmed to regulate the apparatus 10 according to a pre-programmed time-schedule or to input from any sensor sensing any possible physical parameter of the patient or any functional parameter of the system.

In accordance with an alternative, the capacitor 1017 in the embodiment of FIG. 7 10 may be omitted. In accordance with another alternative, the accumulator 1016 in this embodiment may be omitted.

Figure 69:
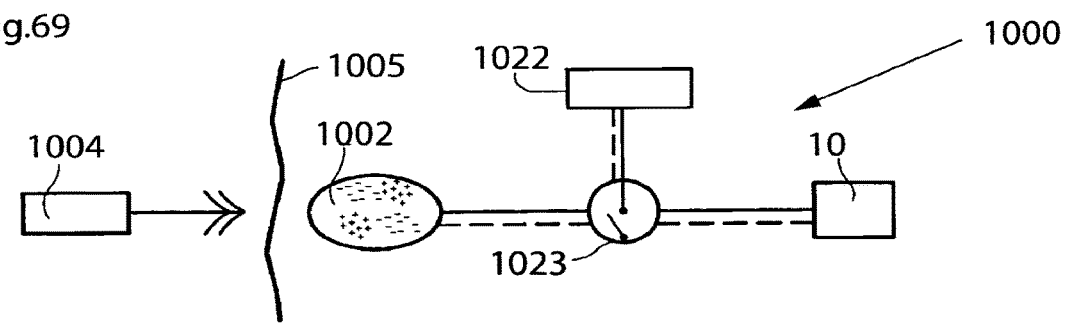

FIG. 69 shows an embodiment identical to that of FIG. 63, except that a battery 1022 for supplying energy for the operation of the apparatus 10 and an electric switch 1023 for switching the operation of the apparatus 10 also are implanted in the patient. The electric switch 1023 may be controlled by the remote control and may also be operated by the energy supplied by the implanted energy-transforming device 1002 to switch from an off mode, in which the battery 1022 is not in use, to an on mode, in which the battery 1022 supplies energy for the operation of the apparatus 10.

Figure 70:
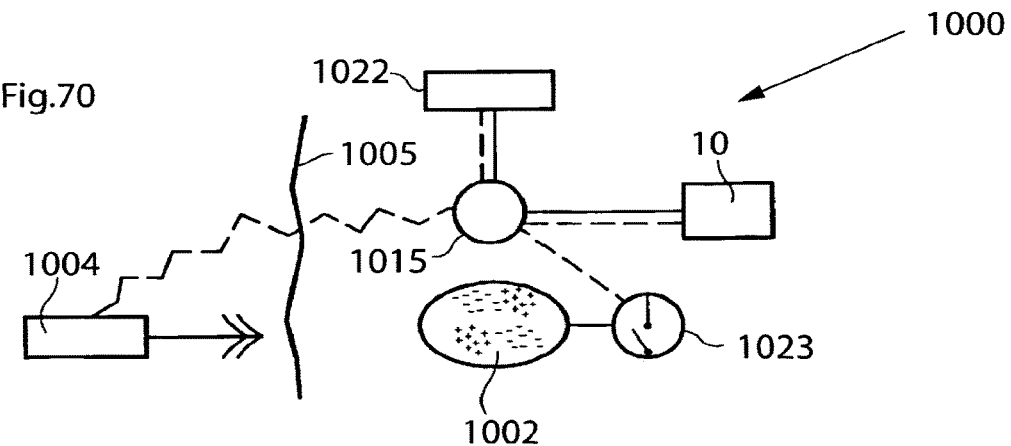

FIG. 70 shows an embodiment identical to that of FIG. 69, except that an internal control unit 1015 controllable by the wireless remote control of the external energy-transmission device 1004 also is implanted in the patient. In this case, the electric switch 1023 is operated by the energy supplied by the implanted energy-transforming device 1002 to switch from an off mode, in which the wireless remote control is prevented from controlling the internal control unit 1015 and the battery is not in use, to a standby mode, in which the remote control is permitted to control the internal control unit 1015 to release electric energy from the battery 1022 for the operation of the apparatus 10.

Figure 71:
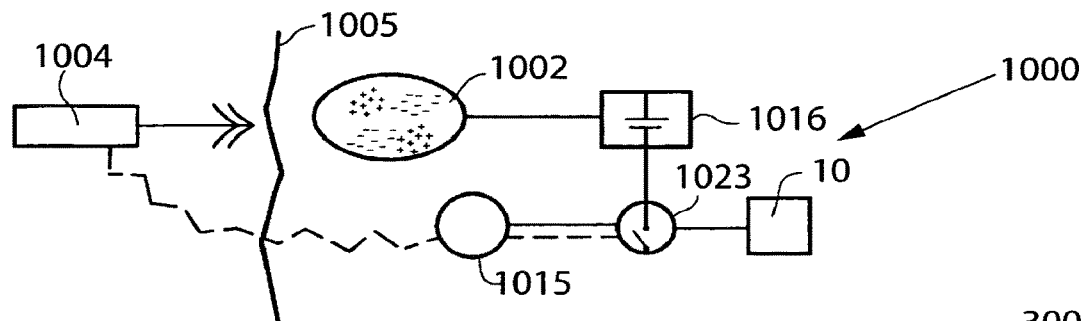

FIG. 71 shows an embodiment identical to that of FIG. 70, except that an accumulator 1016 is substituted for the battery 1022 and the implanted components are interconnected differently. In this case, the accumulator 1016 stores energy from the implanted energy-transforming device 1002. In response to a control signal from the wireless remote control of the external energy-transmission device 1004, the internal control unit 1015 controls the electric switch 1023 to switch from an off mode, in which the accumulator 1016 is not in use, to an on mode, in which the accumulator 1016 supplies energy for the operation of the apparatus 10. The accumulator may be combined with or replaced by a capacitor.

Figure 72:
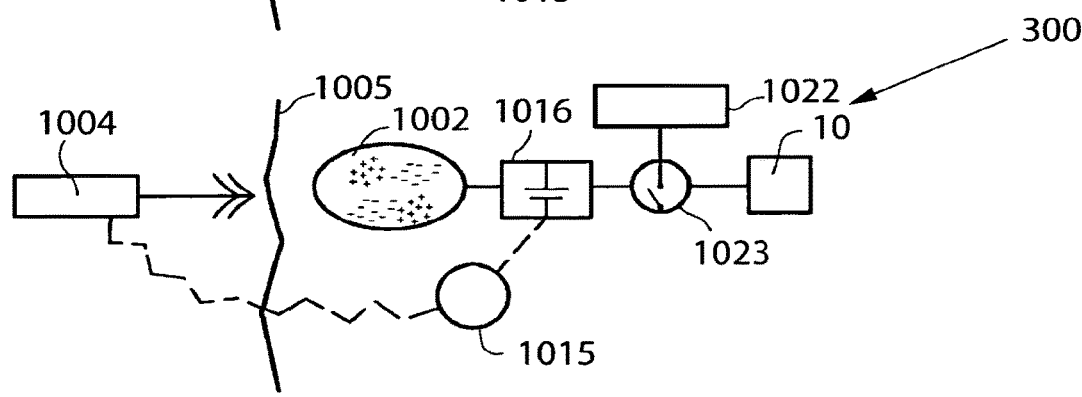

FIG. 72 shows an embodiment identical to that of FIG. 71, except that a battery 1022 also is implanted in the patient and the implanted components are interconnected differently. In response to a control signal from the wireless remote control of the external energy-transmission device 1004, the internal control unit 1015 controls the accumulator 1016 to deliver energy for operating the electric switch 1023 to switch from an off mode, in which the battery 1022 is not in use, to an on mode, in which the battery 1022 supplies electric energy for the operation of the apparatus 10.

Alternatively, the electric switch 1023 may be operated by energy supplied by the accumulator 1016 to switch from an off mode, in which the wireless remote control is prevented from controlling the battery 1022 to supply electric energy and is not in use, to a standby mode, in which the wireless remote control is permitted to control the battery 1022 to supply electric energy for the operation of the apparatus 10.

It should be understood that the switch 1023 and all other switches in this application should be interpreted in its broadest embodiment. This means a transistor, MCU, MCPU, ASIC, FPGA or a DA converter or any other electronic component or circuit that may switch the power on and off. Preferably the switch is controlled from outside the body, or alternatively by an implanted internal control unit.

Figure 73:
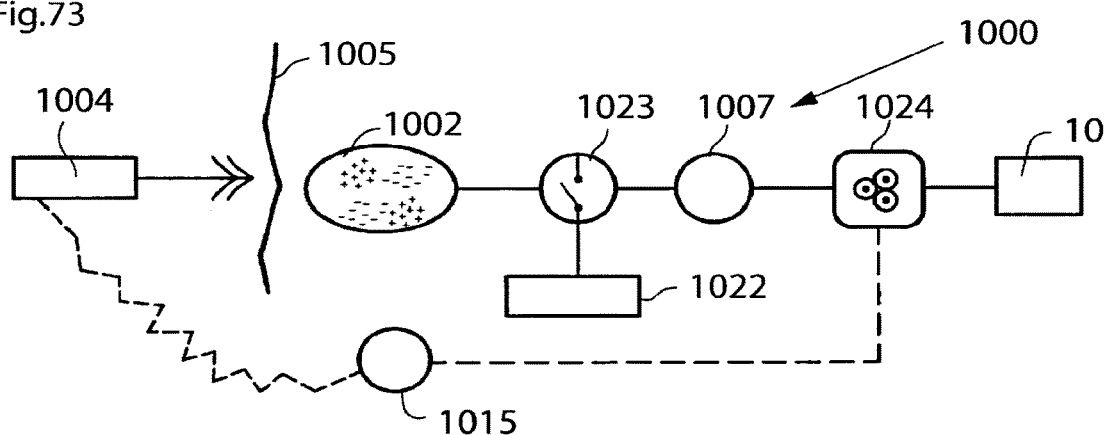

FIG. 73 shows an embodiment identical to that of FIG. 69, except that a motor 1007, a mechanical reversing device in the form of a gear box 1024, and an internal control unit 1015 for controlling the gear box 1024 also are implanted in the patient. The internal control unit 1015 controls the gear box 1024 to reverse the function performed by the apparatus 10 (mechanically operated). Even simpler is to switch the direction of the motor electronically. The gear box interpreted in its broadest embodiment may stand for a servo arrangement saving force for the operation device in favour of longer stroke to act.

Figure 74:
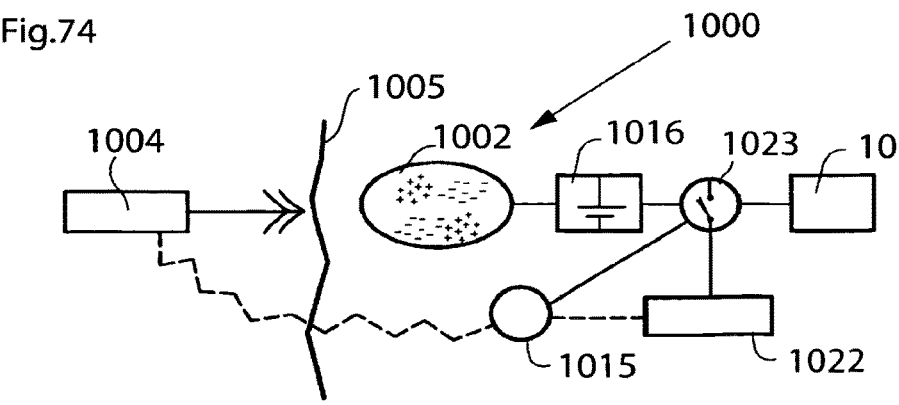

FIG. 74 shows an embodiment identical to that of FIG. 73 except that the implanted components are interconnected differently. Thus, in this case the internal control unit 1015 is powered by the battery 1022 when the accumulator 1016, suitably a capacitor, activates the electric switch 1023 to switch to an on mode. When the electric switch 1023 is in its on mode the internal control unit 1015 is permitted to control the battery 1022 to supply, or not supply, energy for the operation of the apparatus 10.

Figure 75:
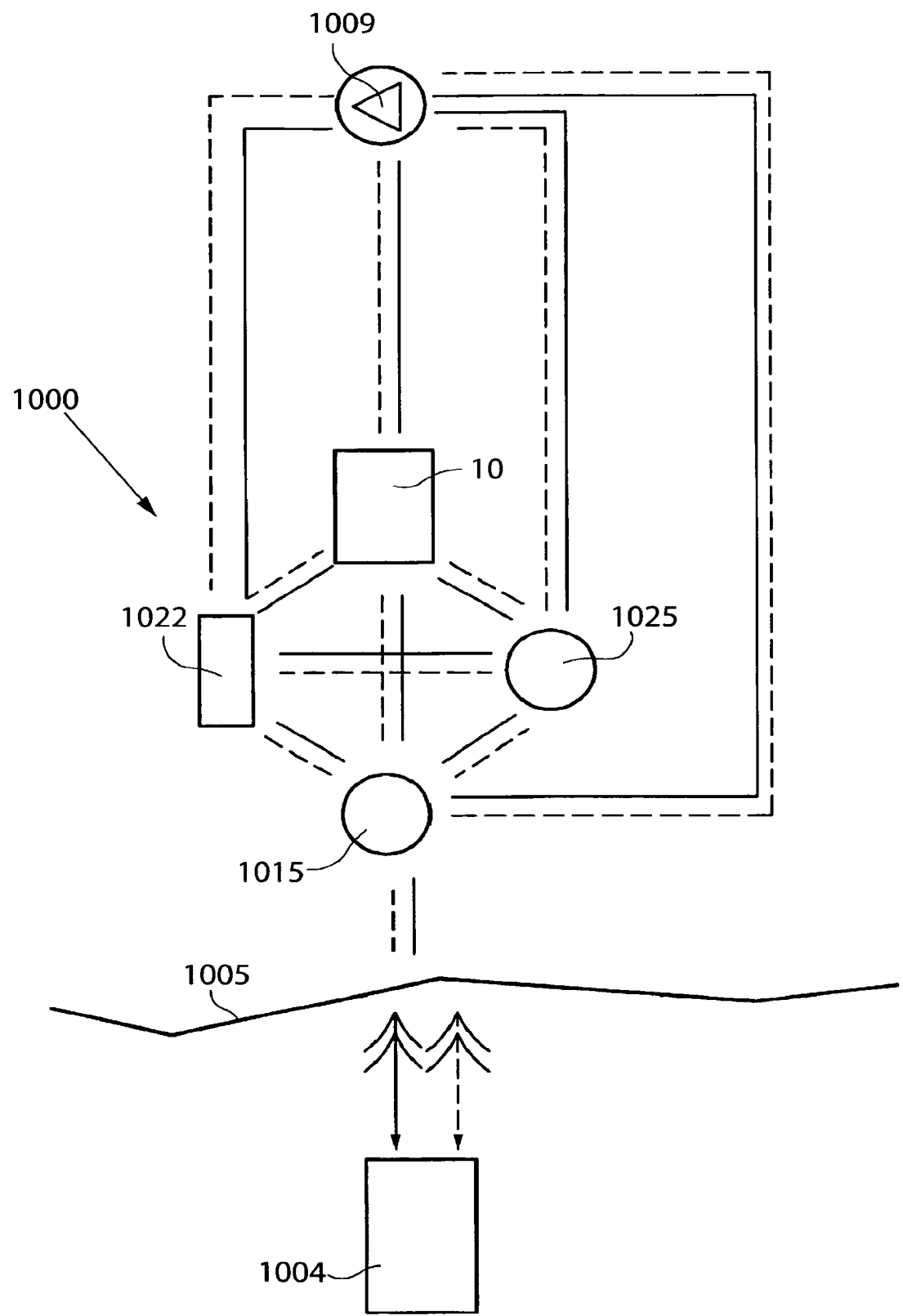

FIG. 75 schematically shows conceivable combinations of implanted components of the apparatus for achieving various communication options. Basically, there are the apparatus 10, the internal control unit 1015, motor or pump unit 1009, and the external energy-transmission device 1004 including the external wireless remote control. As already described above the wireless remote control transmits a control signal which is received by the internal control unit 1015, which in turn controls the various implanted components of the apparatus.

A feedback device, preferably comprising a sensor or measuring device 1025, may be implanted in the patient for sensing a physical parameter of the patient. The physical parameter may be at least one selected from the group consisting of pressure, volume, diameter, stretching, elongation, extension, movement, bending, elasticity, muscle contraction, nerve impulse, body temperature, blood pressure, blood flow, heartbeats and breathing. The sensor may sense any of the above physical parameters. For example, the sensor may be a pressure or motility sensor. Alternatively, the sensor 1025 may be arranged to sense a functional parameter. The functional parameter may be correlated to the transfer of energy for charging an implanted energy source and may further include at least one selected from the group of parameters consisting of; electricity, any electrical parameter, pressure, volume, diameter, stretch, elongation, extension, movement, bending, elasticity, temperature and flow.

The feedback may be sent to the internal control unit or out to an external control unit preferably via the internal control unit. Feedback may be sent out from the body via the energy transfer system or a separate communication system with receiver and transmitters.

The internal control unit 1015, or alternatively the external wireless remote control of the external energy-transmission device 1004, may control the apparatus 10 in response to signals from the sensor 1025. A transceiver may be combined with the sensor 1025 for sending information on the sensed physical parameter to the external wireless remote control. The wireless remote control may comprise a signal transmitter or transceiver and the internal control unit 1015 may comprise a signal receiver or transceiver. Alternatively, the wireless remote control may comprise a signal receiver or transceiver and the internal control unit 1015 may comprise a signal transmitter or transceiver. The above transceivers, transmitters and receivers may be used for sending information or data related to the apparatus 10 from inside the patient's body to the outside thereof.

Where the motor/pump unit 1009 and battery 1022 for powering the motor/pump unit 1009 are implanted, information related to the charging of the battery 1022 may be fed back. To be more precise, when charging a battery or accumulator with energy feed back information related to said charging process is sent and the energy supply is changed accordingly.

Figure 76:
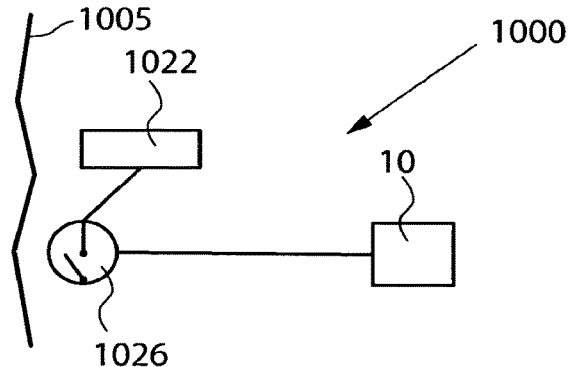

FIG. 76 shows an alternative embodiment wherein the apparatus 10 is regulated from outside the patient's body. The system 1000 comprises a battery 1022 connected to the apparatus 10 via a subcutaneous electric switch 1026. Thus, the regulation of the apparatus 10 is performed non-invasively by manually pressing the subcutaneous switch, whereby the operation of the apparatus 10 is switched on and off. It will be appreciated that the shown embodiment is a simplification and that additional components, such as an internal control unit or any other part disclosed in the present application can be added to the system. Two subcutaneous switches may also be used. In the preferred embodiment one implanted switch sends information to the internal control unit to perform a certain predetermined performance and when the patient press the switch again the performance is reversed.

Figure 77:
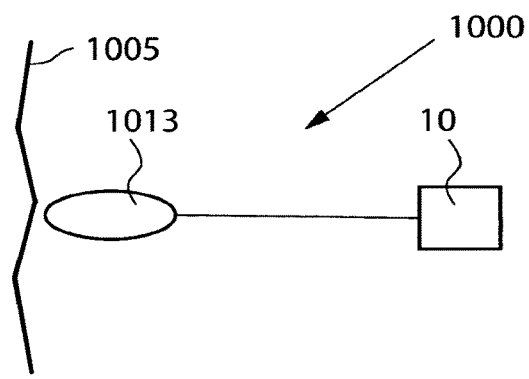

FIG. 77 shows an alternative embodiment, wherein the system 1000 comprises a hydraulic fluid reservoir 1013 hydraulically connected to the apparatus. Non-invasive regulation is performed by manually pressing the hydraulic reservoir connected to the apparatus.

The system may include an external data communicator and an implantable internal data communicator communicating with the external data communicator. The internal communicator feeds data related to the apparatus or the patient to the external data communicator and/or the external data communicator feeds data to the internal data communicator.

Figure 78:
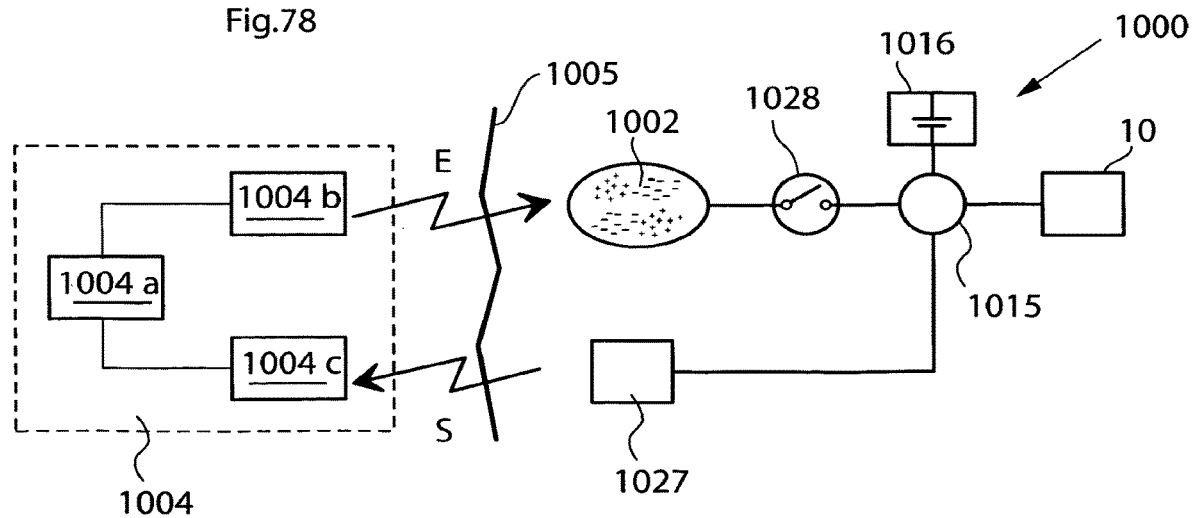
FIG. 78 is a schematic block diagram illustrating an arrangement for supplying an accurate amount of energy used for the operation of the apparatus shown in FIG. 1.

FIG. 78 schematically illustrates an arrangement of the system that is capable of sending information from inside the patient's body to the outside thereof to give feedback information related to at least one functional parameter of the apparatus or system, or related to a physical parameter of the patient, in order to supply an accurate amount of energy to an implanted internal energy receiver 1002 connected to implanted energy consuming components of the apparatus 10. Such an energy receiver 1002 may include an energy source and/or an energy-transforming device. Briefly described, wireless energy is transmitted from an external energy source 1004a located outside the patient and is received by the internal energy receiver 1002 located inside the patient. The internal energy receiver is adapted to directly or indirectly supply received energy to the energy consuming components of the apparatus 10 via a switch 1026. An energy balance is determined between the energy received by the internal energy receiver 1002 and the energy used for the apparatus 10, and the transmission of wireless energy is then controlled based on the determined energy balance. The energy balance thus provides an accurate indication of the correct amount of energy needed, which is sufficient to operate the apparatus 10 properly, but without causing undue temperature rise.

In FIG. 78 the patient's skin is indicated by a vertical line 1005. Here, the energy receiver comprises an energy-transforming device 1002 located inside the patient, preferably just beneath the patient's skin 1005. Generally speaking, the implanted energy-transforming device 1002 may be placed in the abdomen, thorax, muscle fascia (e.g. in the abdominal wall), subcutaneously, or at any other suitable location. The implanted energy-transforming device 1002 is adapted to receive wireless energy E transmitted from the external energy-source 1004a provided in an external energy-transmission device 1004 located outside the patient's skin 1005 in the vicinity of the implanted energy-transforming device 1002.

As is well known in the art, the wireless energy E may generally be transferred by means of any suitable Transcutaneous Energy Transfer (TET) device, such as a device including a primary coil arranged in the external energy source 1004a and an adjacent secondary coil arranged in the implanted energy-transforming device 1002. When an electric current is fed through the primary coil, energy in the form of a voltage is induced in the secondary coil which can be used to power the implanted energy consuming components of the apparatus, e.g. after storing the incoming energy in an implanted energy source, such as a rechargeable battery or a capacitor. However, the present invention is generally not limited to any particular energy transfer technique, TET devices or energy sources, and any kind of wireless energy may be used.

The amount of energy received by the implanted energy receiver may be compared with the energy used by the implanted components of the apparatus. The term "energy used" is then understood to include also energy stored by implanted components of the apparatus. A control device includes an external control unit 1004b that controls the external energy source 1004a based on the determined energy balance to regulate the amount of transferred energy. In order to transfer the correct amount of energy, the energy balance and the required amount of energy is determined by means of a determination device including an implanted internal control unit 1015 connected between the switch 1026 and the apparatus 10. The internal control unit 1015 may thus be arranged to receive various measurements obtained by suitable sensors or the like, not shown, measuring certain characteristics of the apparatus 10, somehow reflecting the required amount of energy needed for proper operation of the apparatus 10. Moreover, the current condition of the patient may also be detected by means of suitable measuring devices or sensors, in order to provide parameters reflecting the patient's condition. Hence, such characteristics and/or parameters may be related to the current state of the apparatus 10, such as power consumption, operational mode and temperature, as well as the patient's condition reflected by parameters such as; body temperature, blood pressure, heartbeats and breathing. Other kinds of physical parameters of the patient and functional parameters of the device are described elsewhere.

Furthermore, an energy source in the form of an accumulator 1016 may optionally be connected to the implanted energy-transforming device 1002 via the control unit 1015 for accumulating received energy for later use by the apparatus 10. Alternatively or additionally, characteristics of such an accumulator, also reflecting the required amount of energy, may be measured as well. The accumulator may be replaced by a rechargeable battery, and the measured characteristics may be related to the current state of the battery, any electrical parameter such as energy consumption voltage, temperature, etc. In order to provide sufficient voltage and current to the apparatus 10, and also to avoid excessive heating, it is clearly understood that the battery should be charged optimally by receiving a correct amount of energy from the implanted energy-transforming device 1002, i.e. not too little or too much. The accumulator may also be a capacitor with corresponding characteristics.

For example, battery characteristics may be measured on a regular basis to determine the current state of the battery, which then may be stored as state information in a suitable storage means in the internal control unit 1015. Thus, whenever new measurements are made, the stored battery state information can be updated accordingly. In this way, the state of the battery can be "calibrated" by transferring a correct amount of energy, so as to maintain the battery in an optimal condition.

Thus, the internal control unit 1015 of the determination device is adapted to determine the energy balance and/or the currently required amount of energy, (either energy per time unit or accumulated energy) based on measurements made by the above-mentioned sensors or measuring devices of the apparatus 10, or the patient, or an implanted energy source if used, or any combination thereof. The internal control unit 1015 is further connected to an internal signal transmitter 1027, arranged to transmit a control signal reflecting the determined required amount of energy, to an external signal receiver 1004c connected to the external control unit 1004b. The amount of energy transmitted from the external energy source 1004a may then be regulated in response to the received control signal.

Alternatively, the determination device may include the external control unit 1004b. In this alternative, sensor measurements can be transmitted directly to the external control unit 1004b wherein the energy balance and/or the currently required amount of energy can be determined by the external control unit 1004*b*, thus integrating the above-described function of the internal control unit 1015 in the external control unit 1004*b*. In that case, the internal control unit 1015 can be omitted and the sensor measurements are supplied directly to the internal signal transmitter 1027 which sends the measurements over to the external signal receiver 1004*c* and the external control unit 1004*b*. The energy balance and the currently required amount of energy can then be determined by the external control unit 1004*b* based on those sensor measurements.

Hence, the present solution according to the arrangement of FIG. 78 employs the feed back of information indicating the required energy, which is more efficient than previous solutions because it is based on the actual use of energy that is compared to the received energy, e.g. with respect to the amount of energy, the energy difference, or the energy receiving rate as compared to the energy rate used by implanted energy consuming components of the apparatus. The apparatus may use the received energy either for consuming or for storing the energy in an implanted energy source or the like. The different parameters discussed above would thus be used if relevant and needed and then as a tool for determining the actual energy balance. However, such parameters may also be needed per se for any actions taken internally to specifically operate the apparatus.

The internal signal transmitter 1027 and the external signal receiver 1004*c* may be implemented as separate units using suitable signal transfer means, such as radio, IR (Infrared) or ultrasonic signals. Alternatively, the internal signal transmitter 1027 and the external signal receiver 1004*c* may be integrated in the implanted energy-transforming device 1002 and the external energy source 1004*a*, respectively, so as to convey control signals in a reverse direction relative to the energy transfer, basically using the same transmission technique. The control signals may be modulated with respect to frequency, phase or amplitude.

Thus, the feedback information may be transferred either by a separate communication system including receivers and transmitters or may be integrated in the energy system. In accordance, such an integrated information feedback and energy system comprises an implantable internal energy receiver for receiving wireless energy, the energy receiver having an internal first coil and a first electronic circuit connected to the first coil, and an external energy transmitter for transmitting wireless energy, the energy transmitter having an external second coil and a second electronic circuit connected to the second coil. The external second coil of the energy transmitter transmits wireless energy which is received by the first coil of the energy receiver. This system further comprises a power switch for switching the connection of the internal first coil to the first electronic circuit on and off, such that feedback information related to the charging of the first coil is received by the external energy transmitter in the form of an impedance variation in the load of the external second coil, when the power switch switches the connection of the internal first coil to the first electronic circuit on and off. In implementing this system in the arrangement of FIG. 78, the switch 1026 is either separate and controlled by the internal control unit 1015, or integrated in the internal control unit 1015. It should be understood that the switch 1026 should be interpreted in its broadest embodiment. This means a transistor, MCU, MCPU, ASIC FPGA or a DA converter or any other electronic component or circuit that may switch the power on and off.

To conclude, the energy supply arrangement illustrated in FIG. 78 may operate basically in the following manner. The energy balance is first determined by the internal control unit 1015 of the determination device. A control signal reflecting the required amount of energy is also created by the internal control unit 1015, and the control signal is transmitted from the internal signal transmitter 1027 to the external signal receiver 1004*c*. Alternatively, the energy balance can be determined by the external control unit 1004*b* instead depending on the implementation, as mentioned above. In that case, the control signal may carry measurement results from various sensors. The amount of energy emitted from the external energy source 1004*a* can then be regulated by the external control unit 1004*b*, based on the determined energy balance, e.g. in response to the received control signal. This process may be repeated intermittently at certain intervals during ongoing energy transfer, or may be executed on a more or less continuous basis during the energy transfer.

The amount of transferred energy can generally be regulated by adjusting various transmission parameters in the external energy source 1004*a*, such as voltage, current, amplitude, wave frequency and pulse characteristics.

This system may also be used to obtain information about the coupling factors between the coils in a TET system even to calibrate the system both to find an optimal place for the external coil in relation to the internal coil and to optimize energy transfer. Simply comparing in this case the amount of energy transferred with the amount of energy received. For example if the external coil is moved the coupling factor may vary and correctly displayed movements could cause the external coil to find the optimal place for energy transfer. Preferably, the external coil is adapted to calibrate the amount of transferred energy to achieve the feedback information in the determination device, before the coupling factor is maximized.

This coupling factor information may also be used as a feedback during energy transfer. In such a case, the energy system comprises an implantable internal energy receiver for receiving wireless energy, the energy receiver having an internal first coil and a first electronic circuit connected to the first coil, and an external energy transmitter for transmitting wireless energy, the energy transmitter having an external second coil and a second electronic circuit connected to the second coil. The external second coil of the energy transmitter transmits wireless energy which is received by the first coil of the energy receiver. This system further comprises a feedback device for communicating out the amount of energy received in the first coil as a feedback information, and wherein the second electronic circuit includes a determination device for receiving the feedback information and for comparing the amount of transferred energy by the second coil with the feedback information related to the amount of energy received in the first coil to obtain the coupling factor between the first and second coils. The energy transmitter may regulate the transmitted energy in response to the obtained coupling factor.

Figure 79:
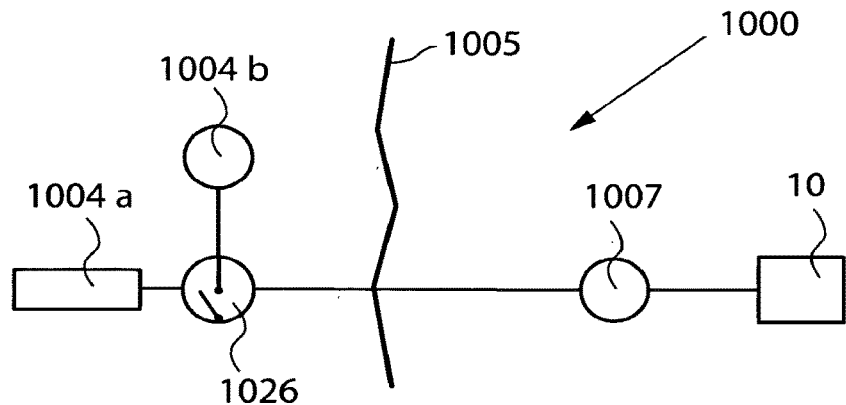
FIG. 79 schematically shows an embodiment of the system, in which the apparatus is operated with wire bound energy.

With reference to FIG. 79, although wireless transfer of energy for operating the apparatus has been described above to enable non-invasive operation, it will be appreciated that the apparatus can be operated with wire bound energy as well. Such an example is shown in FIG. 79, wherein an external switch 1026 is interconnected between the external energy source 1004*a* and an operation device, such as an electric motor 1007 operating the apparatus 10. An external control unit 1004*b* controls the operation of the external switch 1026 to effect proper operation of the apparatus 10.

Figure 80:
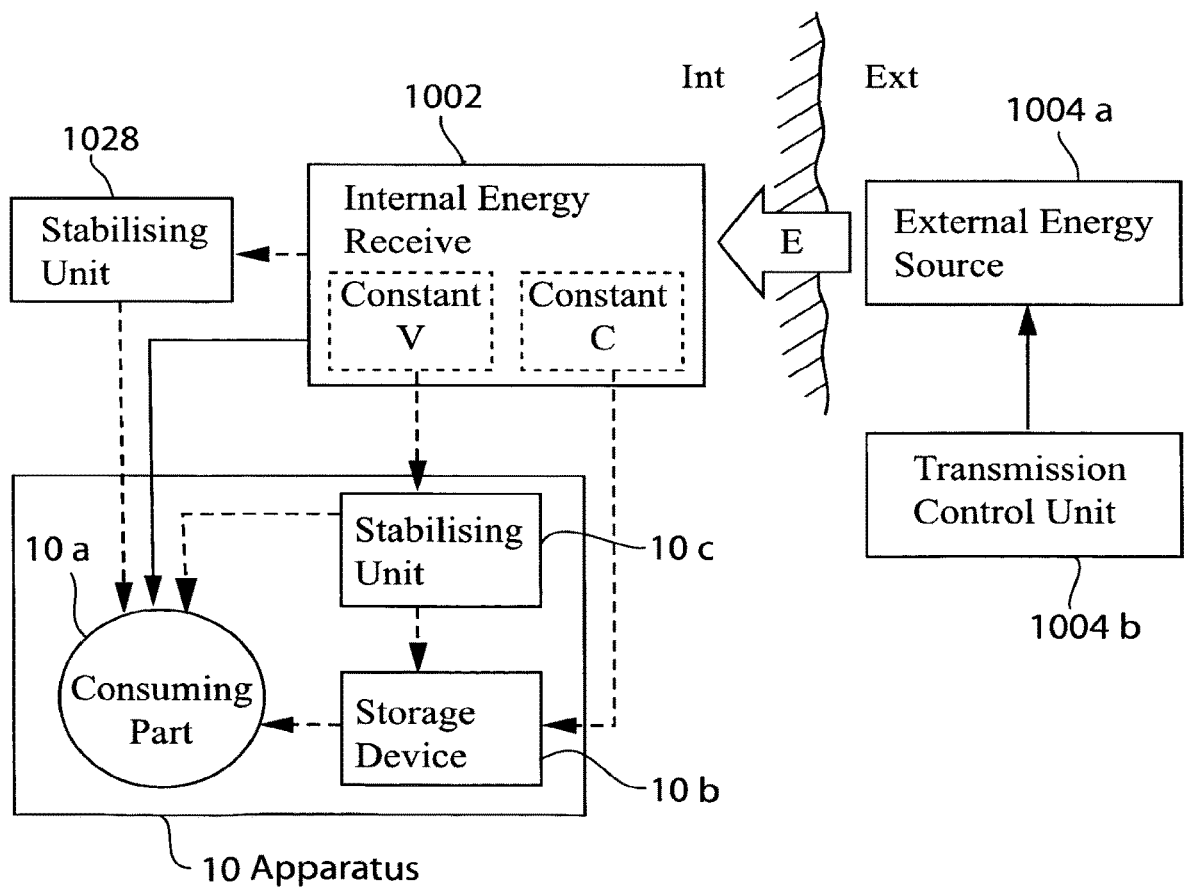
FIG. 80 is a more detailed block diagram of an arrangement for controlling the transmission of wireless energy used for the operation of the apparatus shown in FIG. 1.

FIG. 80 illustrates different embodiments for how received energy can be supplied to and used by the apparatus 10. Similar to the example of FIG. 78, an internal energy receiver 1002 receives wireless energy E from an external energy source 1004a which is controlled by a transmission control unit 1004b. The internal energy receiver 1002 may comprise a constant voltage circuit, indicated as a dashed box "constant V" in the figure, for supplying energy at constant voltage to the apparatus 10. The internal energy receiver 1002 may further comprise a constant current circuit, indicated as a dashed box "constant C" in the figure, for supplying energy at constant current to the apparatus 10.

The apparatus 10 comprises an energy consuming part 10a, which may be a motor, pump, restriction device, or any other medical appliance that requires energy for its electrical operation. The apparatus 10 may further comprise an energy storage device 10b for storing energy supplied from the internal energy receiver 1002. Thus, the supplied energy may be directly consumed by the energy consuming part 10a, or stored by the energy storage device 10b, or the supplied energy may be partly consumed and partly stored. The apparatus 10 may further comprise an energy stabilizing unit 10c for stabilizing the energy supplied from the internal energy receiver 1002. Thus, the energy may be supplied in a fluctuating manner such that it may be necessary to stabilize the energy before consumed or stored.

The energy supplied from the internal energy receiver 1002 may further be accumulated and/or stabilized by a separate energy stabilizing unit 1028 located outside the apparatus 10, before being consumed and/or stored by the apparatus 10. Alternatively, the energy stabilizing unit 1028 may be integrated in the internal energy receiver 1002. In either case, the energy stabilizing unit 1028 may comprise a constant voltage circuit and/or a constant current circuit.

It should be noted that FIG. 78 and FIG. 80 illustrate some possible but non-limiting implementation options regarding how the various shown functional components and elements can be arranged and connected to each other. However, the skilled person will readily appreciate that many variations and modifications can be made within the scope.

Figure 81:
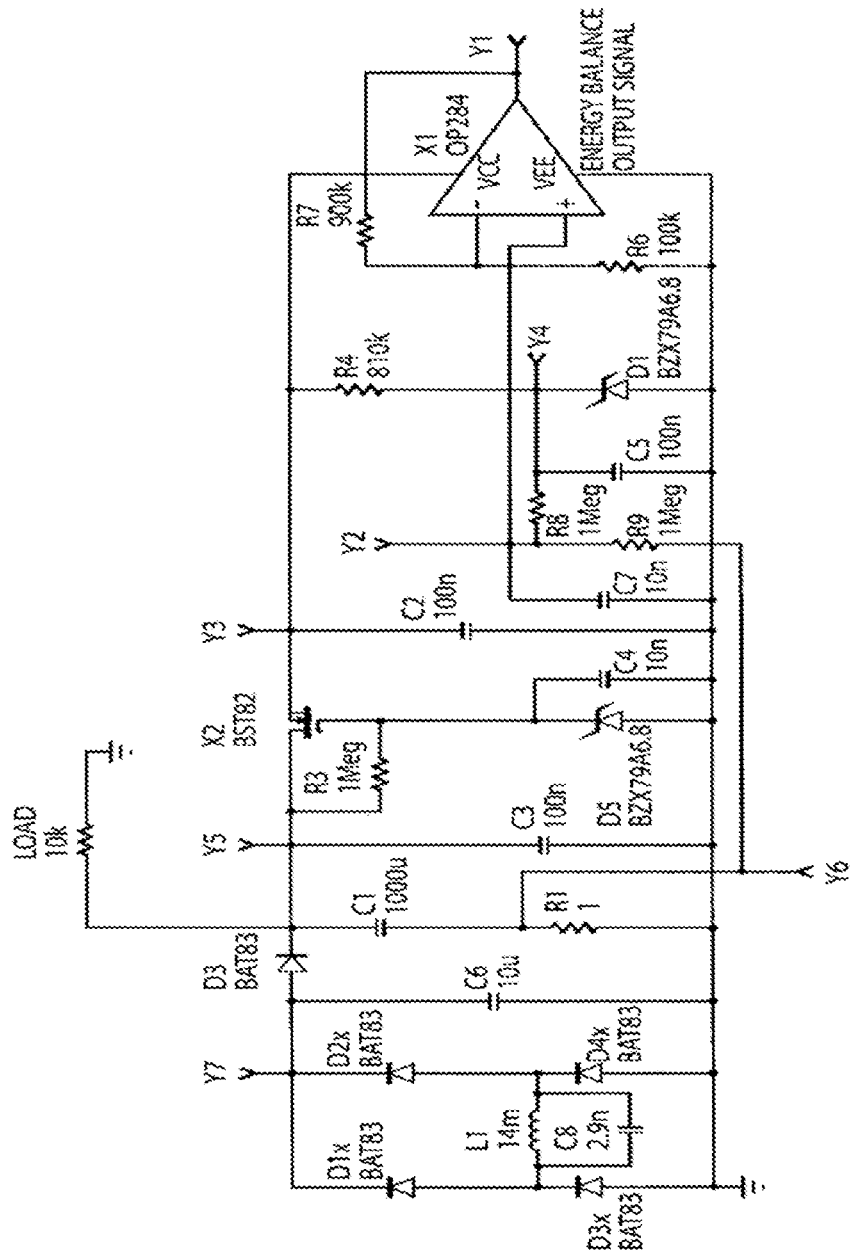
FIG. 81 is a circuit for the arrangement shown in FIG. 62, according to a possible implementation example.

FIG. 81 schematically shows an energy balance measuring circuit of one of the proposed designs of the system for controlling transmission of wireless energy, or energy balance control system. The circuit has an output signal centered on 2.5V and proportionally related to the energy imbalance. The derivative of this signal shows if the value goes up and down and how fast such a change takes place. If the amount of received energy is lower than the energy used by implanted components of the apparatus, more energy is transferred and thus charged into the energy source. The output signal from the circuit is typically feed to an A/D converter and converted into a digital format. The digital information can then be sent to the external energy-transmission device allowing it to adjust the level of the transmitted energy. Another possibility is to have a completely analog system that uses comparators comparing the energy balance level with certain maximum and minimum thresholds sending information to external energy-transmission device if the balance drifts out of the max/min window.

The schematic FIG. 81 shows a circuit implementation for a system that transfers energy to the implanted energy components of the apparatus from outside of the patient's body using inductive energy transfer. An inductive energy transfer system typically uses an external transmitting coil and an internal receiving coil. The receiving coil, L1, is included in the schematic FIG. 64; the transmitting parts of the system are excluded.

The implementation of the general concept of energy balance and the way the information is transmitted to the external energy transmitter can of course be implemented in numerous different ways. The schematic FIG. 81 and the above described method of evaluating and transmitting the information should only be regarded as examples of how to implement the control system.

Circuit Details

In FIG. 81 the symbols Y1, Y2, Y3 and so on symbolize test points within the circuit. The components in the diagram and their respective values are values that work in this particular implementation which of course is only one of an infinite number of possible design solutions.

Energy to power the circuit is received by the energy receiving coil L1. Energy to implanted components is transmitted in this particular case at a frequency of 25 kHz. The energy balance output signal is present at test point Y1.

Those skilled in the art will realize that the above various embodiments of the system could be combined in many different ways. For example, the electric switch 1006 of FIG. 64 could be incorporated in any of the embodiments of FIGS. 67-73, the hydraulic valve shifting device 1014 of FIG. 67 could be incorporated in the embodiment of FIG. 66, and the gear box 1024 could be incorporated in the embodiment of FIG. 65. Please observe that the switch simply could mean any electronic circuit or component.

The embodiments described in connection with FIGS. 78, 80 and 81 identify a method and a system for controlling transmission of wireless energy to implanted energy consuming components of an electrically operable apparatus. Such a method and system will be defined in general terms in the following.

A method is thus provided for controlling transmission of wireless energy supplied to implanted energy consuming components of an apparatus as described above. The wireless energy E is transmitted from an external energy source located outside the patient and is received by an internal energy receiver located inside the patient, the internal energy receiver being connected to the implanted energy consuming components of the apparatus for directly or indirectly supplying received energy thereto. An energy balance is determined between the energy received by the internal energy receiver and the energy used for the apparatus. The transmission of wireless energy E from the external energy source is then controlled based on the determined energy balance.

The wireless energy may be transmitted inductively from a primary coil in the external energy source to a secondary coil in the internal energy receiver. A change in the energy balance may be detected to control the transmission of wireless energy based on the detected energy balance change. A difference may also be detected between energy received by the internal energy receiver and energy used for the medical device, to control the transmission of wireless energy based on the detected energy difference.

When controlling the energy transmission, the amount of transmitted wireless energy may be decreased if the detected energy balance change implies that the energy balance is increasing, or vice versa. The decrease/increase of energy transmission may further correspond to a detected change rate.

The amount of transmitted wireless energy may further be decreased if the detected energy difference implies that the received energy is greater than the used energy, or vice versa. The decrease/increase of energy transmission may then correspond to the magnitude of the detected energy difference.

As mentioned above, the energy used for the medical device may be consumed to operate the medical device, and/or stored in at least one energy storage device of the medical device.

When electrical and/or physical parameters of the medical device and/or physical parameters of the patient are determined, the energy may be transmitted for consumption and storage according to a transmission rate per time unit which is determined based on said parameters. The total amount of transmitted energy may also be determined based on said parameters.

When a difference is detected between the total amount of energy received by the internal energy receiver and the total amount of consumed and/or stored energy, and the detected difference is related to the integral over time of at least one measured electrical parameter related to said energy balance, the integral may be determined for a monitored voltage and/or current related to the energy balance.

When the derivative is determined over time of a measured electrical parameter related to the amount of consumed and/or stored energy, the derivative may be determined for a monitored voltage and/or current related to the energy balance.

The transmission of wireless energy from the external energy source may be controlled by applying to the external energy source electrical pulses from a first electric circuit to transmit the wireless energy, the electrical pulses having leading and trailing edges, varying the lengths of first time intervals between successive leading and trailing edges of the electrical pulses and/or the lengths of second time intervals between successive trailing and leading edges of the electrical pulses, and transmitting wireless energy, the transmitted energy generated from the electrical pulses having a varied power, the varying of the power depending on the lengths of the first and/or second time intervals.

In that case, the frequency of the electrical pulses may be substantially constant when varying the first and/or second time intervals. When applying electrical pulses, the electrical pulses may remain unchanged, except for varying the first and/or second time intervals. The amplitude of the electrical pulses may be substantially constant when varying the first and/or second time intervals. Further, the electrical pulses may be varied by only varying the lengths of first time intervals between successive leading and trailing edges of the electrical pulses.

A train of two or more electrical pulses may be supplied in a row, wherein when applying the train of pulses, the train having a first electrical pulse at the start of the pulse train and having a second electrical pulse at the end of the pulse train, two or more pulse trains may be supplied in a row, wherein the lengths of the second time intervals between successive trailing edge of the second electrical pulse in a first pulse train and leading edge of the first electrical pulse of a second pulse train are varied.

When applying the electrical pulses, the electrical pulses may have a substantially constant current and a substantially constant voltage. The electrical pulses may also have a substantially constant current and a substantially constant voltage. Further, the electrical pulses may also have a substantially constant frequency. The electrical pulses within a pulse train may likewise have a substantially constant frequency.

The circuit formed by the first electric circuit and the external energy source may have a first characteristic time period or first time constant, and when effectively varying the transmitted energy, such frequency time period may be in the range of the first characteristic time period or time constant or shorter.

A system comprising an apparatus as described above is thus also provided for controlling transmission of wireless energy supplied to implanted energy consuming components of the apparatus. In its broadest sense, the system comprises a control device for controlling the transmission of wireless energy from an energy-transmission device, and an implantable internal energy receiver for receiving the transmitted wireless energy, the internal energy receiver being connected to implantable energy consuming components of the apparatus for directly or indirectly supplying received energy thereto. The system further comprises a determination device adapted to determine an energy balance between the energy received by the internal energy receiver and the energy used for the implantable energy consuming components of the apparatus, wherein the control device controls the transmission of wireless energy from the external energy-transmission device, based on the energy balance determined by the determination device.

Further, the system may comprise any of the following:

A primary coil in the external energy source adapted to transmit the wireless energy inductively to a secondary coil in the internal energy receiver.

The determination device is adapted to detect a change in the energy balance, and the control device controls the transmission of wireless energy based on the detected energy balance change The determination device is adapted to detect a difference between energy received by the internal energy receiver and energy used for the implantable energy consuming components of the apparatus, and the control device controls the transmission of wireless energy based on the detected energy difference.

The control device controls the external energy-transmission device to decrease the amount of transmitted wireless energy if the detected energy balance change implies that the energy balance is increasing, or vice versa, wherein the decrease/increase of energy transmission corresponds to a detected change rate.

The control device controls the external energy-transmission device to decrease the amount of transmitted wireless energy if the detected energy difference implies that the received energy is greater than the used energy, or vice versa, wherein the decrease/increase of energy transmission corresponds to the magnitude of said detected energy difference.

The energy used for the apparatus is consumed to operate the apparatus, and/or stored in at least one energy storage device of the apparatus.

Where electrical and/or physical parameters of the apparatus and/or physical parameters of the patient are determined, the energy-transmission device transmits the energy for consumption and storage according to a transmission rate per time unit which is determined by the determination device based on said parameters. The determination device also determines the total amount of transmitted energy based on said parameters.

When a difference is detected between the total amount of energy received by the internal energy receiver and the total amount of consumed and/or stored energy, and the detected difference is related to the integral over time of at least one measured electrical parameter related to the energy balance, the determination device determines the integral for a monitored voltage and/or current related to the energy balance.

When the derivative is determined over time of a measured electrical parameter related to the amount of consumed and/or stored energy, the determination device determines the derivative for a monitored voltage and/or current related to the energy balance.

The energy-transmission device comprises a coil placed externally to the human body, and an electric circuit is provided to power the external coil with electrical pulses to transmit the wireless energy. The electrical pulses have leading and trailing edges, and the electric circuit is adapted to vary first time intervals between successive leading and trailing edges and/or second time intervals between successive trailing and leading edges of the electrical pulses to vary the power of the transmitted wireless energy. As a result, the energy receiver receiving the transmitted wireless energy has a varied power.

The electric circuit is adapted to deliver the electrical pulses to remain unchanged except varying the first and/or second time intervals.

The electric circuit has a time constant and is adapted to vary the first and second time intervals only in the range of the first time constant, so that when the lengths of the first and/or second time intervals are varied, the transmitted power over the coil is varied.

The electric circuit is adapted to deliver the electrical pulses to be varied by only varying the lengths of first time intervals between successive leading and trailing edges of the electrical pulses.

The electric circuit is adapted to supplying a train of two or more electrical pulses in a row, said train having a first electrical pulse at the start of the pulse train and having a second electrical pulse at the end of the pulse train, and the lengths of the second time intervals between successive trailing edge of the second electrical pulse in a first pulse train and leading edge of the first electrical pulse of a second pulse train are varied by the first electronic circuit.

The electric circuit is adapted to provide the electrical pulses as pulses having a substantially constant height and/or amplitude and/or intensity and/or voltage and/or current and/or frequency.

The electric circuit has a time constant, and is adapted to vary the first and second time intervals only in the range of the first time constant, so that when the lengths of the first and/or second time intervals are varied, the transmitted power over the first coil are varied.

The electric circuit is adapted to provide the electrical pulses varying the lengths of the first and/or the second time intervals only within a range that includes the first time constant or that is located relatively close to the first time constant, compared to the magnitude of the first time constant.

FIGS. 82-85 show in more detail block diagrams of four different ways of hydraulically or pneumatically powering an implanted apparatus.

Figure 82:
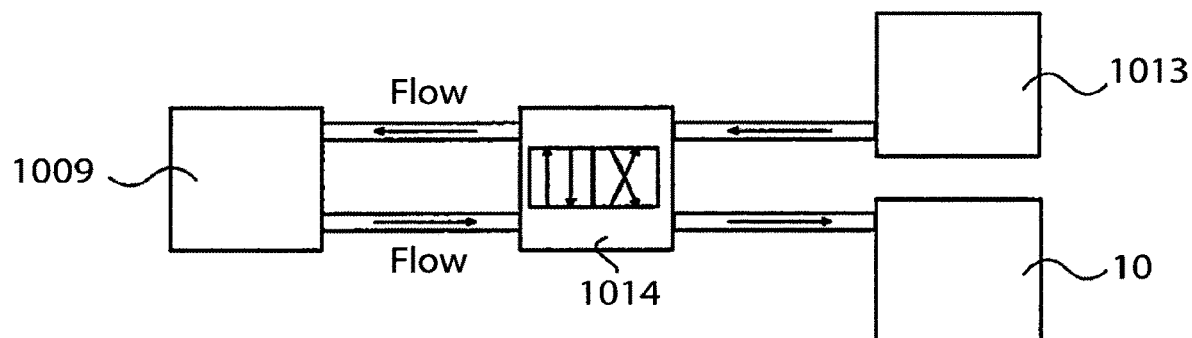

FIG. 82 shows a system as described above with. The system comprises an implanted apparatus 10 and further a separate regulation reservoir 1013, a one way pump 1009 and an alternate valve 1014.

Figure 83:
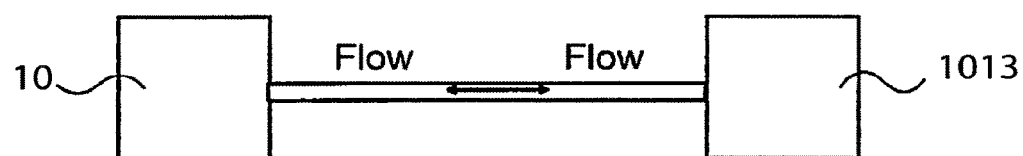

FIG. 83 shows the apparatus 10 and a fluid reservoir 1013. By moving the wall of the regulation reservoir or changing the size of the same in any other different way, the adjustment of the apparatus may be performed without any valve, just free passage of fluid any time by moving the reservoir wall.

Figure 84:
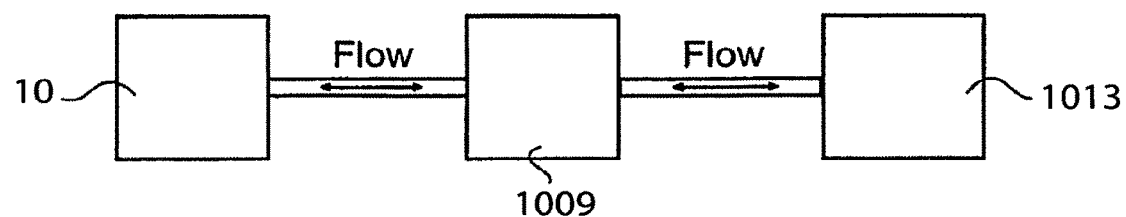
Figure 87:
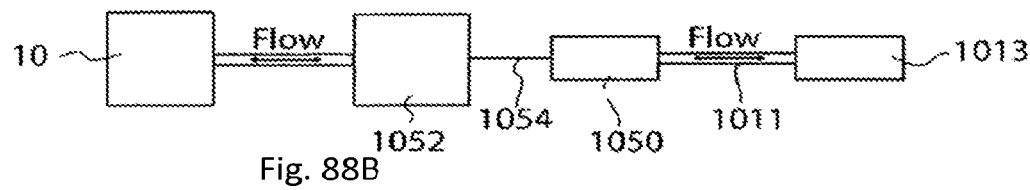

FIG. 84 shows the apparatus 10, a two-way pump 1009 and the regulation reservoir 1013.

FIG. 85 shows a block diagram of a reversed servo system with a first closed system controlling a second closed system. The servo system comprises a regulation reservoir 1013 and a servo reservoir 1050. The servo reservoir 1050 mechanically controls an implanted apparatus 10 via a mechanical interconnection 1054. The apparatus has an expandable/contactable cavity. This cavity is preferably expanded or contracted by supplying hydraulic fluid from the larger adjustable reservoir 1052 in fluid connection with the apparatus 10. Alternatively, the cavity contains compressible gas, which can be compressed and expanded under the control of the servo reservoir 1050.

The servo reservoir 1050 can also be part of the apparatus itself.

In one embodiment, the regulation reservoir is placed subcutaneous under the patient's skin and is operated by pushing the outer surface thereof by means of a finger. This system is illustrated in FIGS. 86a-c. In FIG. 86a, a flexible subcutaneous regulation reservoir 1013 is shown connected to a bulge shaped servo reservoir 1050 by means of a conduit 1011. This bellow shaped servo reservoir 1050 is comprised in a flexible apparatus 10. In the state shown in FIG. 86a, the servo reservoir 1050 contains a minimum of fluid and most fluid is found in the regulation reservoir 1013. Due to the mechanical interconnection between the servo reservoir 1050 and the apparatus 10, the outer shape of the apparatus 10 is contracted, i.e., it occupies less than its maximum volume. This maximum volume is shown with dashed lines in the figure.

FIG. 86b shows a state wherein a user, such as the patient in with the apparatus is implanted, presses the regulation reservoir 1013 so that fluid contained therein is brought to flow through the conduit 1011 and into the servo reservoir 1050, which, thanks to its bellow shape, expands longitudinally. This expansion in turn expands the apparatus 10 so that it occupies its maximum volume, thereby stretching the stomach wall (not shown), which it contacts.

The regulation reservoir 1013 is preferably provided with means 1013a for keeping its shape after compression. This means, which is schematically shown in the figure, will thus keep the apparatus 10 in a stretched position also when the user releases the regulation reservoir. In this way, the regulation reservoir essentially operates as an on/off switch for the system.

An alternative embodiment of hydraulic or pneumatic operation will now be described with reference to FIGS. 87 and 88a-c. The block diagram shown in FIG. 87 comprises with a first closed system controlling a second closed system. The first system comprises a regulation reservoir 1013 and a servo reservoir 1050. The servo reservoir 1050 mechanically controls a larger adjustable reservoir 1052 via a mechanical interconnection 1054. An implanted apparatus 10 having an expandable/contactable cavity is in turn controlled by the larger adjustable reservoir 1052 by supply of hydraulic fluid from the larger adjustable reservoir 1052 in fluid connection with the apparatus 10.

Figure 88A:
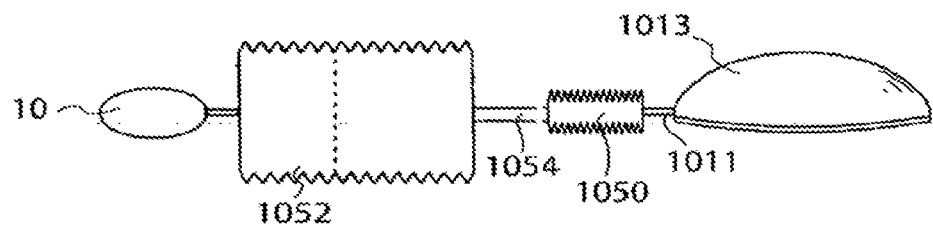
Figure 88B:
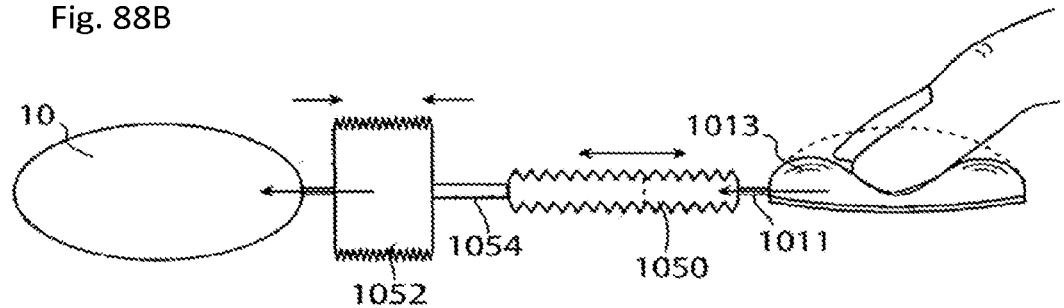
Figure 88C:
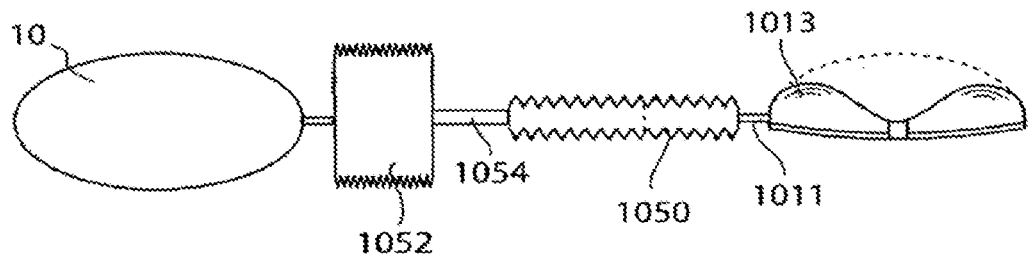

An example of this embodiment will now be described with reference to FIG. 88a-c. Like in the previous embodiment, the regulation reservoir is placed subcutaneous under the patient's skin and is operated by pushing the outer surface thereof by means of a finger. The regulation reservoir 1013 is in fluid connection with a bellow shaped servo reservoir 1050 by means of a conduit 1011. In the first closed system 1013, 1011, 1050 shown in FIG. 88a, the servo reservoir 1050 contains a minimum of fluid and most fluid is found in the regulation reservoir 1013.

The servo reservoir 1050 is mechanically connected to a larger adjustable reservoir 1052, in this example also having a bellow shape but with a larger diameter than the servo reservoir 1050. The larger adjustable reservoir 1052 is in fluid connection with the apparatus 10. This means that when a user pushes the regulation reservoir 1013, thereby displacing fluid from the regulation reservoir 1013 to the servo reservoir 1050, the expansion of the servo reservoir 1050 will displace a larger volume of fluid from the larger adjustable reservoir 1052 to the apparatus 10. In other words, in this reversed servo, a small volume in the regulation reservoir is compressed with a higher force and this creates a movement of a larger total area with less force per area unit.

Like in the previous embodiment described above with reference to FIGS. 86a-c, the regulation reservoir 1013 is preferably provided with means 1013a for keeping its shape after compression. This means, which is schematically shown in the figure, will thus keep the apparatus 10 in a stretched position also when the user releases the regulation reservoir. In this way, the regulation reservoir essentially operates as an on/off switch for the system.

Figure 89A:
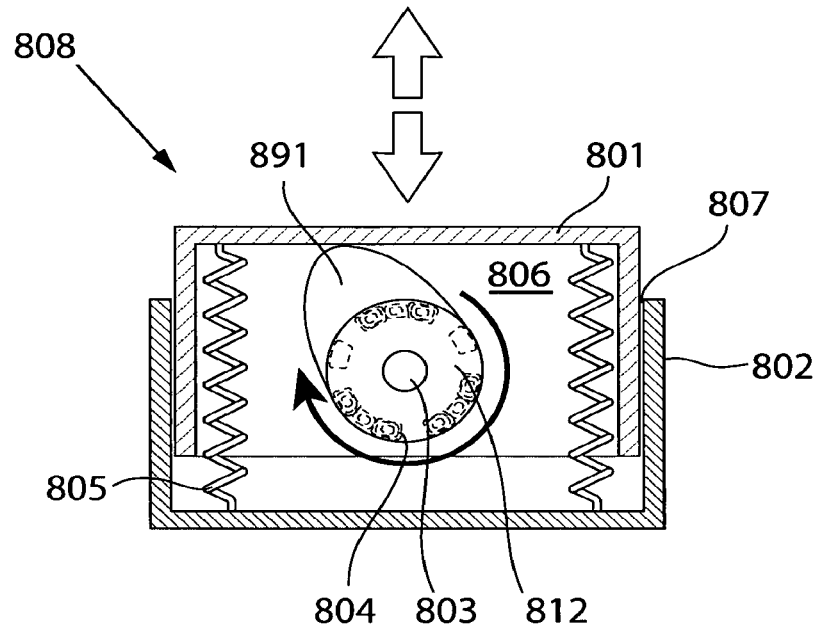
FIG. 89a shows a sealed chamber comprising an operating device.

FIG. 89a shows an embodiment of the implantable device, wherein the implantable device comprises an eccentrically rotating member 891, being a driving member, being a part of an operation device having a rotating centre 803. The operation device further comprises an embodiment of a magnetic motor, such as the magnetic motor described with reference to FIGS. 7 and 8 comprising coils 804 and magnets in magnetic connection with said coils 804. The coils 804 are placed on a first plate 812 which is in connection with a second plate 891 comprising the magnets. In the embodiment shown in FIG. 89a, the second plate 891 comprises the eccentrically rotating member 891. The first 812 and second 891 plates are adapted to be rotationally displaceable in relation to each other, and a force is created by successive energizing of the coils 804 in magnetic connection with the magnets, which creates a rotational movement of the first plate 812 in relation to the second plate 891 which in turn affects the eccentrically rotating member 891. Further, according to the embodiment of FIG. 89a, the first 812 and second 891 plates are adapted to be in contact with each other, in use, in a contacting surface which according to this embodiment comprises ceramic material for resisting wear.

The operation device is placed in a sealed chamber confined by the piston 801 and the sleeve 802. The piston 801 and sleeve 802 is according to this embodiment adapted to be in contact with each other and to create a seal in a contact point 807. The contact point 807 could comprise a ceramic material resistant to wear, which prolongs the life of the implantable device. According to the embodiment of FIG. 89a, the eccentrically rotating member 891 is adapted to create movement of the piston 808 in a first direction, the movement in the opposite direction is created by spring members 805 which are loaded when the eccentrically rotating member 891 presses the piston 808 in the first direction. The piston 808 could be adapted to be in direct contact with the heart, or to affect an arm or heart contacting organ, which in turn is in contact with the heart.

Figure 89B:
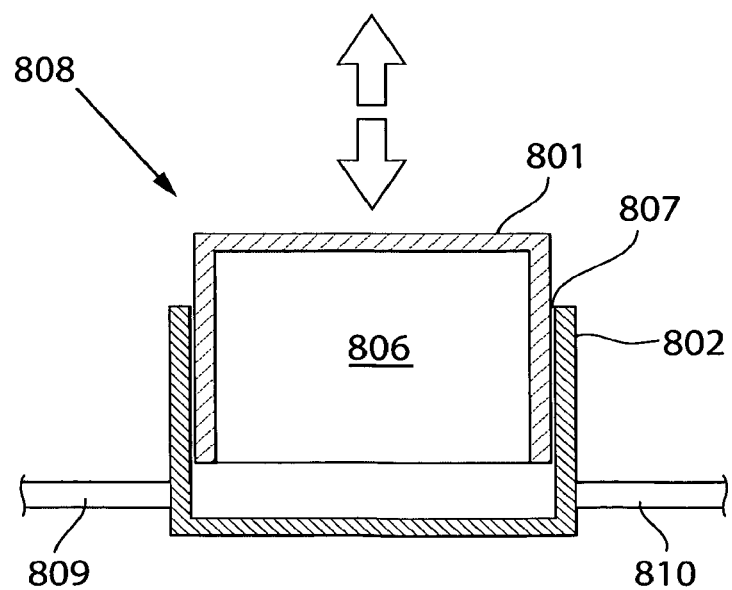
FIG. 89b shows a sealed chamber for hydraulic use.

FIG. 89b shows another embodiment of the implantable device, comprising a piston placed in a sleeve 802. The piston and the sleeve together confines a sealed space adapted to 806 receive a high pressured hydraulic fluid from an inlet 809. The high pressured hydraulic fluid is adapted to push the piston 801 in a first direction, whereas the vacuum created when the hydraulic fluid is sucked from the sealed space 806 through the outlet 810. The piston 801 is in contact with the sleeve 802 in a contact point 807, here being an area 807 between the sleeve 802 and the piston 801. The contacting area 807 could be made from a ceramic material and thereby adapted to better resist the wear that is created by the implantable device having to operate at the speed of the heart. The hydraulic fluid could for example be pressurized using a hydraulic pump. According to some embodiments the system is a pneumatic system in which case the implantable device is powered by a gas compressed by a pneumatic pump. In yet other embodiments (not shown) the piston 801 is adapted to be moved in the opposite direction by means of spring members 805, much like the embodiment of FIG. 89a, this could be needed if the piston 801 and sleeve 802 are very tightly fitted for sealing against a very high pressure since the force exerted by vacuum is limited.

Figure 90:
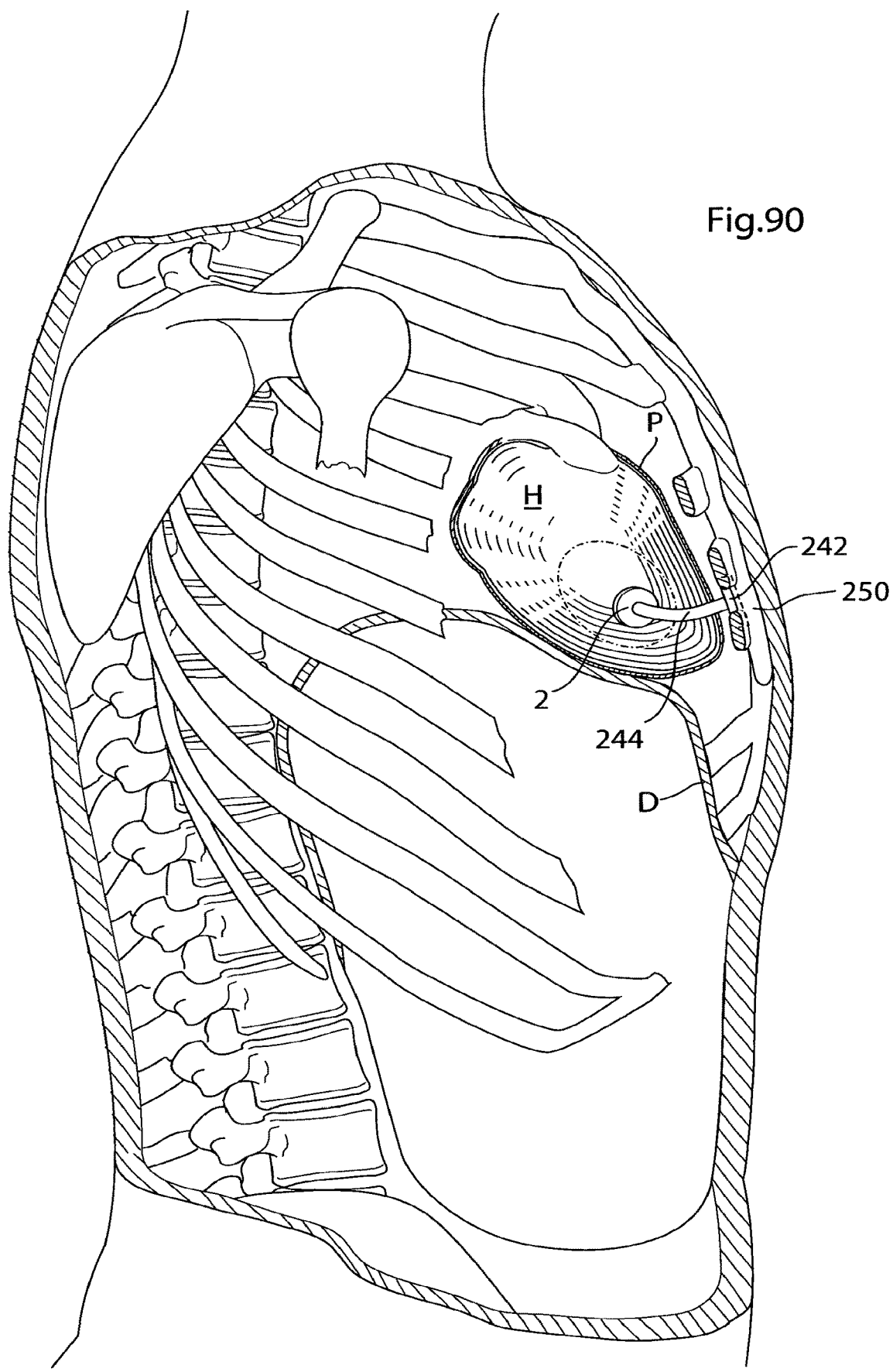
FIG. 90 shows a lateral view of a patient when a heart help device is fixated to the sternum of the patient, on the inside thereof.

FIG. 90 shows a lateral view of a human patient in section where an implantable device for assisting the heart function is implanted. The heart H is placed in the pericardium P which is a heart covering sac in which the heart H is placed. The pericardium P rests on, and is fixated to the thoracic diaphragm D separating the thorax from the abdomen. The implantable device comprises a connecting arm 244 connecting a heart contacting organ 2 to a plate 242 fixated to the sternum 250 of the patient. According to other embodiments the plate 242 or the fixation arm 244 could be fixated to at least one rib of the patient, or at least one vertebra. According to the embodiment of FIG. 90 the heart help device is a device adapted to compress the heart by exerting a force on the external part of the heart H, however in other embodiments the heart help device could be an artificial heart, or en LVAD device, fixated to a part of the human body comprising bone in the same way.

The heart rests on the superior surface of the thoracic diaphragm D. The pericardium P is a triple-layered sac that encloses the heart H. The outer layer being the fibrous pericardium adheres to the thoracic diaphragm D inferiorly and superiorly it is fused to the roots of the great vessels that leave and enter the heart H.

By creating the opening and placing a diaphragm contacting part 501, which according to some embodiments is a grommet, in the area of the thoracic diaphragm D in which the heart H rests it is possible to gain access to the pericardium P without actually entering the thoracic cavity outside of the pericardium P. The pressure in the thoracic cavity is somewhat different from the pressure in the abdominal cavity, which among other things makes it more advantageous to be able to connect a heart pump device engaging the heart H to an operating device placed in the abdominal cavity without entering the thoracic cavity outside of the pericardium P.

Figure 91:
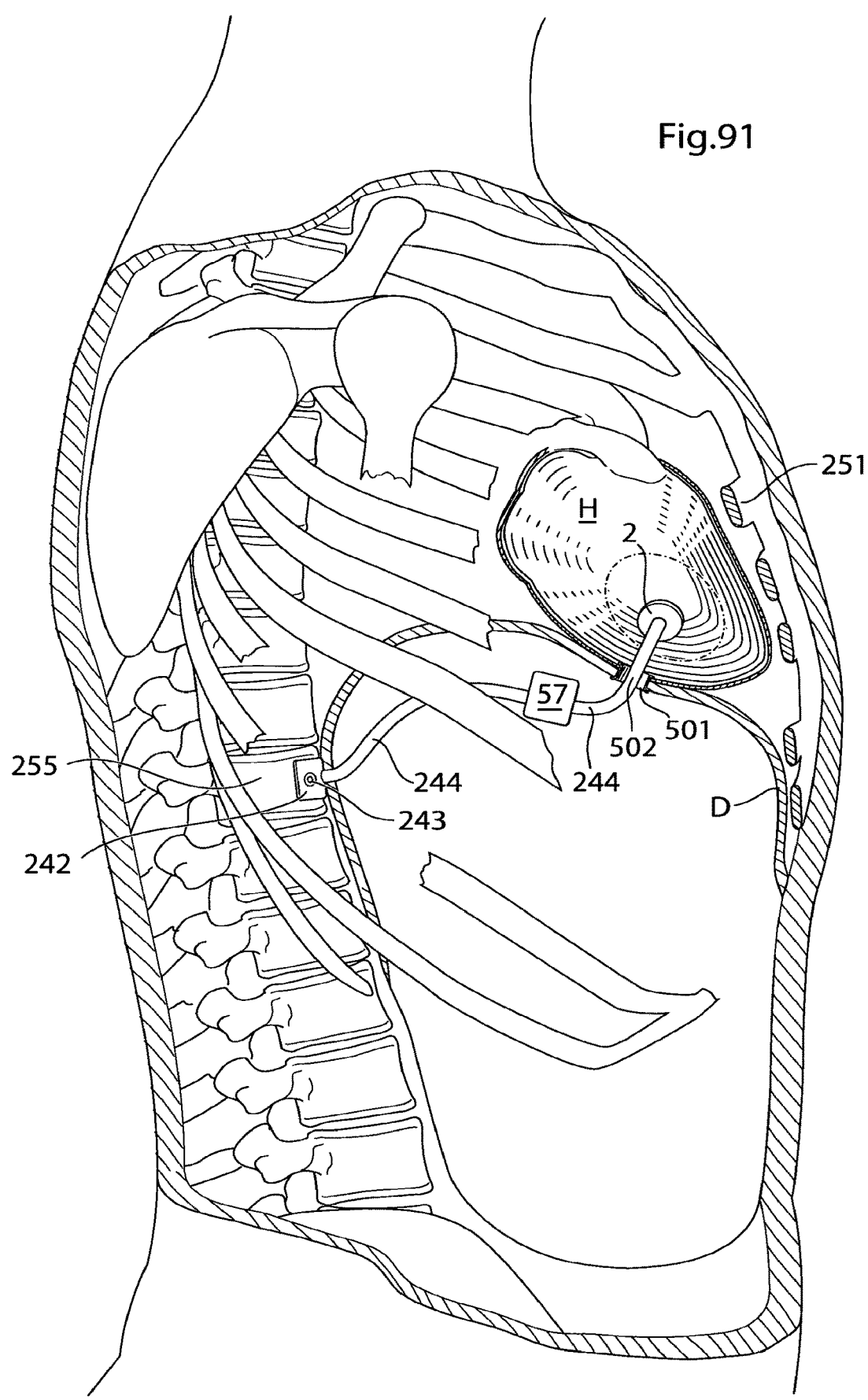
FIG. 91 shows a lateral view of a patient when a heart help device is fixated to a vertebra of the patient.

FIG. 91 shows a lateral view of a human patient in section where an implantable device for assisting the heart function is implanted. A connecting arm is fixated to a plate 241 which is fixated to a vertebra of the vertebral column using a screw 243, however alternative means of fastening is equivalently conceivable, such as pop rivets, adhesive or a fixating wire. The connecting arm is in turn fixating an operating device 57, adapted to operate the heart help device. From the operating device another portion of the connecting member 244, being a force transferring member 502 extends forward and upward in the figure. The force transferring member 502 is adapted to transfer force from the operating device 57 to the heart contacting organ 2 placed in connection with the heart. The force transferring member 502 transfers force through a diaphragm contacting part 501, in this case being a grommet 501 placed in contact with the thoracic diaphragm D and thereby assisting in the maintaining of an opening from the abdominal side of the thoracic diaphragm D to the thoracic side of the thoracic diaphragm D. In other embodiments the diaphragm contacting part is excluded and the force transferring member 502 (or diaphragm passing part) thereby transfers force through the thoracic diaphragm D, passing an opening in the thoracic diaphragm D without passing through a diaphragm contacting part The operation device 57 could be an operation device adapted to create a mechanical force, a hydraulic force, a pneumatic force which is then transferred by the force transferring member 502. In other embodiments an energy supply such as a battery is placed in the abdomen and fixated to a part of the human body comprising bone. The electric energy is then transferred to through an electrical lead passing through the thoracic diaphragm D through the diaphragm contacting part 501 assisting in the maintaining of an opening in the thoracic diaphragm D. In other embodiments the electric energy is transferred through an opening in the thoracic diaphragm D through an opening in the thoracic diaphragm D without passing a diaphragm contacting part.

Figure 92:
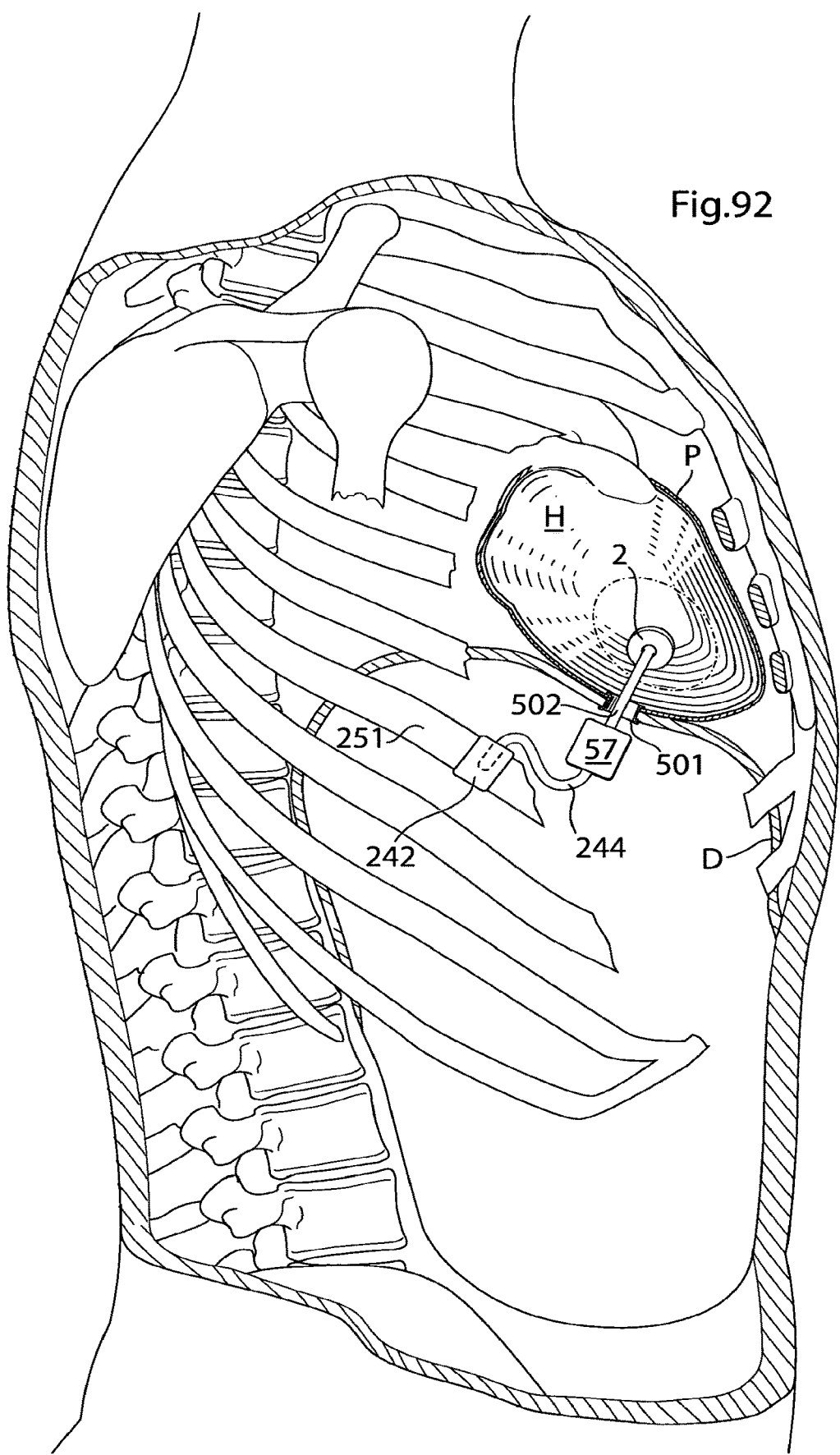
FIG. 92 shows a lateral view of a patient when a heart help device is fixated to a rib of the patient.

FIG. 92 shows a lateral view of a human patient in section where an implantable device for assisting the heart function is implanted. A connecting member 244 connects an operating device 57 to a rib 251 of the patient through a fixation plate 242 being fixated to said rib 251. The operating device 57 is in turn adapted to operate a force transferring member 502 placed between said operating device 57 and a heart contacting organ 2 adapted to be in contact with the heart H. The force transferring member 502 is adapted to transfer force through a diaphragm contacting part 501 placed in the thoracic diaphragm D and assisting in maintaining an opening in the thoracic diaphragm D and the pericardium P. This is further explained with reference to FIG. 91. The fixation plate 242 is here placed on the outside of the rib 251, however it is equally conceivable that the fixation plate 242 is placed on the inside. The fixation plate 242 could for example be fixated to the rib 251 using screws which could be adapted to fixate the plate 242 to the outer cortex of the rib 242, the inner cortex of the rib 251, both the inner and outer cortex of the rib 251, or in a through going embodiment wherein the screw thus clamps the rib 251 for example through a nut and bolt arrangement, or a second plate with threads placed on the inner or outer side of the rib 251.

FIG. 93a shows a lateral view of a human patient in section where an implantable device for assisting the heart function is implanted. In the embodiment of FIG. 93a a fixation plate 242 is fixated to the inside of the sternum 250. A connecting arm 244 is fixated to the connecting arm 244 and penetrates the thoracic diaphragm D through a first diaphragm contacting part 501b. The connecting arm 244 in turn fixates an operating device 57 which operates a force transferring member 502 which in turn transfers force through the thoracic diaphragm D through a second diaphragm contacting part 501 to the heart help device comprising a heart contacting organ 2 adapted to be in contact with the heart H of the patient. The second heart contacting part 501 assists in the maintaining of an opening in the thoracic diaphragm D and the pericardium P. This is further explained with reference to FIG. 91, and the diaphragm contacting parts 501, 501b and force transferring member 502 is further described with reference to FIGS. 101-107.

Figure 93B:
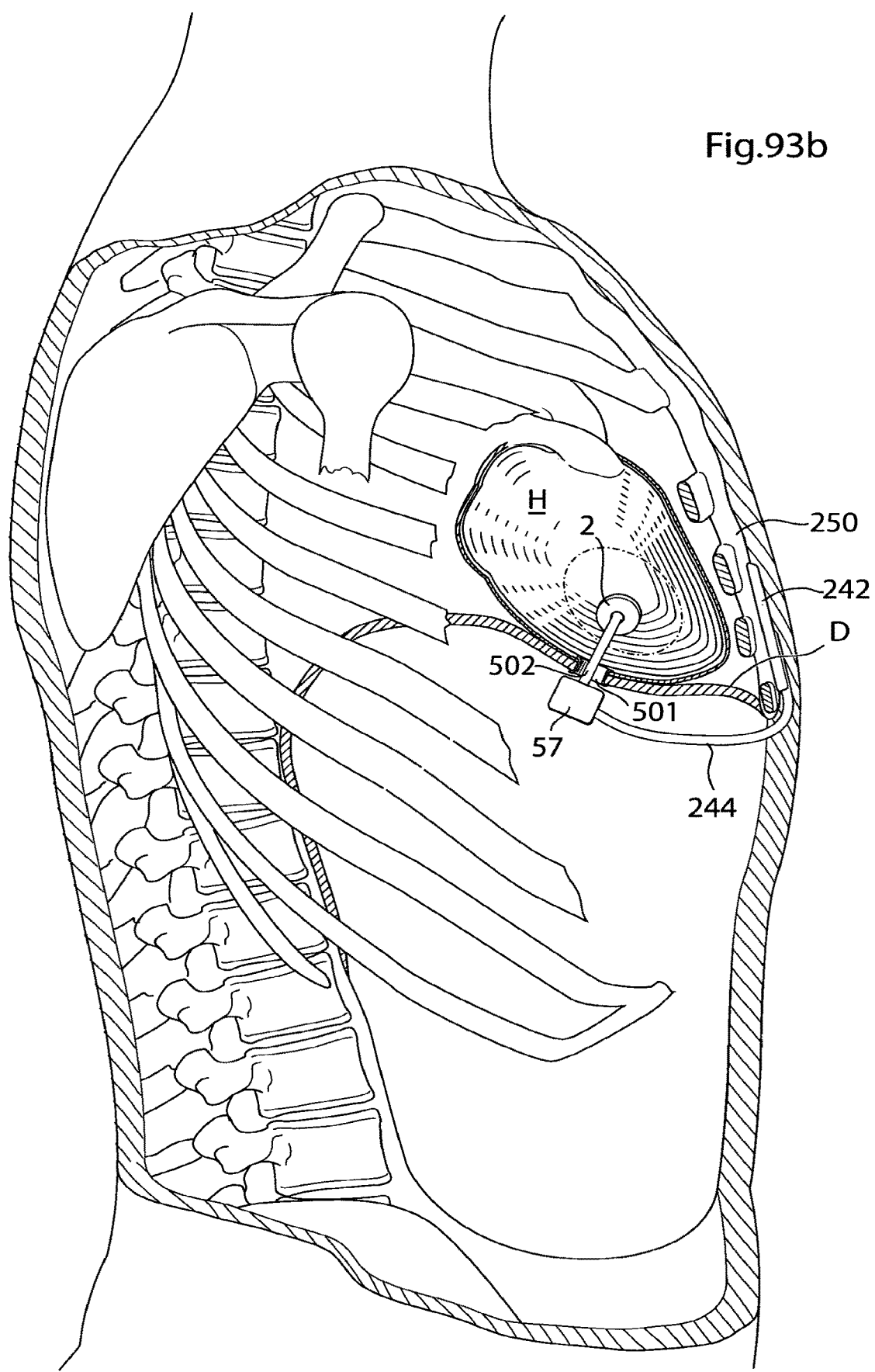
FIG. 93b shows a lateral view of a patient when a heart help device is fixated to the sternum of the patient, on the outside thereof.

FIG. 93b shows a lateral view of a human patient in section where an implantable device for assisting the heart function is implanted. In the embodiment of FIG. 93b a fixation plate 242 is fixated to the outside or anterior side of the sternum 250. A connecting arm 244 then passes along the sternum and in to the abdomen of the patient and is bent to extend in to the abdomen to a section of the thoracic diaphragm D in which the pericardium P rests and is fixated to the thoracic diaphragm D. From the operating device 57 a force transferring member 502 penetrates the thoracic diaphragm D through a diaphragm contacting part 501. The heart contacting organ 2 in contact with the heart 2 is a part of a heart help device adapted to assist the pump function of the heart by exerting a force on the external part of the heart. This embodiment enables a fixation of the operating device 57 and the heart help device in the abdomen without having to enter the thorax outside of the pericardium P. This makes it possible to separate the thorax from the abdomen which, among other aspects, is advantageous since there is a difference in pressure between the thorax and the abdomen.

FIG. 94 shows a surgical or laparoscopic method of creating and maintaining a opening in the thoracic diaphragm D of a patient. The method comprises the steps of: creating an incision 503 in the thoracic diaphragm D and thereby creating a opening 503 in the thoracic diaphragm D, placing a diaphragm contacting part 501 in contact with the thoracic diaphragm D, thereby maintaining the opening 501 created in the thoracic diaphragm D. According to the embodiment of FIG. 94 the opening 503 in the thoracic diaphragm D is made in the section of the thoracic diaphragm D in which the pericardium P rests and is fixated, the opening continues into the pericardium P of the patient, which create an opening reaching from the abdomen and into the pericardium P enabling an element to be placed in contact with the heart H through the said opening 503. FIG. 94 further shows a section of a heart help device comprising a heart contacting organ 2, a connection arm 244, a fixation plate 242 and a screw 243 for fixation of the fixation plate 242. The connection arm 244 is bent such that said connecting arm 244 is adapted to fixate a heart help device to a part of the human body comprising bone through the diaphragm contacting part 501 maintaining an opening in the thoracic diaphragm D.

Figure 95:
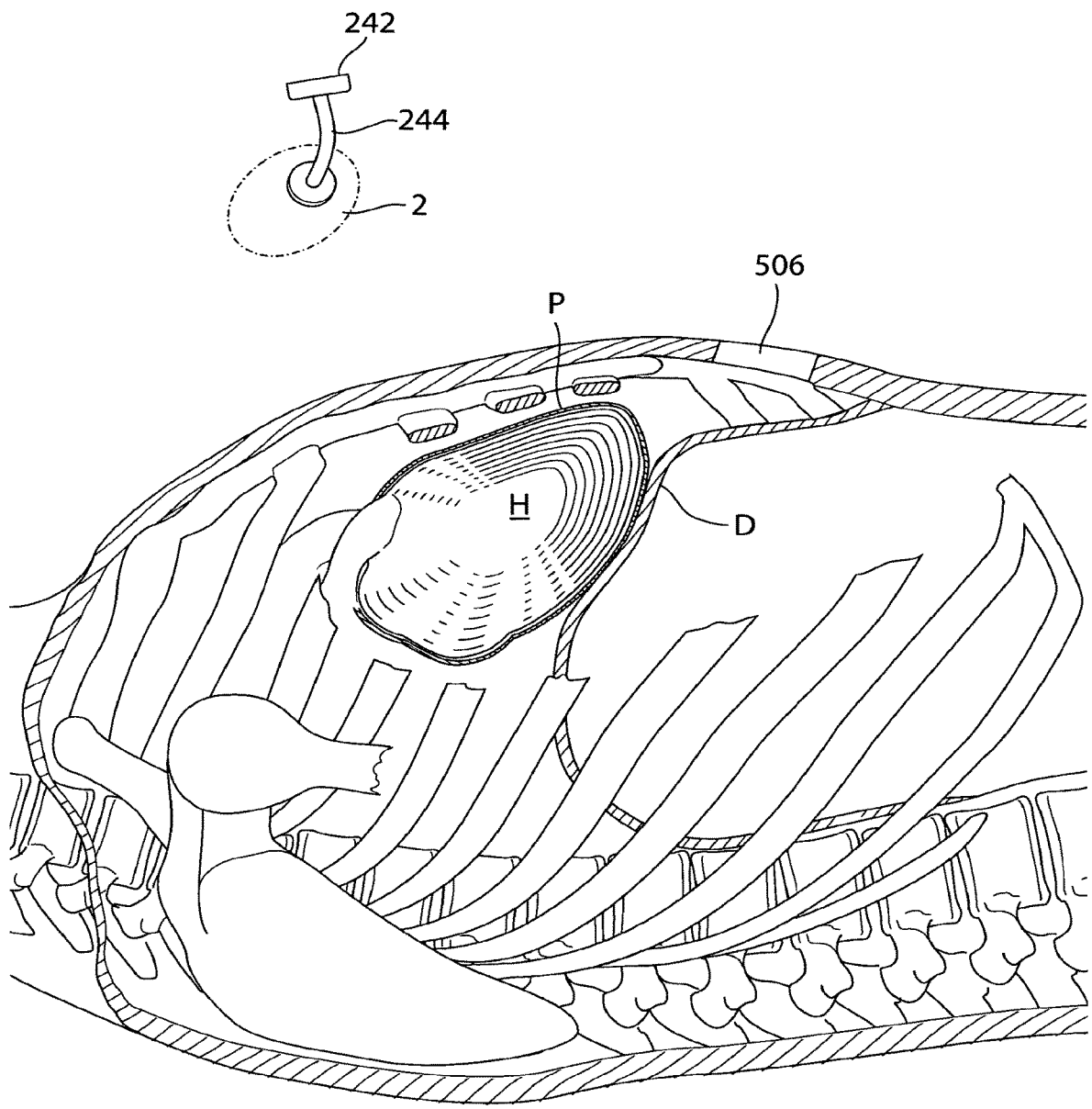
FIG. 95 shows a lateral view of a patient, when an opening is created in the thorax of the patient.

FIG. 95 shows a lateral view of a patient showing the heart H being placed in the pericardium P in the thorax resting on and being fixated to a section of the thoracic diaphragm D. FIG. 95 shows a illustrates a method of placing a heart help device through an incision in the thorax 506. The heart help device comprising a fixation plate 242, a connecting arm 244 and a heart contacting organ 2. The operation methods of FIGS. 94 and 95 could be performed as surgical methods or laparoscopic methods where the steps of the methods are performed through trocars placed in the thorax and abdomen, respectively.

Figure 96:
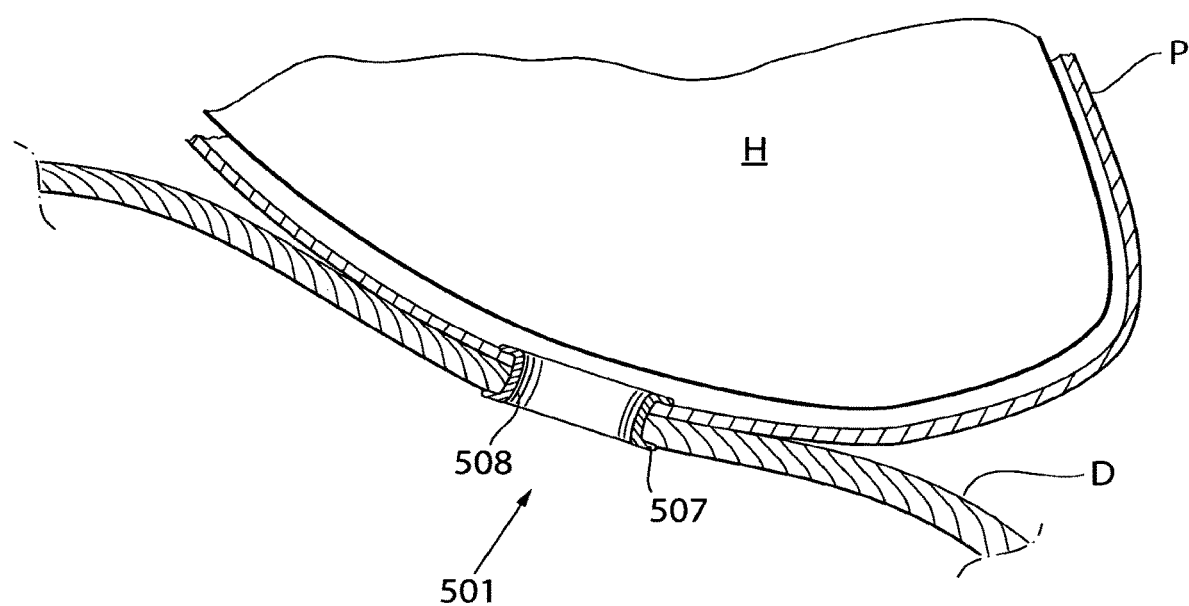
FIG. 96 shows a close-up of a diaphragm contacting part maintaining an opening in the thoracic diaphragm.

FIG. 96 shows a close-up of part of the thoracic diaphragm D and the pericardium P in the section of the thoracic diaphragm D in which the pericardium P rests and is fixated. The diaphragm contacting part 501 is assisting in the maintaining of an opening in the thoracic diaphragm D and the pericardium P. The diaphragm contacting part 501 is a grommet like structure with protrusions 507 extending from the part of the diaphragm contacting part 501 defining the opening from the abdominal side of the thoracic diaphragm D to the thoracic side of the thoracic diaphragm D. The protrusions 507 clamps the edges of the opening in the thoracic diaphragm D and the pericardium P and thereby assists in the fixation of the diaphragm contacting part 501 to the thoracic diaphragm D and the pericardium P.

Figure 97A:
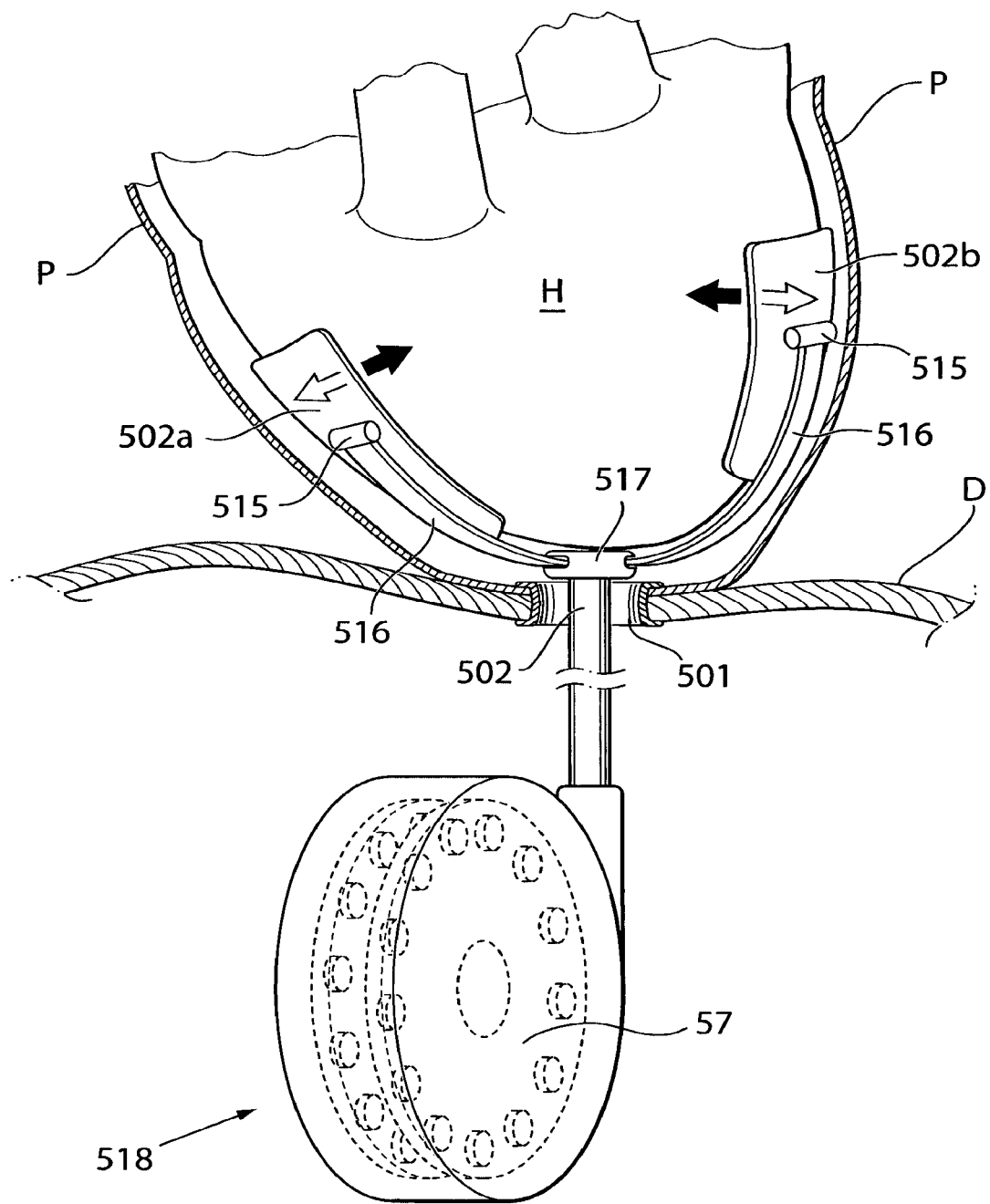
FIG. 97a shows an embodiment of a heart help device where force is transferred through the thoracic diaphragm.

FIG. 97a shows an embodiment of a heart help device adapted to assist the pump function of the heart by exert force on the outside of the heart H. The heart H is placed in the pericardium P which rests and is fixated to the thoracic diaphragm D at a section of the thoracic diaphragm. FIG. 97*a* shows an embodiment where an operation device 57 is placed in the abdomen of a patient. A force transferring member 502 comprises a first and second portion. The first portion is connected to an operation device 57 placed in a sealing operation device container 518 adapted to protect the operation device 57 from the environment of the abdomen. The second portion of the force transferring member 502 is connected to a force entering section 517 of the heart help device placed in the pericardium P. The force entering section transfers the force supplied by the force transferring member 502 to two arms 516 connected to two force transferring members 502*a* and 502*b* at a pivotable joint 515. The heart contacting organs 502*a,b* are adapted to be in contact with the heart H on the anterior and posterior side of the heart H for exerting force on the heart H to assist the pump function thereof.

The force transferring part 502 is adapted to transfer force through the thoracic diaphragm D at a section of the thoracic diaphragm D in which the pericardium P rests and is fixated to the thoracic diaphragm D. An opening in the thoracic diaphragm D and the pericardium P is maintained be a diaphragm contacting part 501 adapted to be in connection and fixated to the pericardium P and/or the thoracic diaphragm D.

The operating device shown in FIG. 97*a* is a magnetic operating device further disclosed with reference to FIGS. 7 and 8, however it is equally conceivable that the operating device is an electrical motor, a servo motor, a hydraulic motor or a pneumatic motor. The operating device could be adapted to create a rotational mechanical force and/or a translational mechanical force and/or an eccentrically rotating mechanical force.

Figure 97B:
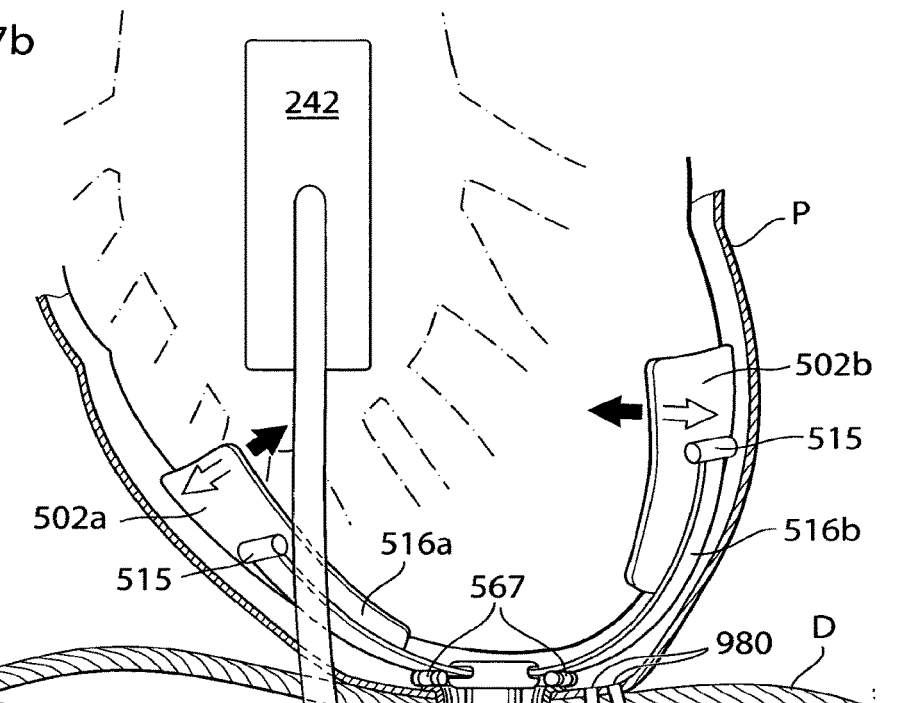
FIG. 97b shows a second embodiment of a heart help device where force is transferred through the thoracic diaphragm.

FIG. 97*b* shows an embodiment of an implantable heart help device comprising the elements of the embodiment shown in FIG. 97*a*. The embodiment of FIG. 97*b* further comprises a fibrotic tissue movement structure 560 being a bellows shaped elastic member with protrusions 561 and recesses 562 for enabling movement of the force transferring member even after fibrotic tissue has begun to grow on the fibrotic tissue movement structure 560 after the implantable device has been implanted in a patient for some time. The fibrotic tissue movement structure 560 is fixated to the sealing operation device container 518 placed in the abdomen of the patient, and to the diaphragm contacting part assisting in the maintaining of an opening in the thoracic diaphragm D. The force transferring part 502 placed between the heart help device and the operation device container 518 placed in the abdomen comprises a first 563 part in connection with the operating device 57 and a second part 564 in connection with the heart help device. The first 563 and second 564 part constitutes a respiration movement compensator for compensating for the movements in the body created by the respiration of the patient. The respiration movement compensator is extend/compressible through a telescopic functionality. A guide pin 565 is fixated to the first part 563 and placed in a groove in the second part 564 and the respiration movement compensator thereby enabled transfer of torque/rotational force while maintaining the ability to extend/compress for compensating for the movements in the body created by the respiration of the patient. FIG. 97*b* further shows a fixation member comprising a connecting arm 244 and a fixation plate 242. The fixation member is adapted for fixating the implantable device to the outside of the sternum or at least one rib, however, embodiments where the fixation members is adapted to enable fixation of the implantable heart help device to the outside of the sternum or at least one rib is equally conceivable. To enable the respiration movement compensation to function the arms 516*a,b* are pivotably arranged to the diaphragm contacting part 501 and movable in relation to the operation device container 518.

FIG. 97*b* further shows a pericardial drainage device for draining a fluid from the pericardium P of a patient. The drainage device comprises a conduit comprising a first 980 and second 981 section. At portion of the first section 980 is adapted to receive a fluid inside of the pericardium P. The second section 981 of the conduit is adapted to be positioned outside of the pericardium P of the patient and enable the exhaust of the fluid received from the pericardium P through at least a portion of the second section 981.

The pericardial drainage of the embodiment of FIG. 97*b* is adapted move a fluid from the pericardium P of the patient to the abdomen of the patient, however in other embodiments it is equally conceivable that the drainage device is adapted to move fluid from the pericardium P to any other location in the body. The second section 981 could be connected to an implantable container 983 for collecting the drained fluid, or an exhaust member for exhausting the fluid into the abdomen of the patient.

Figure 97C:
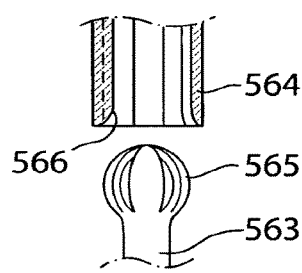
FIG. 97c shows an alternative embodiment of the respiratory movement compensator.
Figure 97D:
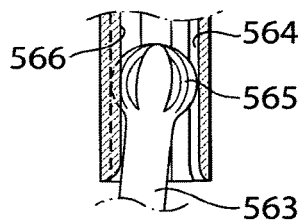
FIG. 97d shows an alternative embodiment of the respiratory movement compensator in a second state.

FIG. 97*c* shows an alternative embodiment of the respiration movement compensator disclosed with reference to FIG. 97*b*. This alternative embodiment enables movements around a spherically shaped connecting part of the first part 563. The connecting part comprising splines 565 adapted to be placed in corresponding splines 566 in the second part 564 for enabling the transfer of torque while maintain the ability to move in multiple directions. FIG. 97*d* shows the respiratory movement compensator when the first part 563 is tilted in the second part 564.

Figure 98:
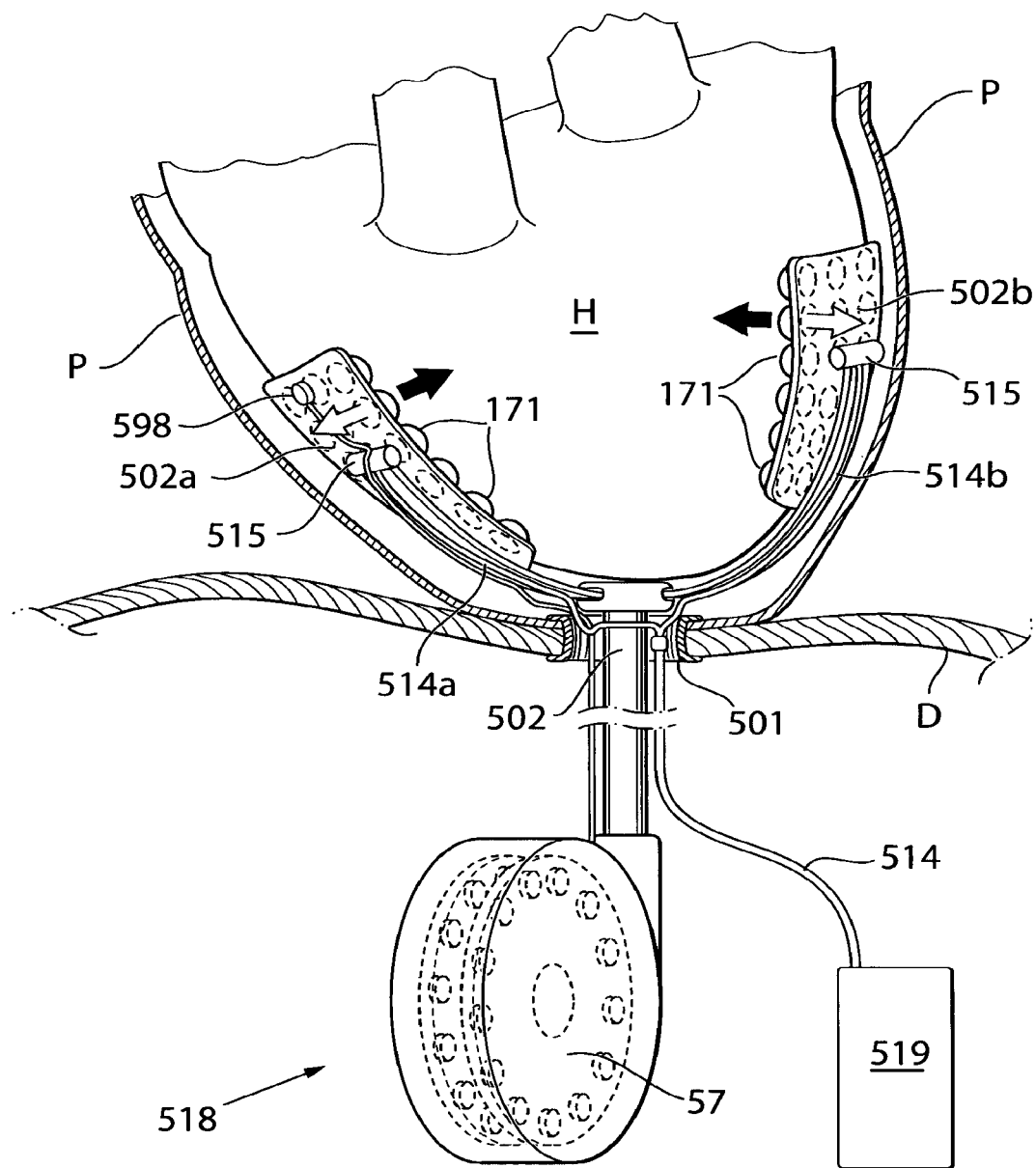
FIG. 98 shows a second embodiment of a heart help device where mechanical and hydraulic force is transferred through the thoracic diaphragm.

FIG. 98 shows the implantable heart help comprising the elements of the heart help device disclosed with reference to FIG. 97*a*. The heart contacting organs 502*a,b* of FIG. 98 further comprises hydraulic or pneumatic cushions 171 adapted to exert force on the heart H. The hydraulic or pneumatic cushions 171 could change to alter the area of the heart H to which force is exerted. The cushions comprises chambers having a volume and the size of that volume is adapted to be changeable individually, for each cushion to influence the force exerted on the heart H after the implantable heart help device has been implanted in the patient. The hydraulic or pneumatic cushions have volumes adapted to be changed using an implantable hydraulic or pneumatic system 519, according to this embodiment adapted to be placed in the abdomen of the patient. The hydraulic or pneumatic system comprises multiple conduits 514, which according to this embodiment separates into two section 514*a,b* for enabling movement of the cushions 171 of the first and second heart contacting organ 502*a,b*. the hydraulic or pneumatic conduits 514 is according to this embodiment adapted to transfer force through an opening in the thoracic diaphragm D adapted to be maintained by a diaphragm contacting part 501. In the embodiment of FIG. 98 the diaphragm contacting part is thus adapted to allow both a mechanical force transferring member 502 and a hydraulic pneumatic force transferring member to pass through the diaphragm contacting part 501. In other embodiments (not shown) the implantable heart help device further comprises an electric system at least partially adapted to be placed in the abdomen of the patient and comprising an electric lead adapted to transfer electric energy, an electric control signal or sensor input to or from the part of the implantable heart help device placed in the thorax of the patient. The heart help device according to any of the embodiments herein could further comprise one or more sensors 598 providing input. This could in any of the embodiments herein for example be a signal relating to the heart rhythm, the blood pressure, the blood flow, electric activity of the heart, temperature, time or variable relating to the content of the blood, such as saturation, sodium, erythrocytes, leukocytes and/or trombocytes. The heart help device according to any of the embodiment herein could further be equipped with at least one electrode supplying an electric signal for controlling the heart rhythm, such as a pace maker signal. The energizing system or control unit for handling the sensor signals could be adapted to be placed in the abdomen of the patient.

Figure 99A:
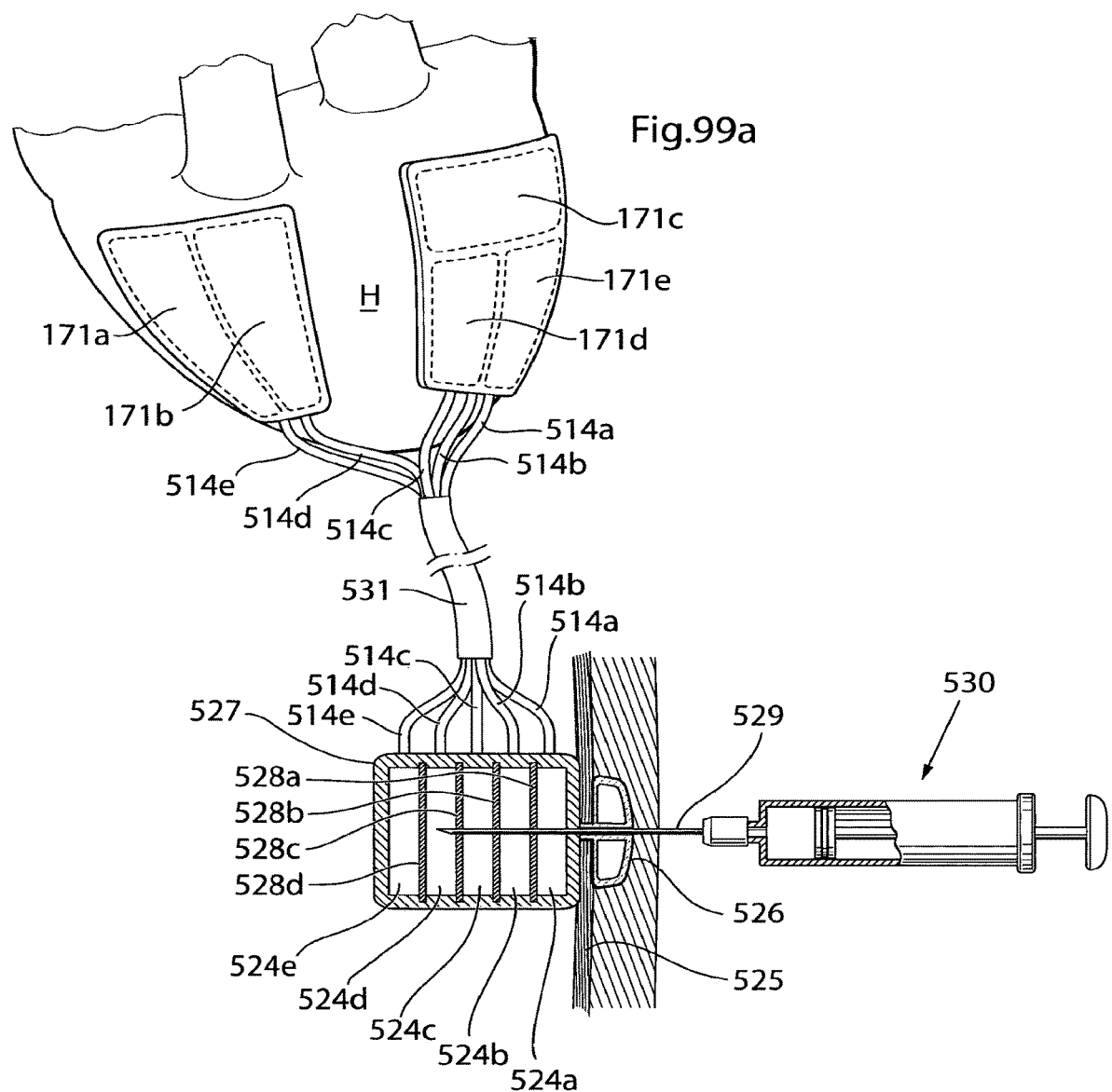
FIG. 99a shows a first embodiment of a multi-chamber injection port for calibrating elements pressing on the heart.

FIG. 99a shows the implantable heart help device in an embodiment where the heart help device comprises a hydraulic system for controlling a plurality of hydraulic cushions 171a-e. The hydraulic system comprises an implantable injection port unit 527. The injection port unit 527 comprising a plurality of chambers 524a-e each comprising wall sections being penetratable self sealing membranes 528a-d adapted to be penetrated by a needle 529 attached to an injecting member 530 for injecting a fluid into the chambers 524a-e. The needle is inserted through a insertion guide 526 fixated to human tissue 525 for example by subcutaneous implantation. The needle is then inserted through one or more of the wall sections 528a-d for injecting a fluid into a specific chamber 524a-e and thereby affect a specific cushion 171a-e and by the connection through the conduits 514a-e. In the embodiment shown in FIG. 99a the plurality of conduits are bundled into a conduit bundle 531.

The location on the needle 529, i.e. in which chamber 524a-e the fluid is injected could be controlled by a system of sensors that by for example induction feels the presence of the needle 529 in a specific chamber 524a-e. The system of sensors could be adapted to wirelessly transmit the signals to the physician injecting the fluid into the system. It is furthermore conceivable that the system comprises sensors sensing the amount of hydraulic fluid injected to specific chambers 524a-e and thereby how much each cushion 171a-e has been affected.

Figure 99B:
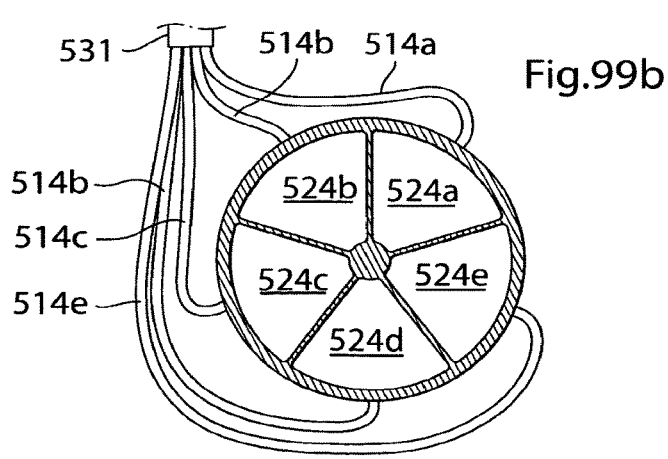
FIG. 99b shows a second embodiment of a multi-chamber injection port.

FIG. 99b shows an alternative design of the injection port unit as described with reference to FIG. 99a. The injection port unit here has the plurality of chambers 524a-e placed next to each other and thereby the needle does not have to penetrate several wall portions to reach a specific chamber 524a-e.

Figure 99C:
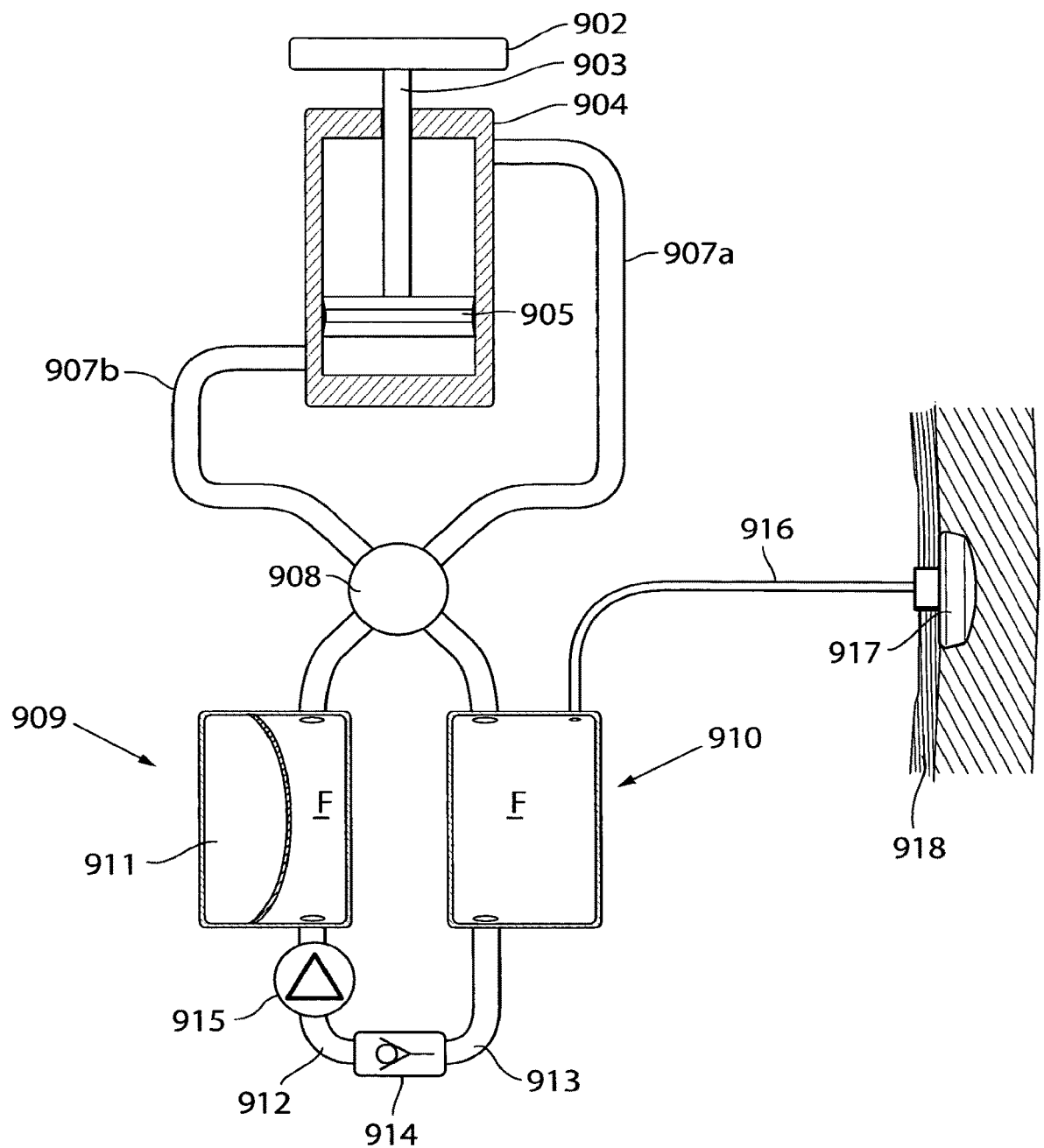
FIG. 99c shows a hydraulic/pneumatic two chamber system.

FIG. 99c shows an embodiment of a hydraulic system for supplying force to an implantable heart help device. The hydraulic system comprises a cylinder 904 in which a piston 905 is placed such that a first and second chamber 906a,b exists on the two sides of the piston 905. The piston 905 is adapted to move in said cylinder 904 in response to the chambers 906a,b being pressurized using a hydraulic or pneumatic fluid F. The system further comprises a first and second conduit 907a,b for transferring the hydraulic or pneumatic fluid F to the two chambers 906a,b.

Two chambers 909 and 910 comprises the hydraulic or pneumatic fluid F. The first chamber 909 is adapted to be a high pressure chamber and adapted to hold a fluid F having a high pressure. The pressure is maintained by a pressurized gas 911 being confined behind a membrane of the chamber and thereby exerting a pressure on the fluid in the chamber 909. The fluid is transported to a valve 908 that has two states. In the first state of the valve the valve guides the fluid from the first high pressure chamber to the second cylinder chamber 906b pressing the cylinder 905 upwards in the FIG.

In this state the valve also enables the fluid from the first cylinder chamber 906a to be pressed into the conduit 907a and through the valve and into the low pressure chamber 910. The fluid is then pumped to the high pressure chamber 909 using a pump 915 placed between a first 913 and second 912 part of a conduit. A check valve 914 is further placed on the conduit for enabling the pressure in the high pressure chamber 909 to remain high even when the pump 915 is turned off. At a second state of the valve 908 the fluid is guided from the high pressure chamber 909 through the conduit 907a and into the first cylinder chamber 906a, which thereby pushes the cylinder downwards in the FIG. The second cylinder chamber is thereby emptied in an a procedure analogue the what was described for the first cylinder chamber 906a and the fluid is passed to the low pressure chamber 910. The cylinder 905 is connected to a rod 903 transferring the force to a heart contacting organ 902, directly, as disclosed in FIG. 99c, or via an intermediary part. The system further comprises an injection port 917 for refilling or calibrating the system. The injection port 917 is implanted subcutaneously and fixated to a tissue of the body 918 and connected to the low pressure chamber 910 by a conduit 916.

By the function of the system disclosed with reference to FIG. 99c the system can move the cylinder 905 and thereby the heart contacting organ 902 using a pressurized fluid F in two directions, which eliminated the limitation in force that operation by vacuum places on a system.

Figure 99D:
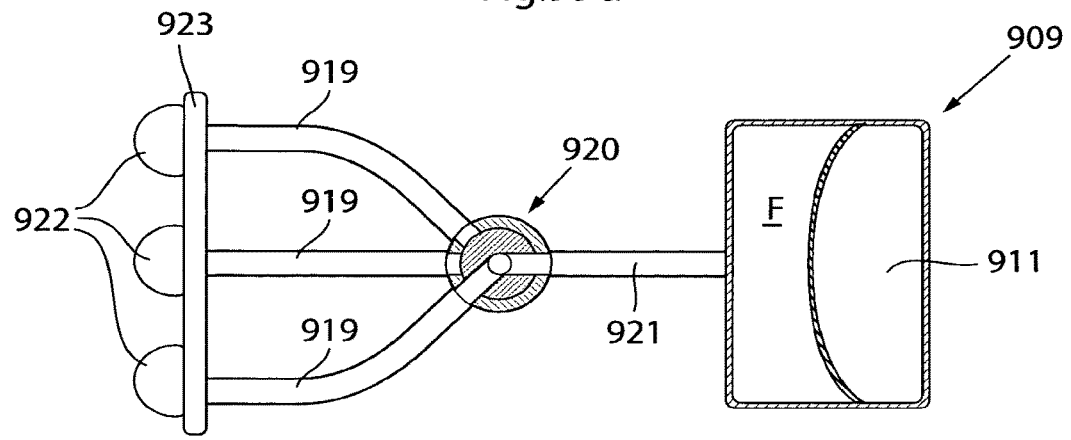
FIG. 99d shows a hydraulic/pneumatic system comprising a selection valve.

FIG. 99d shows a hydraulic system with similar functionality as the system of FIG. 99a. A high pressure chamber 909, comprising a gas pressure 911, presses a fluid F, which is in contact with a valve through a conduit 921. The valve 920 is adapted to direct the fluid to a plurality of conduits 919 in connection with a plurality of pistons 922 in connection with a heart contacting organ, for changing the area of the heart in which force is exerted, the pistons being placed on a plate 923.

Figure 99E:
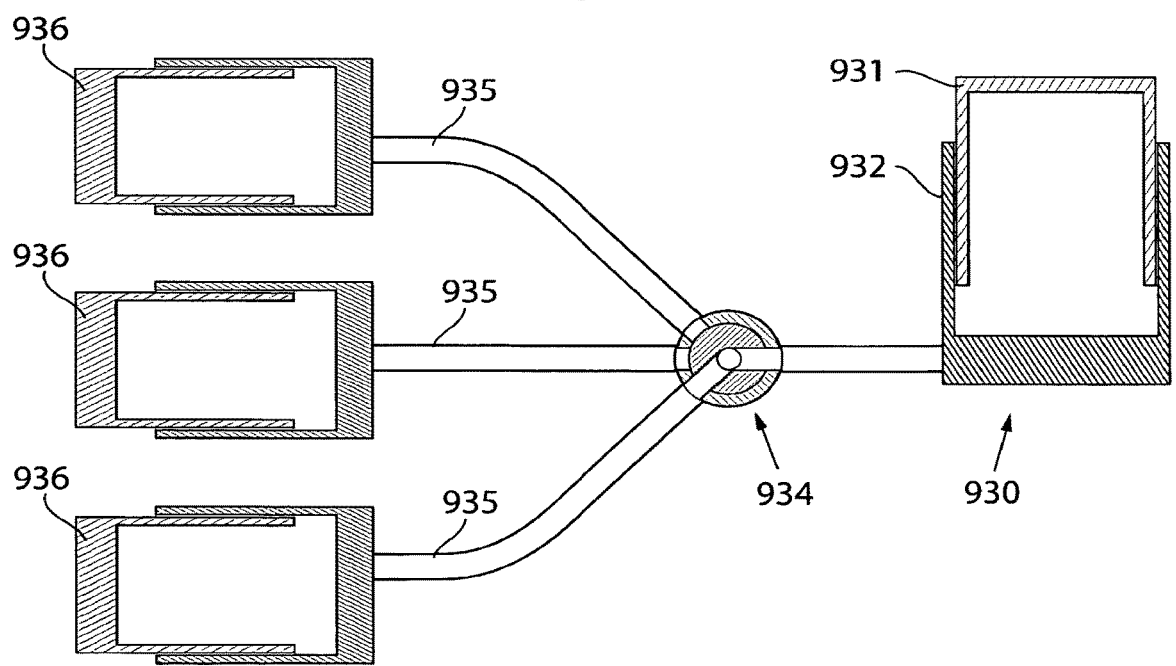
FIG. 99e shows a hydraulic/pneumatic closed force transferring chamber system comprising a selection valve.

FIG. 99e shows a closed system with similar functionality as the system of FIG. 99d. A first cylinder system 930 with a first cylinder 932 and a first piston 931 is adapted to press a fluid through a first conduit 933 to a valve 934. The valve is adapted to be operable to select conduits to direct the force coming from the fluid pressurised by the first cylinder system 930. The conduits are connected to several cylinder systems 936 adapted to receive the force from the first cylinder system 930 and/or transmit force back to the first cylinder system 930. The first cylinder system 930 could be adapted to be connected to an operating device, as disclosed with reference to FIG. 37 for powering the system. By the function described with reference to FIG. 99e a fully implantable system is disclosed for transferring force from one location to several others using a selection valve 934.

Figure 100:
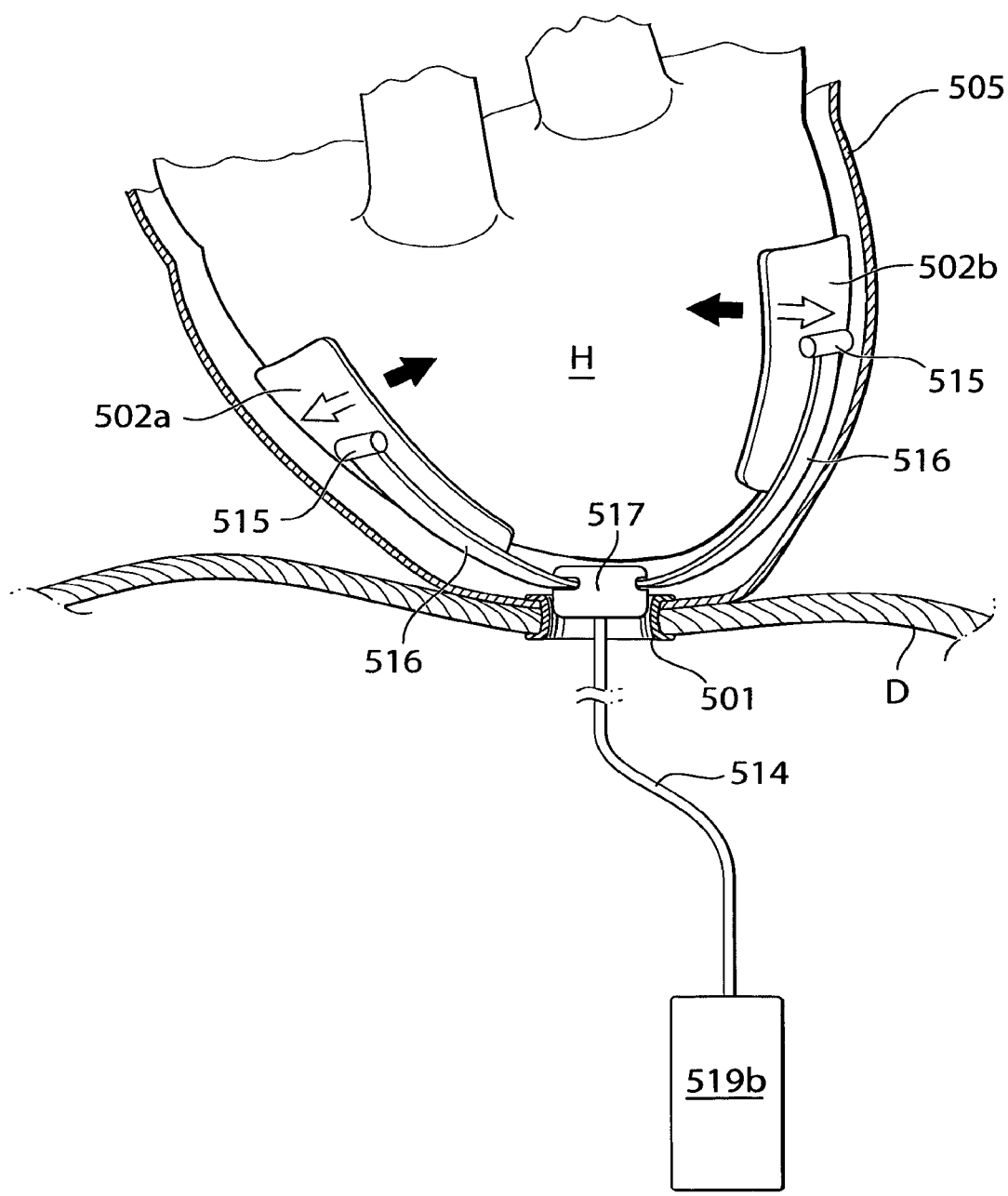
FIG. 100 shows an embodiment of a heart help device in which hydraulic force is transferred through the thoracic diaphragm.

FIG. 100 discloses an implantable heart help device similar to the embodiment disclosed with reference to FIG. 97 with the big difference that the heart help device is operated totally hydraulic by a hydraulic system 519b placed in the abdomen and in a connection with a conduit 514 adapted to transfer force through an opening in the thoracic diaphragm though a diaphragm contacting part 501 adapted to assist in the maintaining of the opening in the thoracic diaphragm D. The conduit transfers force to a force entering section 517 adapted to transform the hydraulic force to mechanical force for exerting force on the heart H by the arms 516 pivotally connected at a joint 515 to the heart contacting organs 502a,b. The hydraulic or pneumatic system 519b could comprise a hydraulic or pneumatic pump creating the force. The system could be powered or controlled non-invasively from outside the body.

Figure 101A:
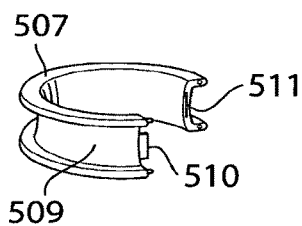
FIG. 101a shows an embodiment of a diaphragm contacting part in which the diaphragm contacting part is adapted to be opened, in an open state.
Figure 101B:
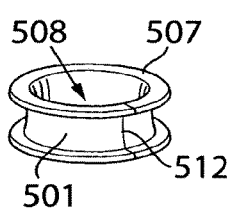
FIG. 101b shows an embodiment of a diaphragm contacting part in which the diaphragm contacting part is adapted to be opened, in a closed state.

FIG. 101a-d shows an embodiment of the diaphragm contacting part disclosed in several embodiments throughout the application. The diaphragm contacting part of FIG. 101a is a diaphragm contacting part adapted to be opened to enable the insertion of force transferring members or diaphragm passing parts. The diaphragm contacting part comprises an outer section 509 which is adapted to engage the edges of an opening created in the thoracic diaphragm. The edges 507 of the thoracic diaphragm could clamp the thoracic diaphragm and thereby assist in the fixation of the diaphragm contacting part to the thoracic diaphragm and/or to the pericardium. The diaphragm contacting part could be closed by means of protrusions 510 in one part of the opening and recesses 511 in the other part of the opening. The protrusions and recesses match and thereby supply a mechanical fixation of the diaphragm contacting part. FIG. 101b shows the diaphragm contacting part possible to open in its closed state. The inner surface 508 of the diaphragm contacting part is smooth not to injure any force transferring member or diaphragm passing part. The inner surface 508 could be made of a highly durable material such as a ceramic material for better resisting the wear that direct contact with a force transferring part creates.

Figure 101C:
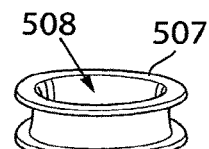
FIG. 101c shows an embodiment of a diaphragm contacting part, which is not possible to open.
Figure 101D:
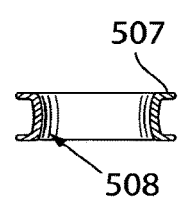
FIG. 101d shows an embodiment of a diaphragm contacting part, in section.

FIG. 101c shows an embodiment of the diaphragm contacting part in which the diaphragm contacting part is a solid ring without the functionality of being able to be opened. The diaphragm contacting part is similar to a grommet and has basically the same functionality. FIG. 101d shows the solid ring in section.

Figure 102:
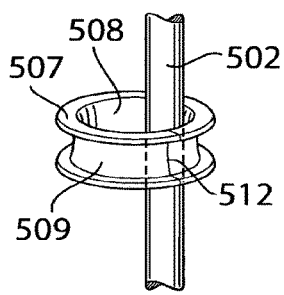
FIG. 102 shows a diaphragm contacting part, with a force transferring member for transferring of mechanical force placed inside.

FIG. 102 shows the diaphragm contacting part in an embodiment when a force transferring member 502 has been placed in the diaphragm contacting part to enable the transfer of force from the abdominal said of the thoracic diaphragm to the thoracic side of the thoracic diaphragm.

Figure 103:
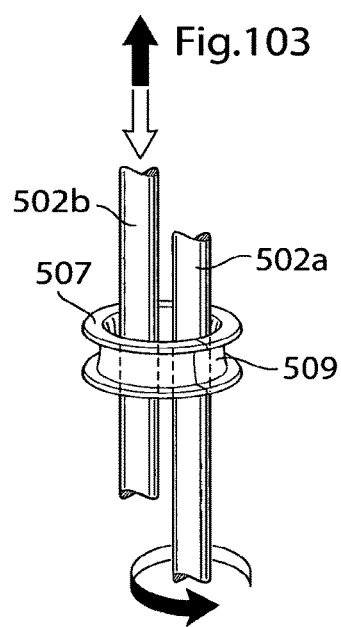
FIG. 103 shows a diaphragm contacting part, with two force transferring member for transferring of mechanical force placed inside.

FIG. 103 shows diaphragm contacting part in an embodiment where two force transferring members 502a,b are placed in the diaphragm contacting part, for transferring mechanical force from the abdominal side of the thoracic diaphragm to the thoracic side of the thoracic diaphragm. According to the embodiment shown in FIG. 103 the force transferring member 502b is adapted to transfer a translating or reciprocating force, whereas the force transferring member 502a is adapted to transfer a rotating force.

Figure 104:
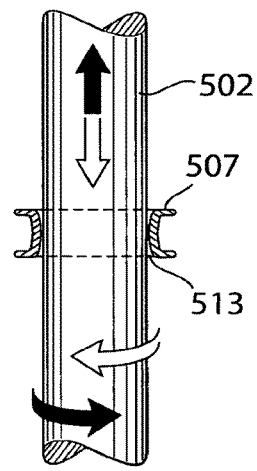
FIG. 104 shows a diaphragm contacting part, with a force transferring member creating a sealing with the diaphragm contacting part placed inside.

FIG. 104 shows a force transferring member 502 placed in the diaphragm contacting part, in an embodiment where the force transferring member 502 is adapted to seal against the diaphragm contacting part 501 and thereby seal the abdominal cavity from the thoracic cavity, which is beneficial since there could be difference in pressure between the abdominal cavity and the thoracic cavity. The seal is created in a contacting point 513. The surfaces of the contacting points 513 could be made of a highly durable material for resisting the wear, such as a ceramic material, for resisting the wear created by the constant contact between the diaphragm contacting part 501 and the force transferring member 502.

Figure 105:
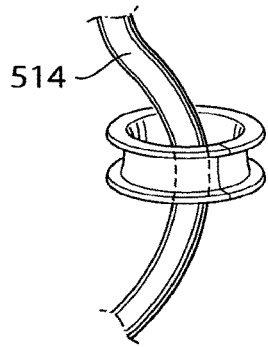
FIG. 105 shows a diaphragm contacting part, with a force transferring member for transferring of hydraulic force placed inside.

FIG. 105 shows the diaphragm contacting part in an embodiment in which a conduit 514 is placed in the diaphragm contacting part for enabling the transfer of hydraulic force from the abdominal side of the thoracic diaphragm to the thoracic side of the thoracic diaphragm.

Figure 106:
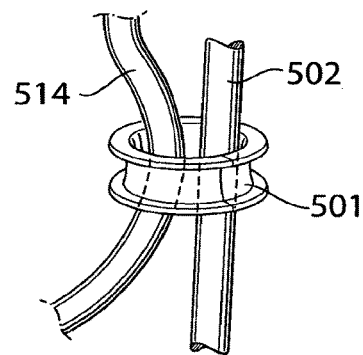
FIG. 106 shows a diaphragm contacting part, with one force transferring member for transferring of hydraulic, and one force transferring member for transferring hydraulic force placed inside.

FIG. 106 shows the diaphragm contacting part in an embodiment where one force transferring member 502 for transferring mechanical force, and one force transferring member 514 for transferring hydraulic force is placed in the diaphragm contacting part.

Figure 107:
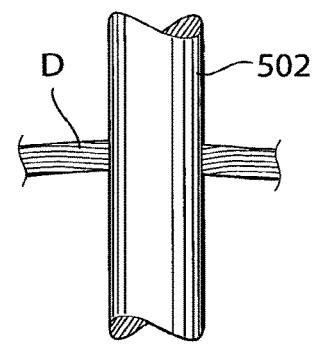
FIG. 107 shows a force transferring part for transferring force through the thoracic diaphragm.

FIG. 107 shows an embodiment in which the force transferring part 502 is placed in the thoracic diaphragm D without the use of a diaphragm contacting part 501. The force transferring part is thus adapted to assist in the maintaining of an opening in the thoracic diaphragm D. The force transferring member 502 could be adapted to be in contact with the thoracic diaphragm D when the force transferring member is placed in the opening in the thoracic diaphragm D and thereby transferring force from the abdominal cavity to the thoracic cavity while sliding against the thoracic diaphragm D.

Figure 108A:
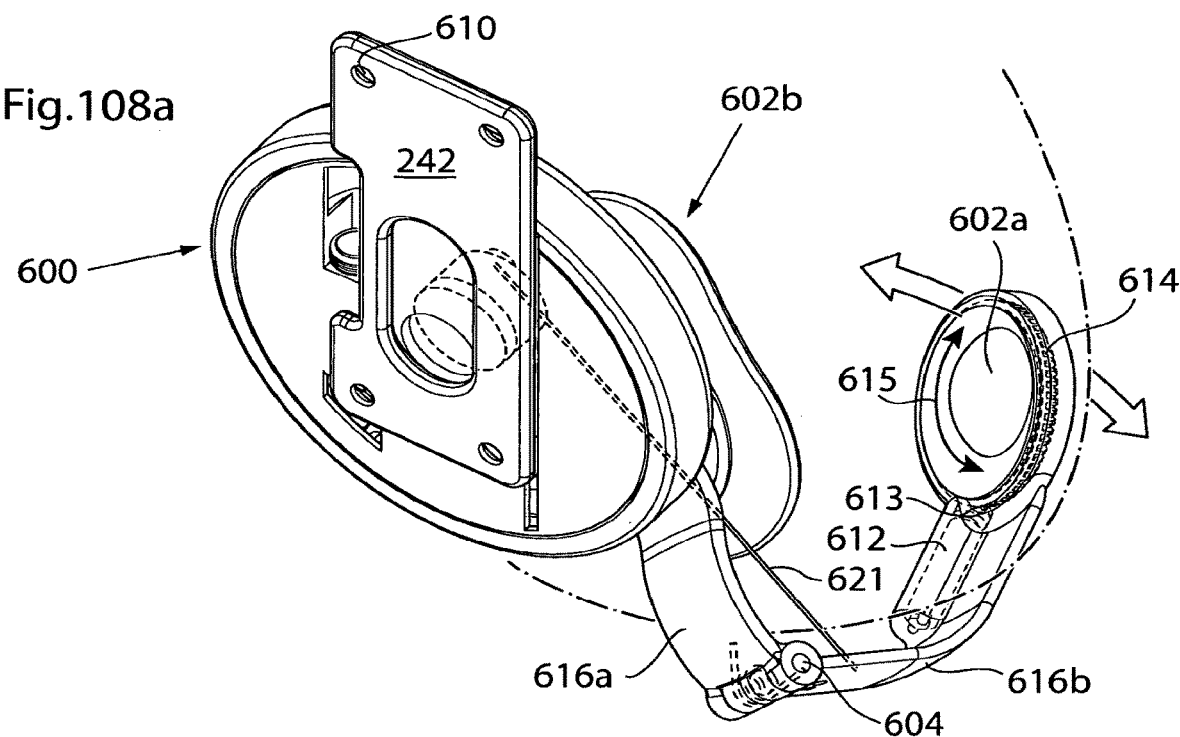
FIG. 108a shows a displaceable heart help device in a first perspective view.

FIG. 108a shows an embodiment of a heart help device adapted to exert a force on the heart. The heart help device comprises a fixation plate 242 for enabling fixation of the device to a part of the human body comprising bone though screws being placed in the fixation holes 610 in the plate 242. A magnetic operating device 600 is mounted onto the plate for operating the heart contacting organs 602a,b adapted to exert a force on the heart. According to some embodiments the heart contacting organs 602a,b are hydraulic or pneumatic cushions, the function thereof being described with reference to other figures herein. A first arm 616a connects the part comprising the operating device 600 to a hinged 604 second arm 616b which enables the movement of the second arm 616b in relation to the first arm 616a. A first heart contacting organ 602a is operably mounted to a plate 615 adapted to enable movement of the first heart contacting organ 602a for changing the location of the force exerted on the heart. The plate is operable by a gear connection 614; 613 between the plate 615 and a motor 612 adapted to operate the plate 615. The force exertion on the heart is performed by the operation device 600 being in connection with a driving member performing an eccentric rotating movement of a fixation point 609 to which a driving wire 621 is fixated and thereby pulling of the second hinged arm 616, thereby creating the movement exerting force on the heart. The heart help device is by this construction periodically exerting force on the heart muscle following the heart contractions and adding force thereto.

Figure 108B:
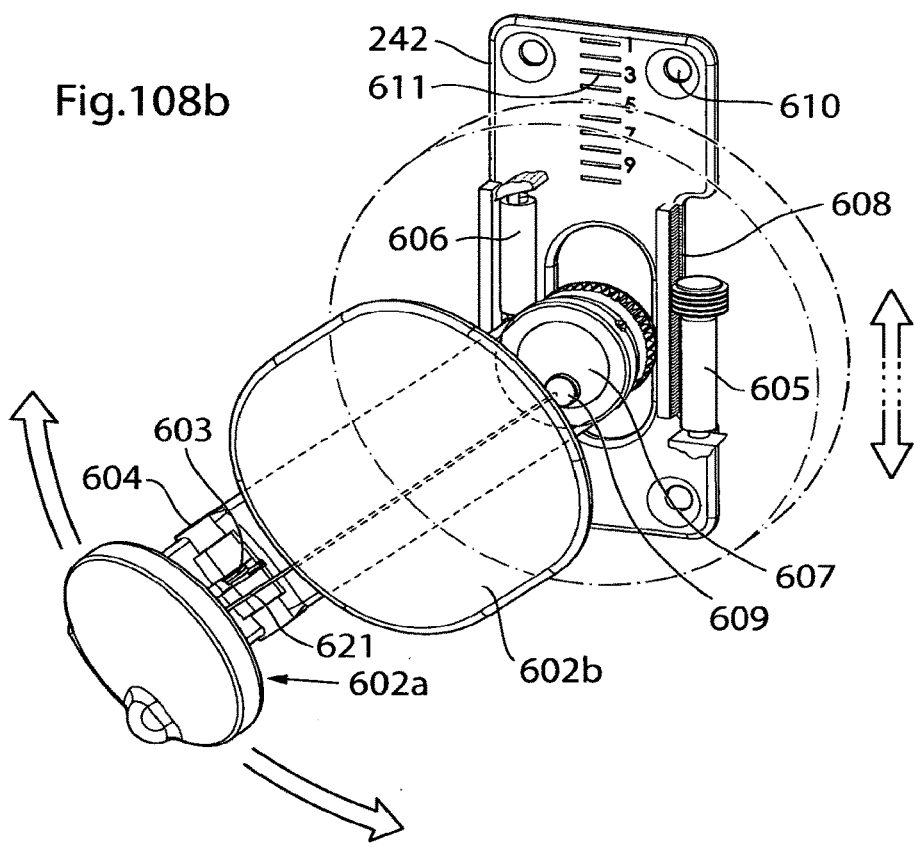
FIG. 108b shows a displaceable heart help device in a second perspective view.

FIG. 108b shows the implantable heart help device in a second view disclosing the movement functionality adapted to alter the position of the heart help device and the heart contacting organs, thereby altering the position of the force exerted on the heart, from a first area of the heart to a second area of the heart. The operating device comprises a first motor 605 adapted to affect a gear functionality 608 creating a translating movement of the heart pump device in relation to the fixation plate 242. The implantable device further comprises a unit 607 adapted to enable a rotating movement of the heart pump device in relation to the fixation plate 242. For securing the position the operating device further comprises a locking member 606 for locking the heart help device in a specific position for exerting force on the heart. The unit 607 further comprises the operating device adapted to rotate the eccentrically rotating fixation point 609 pulling on the operation wire 621 creating the force exerted on the heart. According to this embodiment the arms are spring loaded by a spring 603 in an outwards direction, which pulls the arms 616a,b apart after the operating wire 621 has pulled the arms 616a,b together. The entire system could be adapted to be controlled non invasively from the outside of the by, e.g. by means of a remote control. The system could then have sensor functionality for sending feedback on the location and operations of the device to outside the body, for example by means of wireless transfer. It is also conceivable that scale 611 is made from radiologically dense material thus enable the scale to be read on a radiological image.

FIG. 109 shows the operating device in further detail. The operating device comprises a first part 640 having a first surface, and a second part 641 having a second surface, and a third part 642 having a third surface. The second part is displaceable in relation to the second and third part. The first, second and third surfaces are adapted to abut each other, at least partially. The first part exerts indirectly force on an external part of the heart by the connection with the drive wire 621. The first, second and third surfaces are substantially parallel. The second part comprises magnets 15 and the first and third parts comprise coils 14 and the displacement of the second part is created through successive energizing of the coils 14. The force from the displacement is transferred to the dive wire through a gear system 643, 644 in connection with the eccentric drive member comprising the eccentrically rotating fixation member 609 in which the drive wire 621 is fixated.

Figure 110:
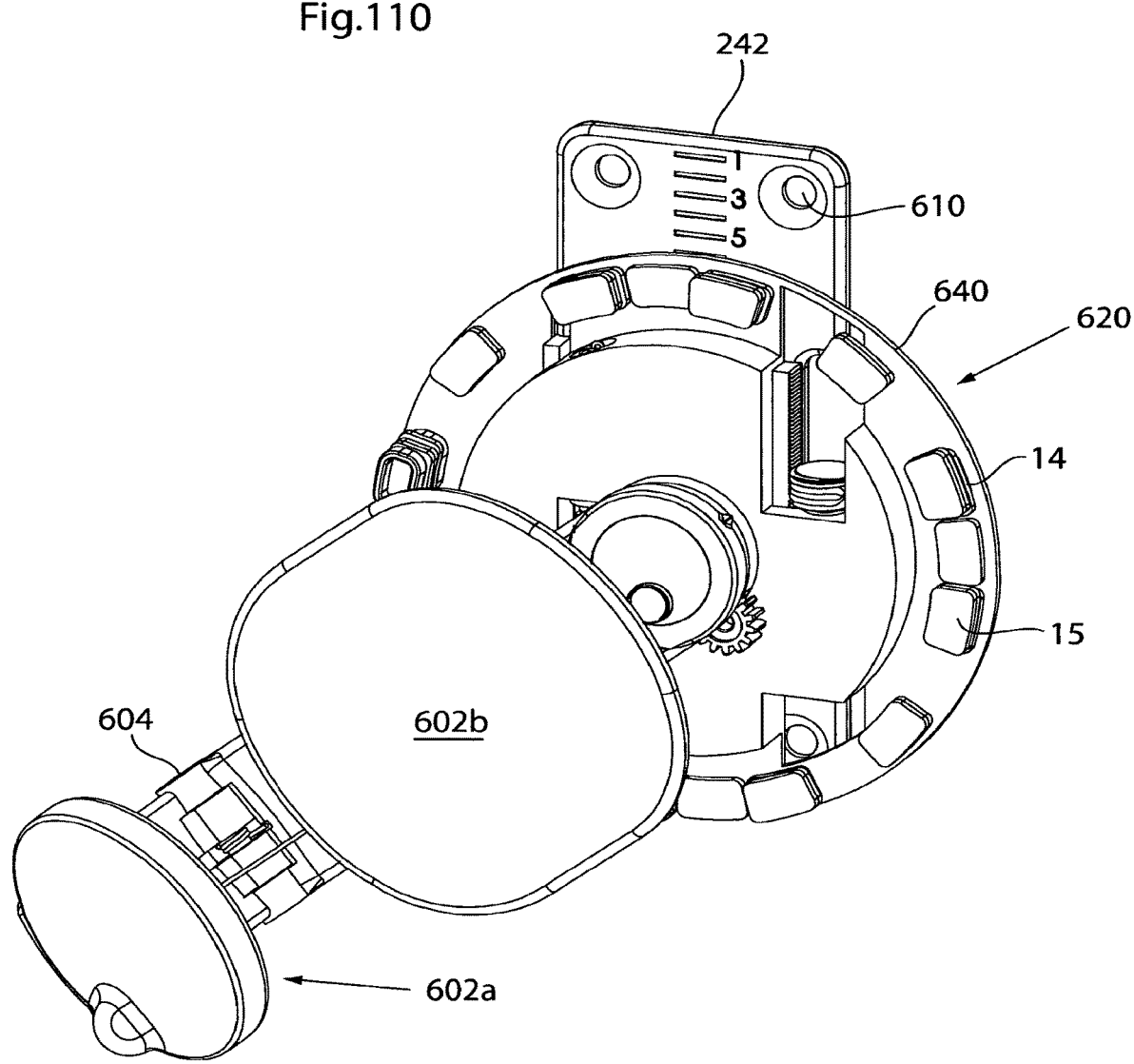
FIG. 110 shows a heart help device comprising a magnetic operating device in a perspective view.

FIG. 110 shows the first part 640 comprising coils 14 when the second plate has been removed, however the FIG. also shows the magnets 15 from the second plate, even though the second plate has been removed.

Figure 111:
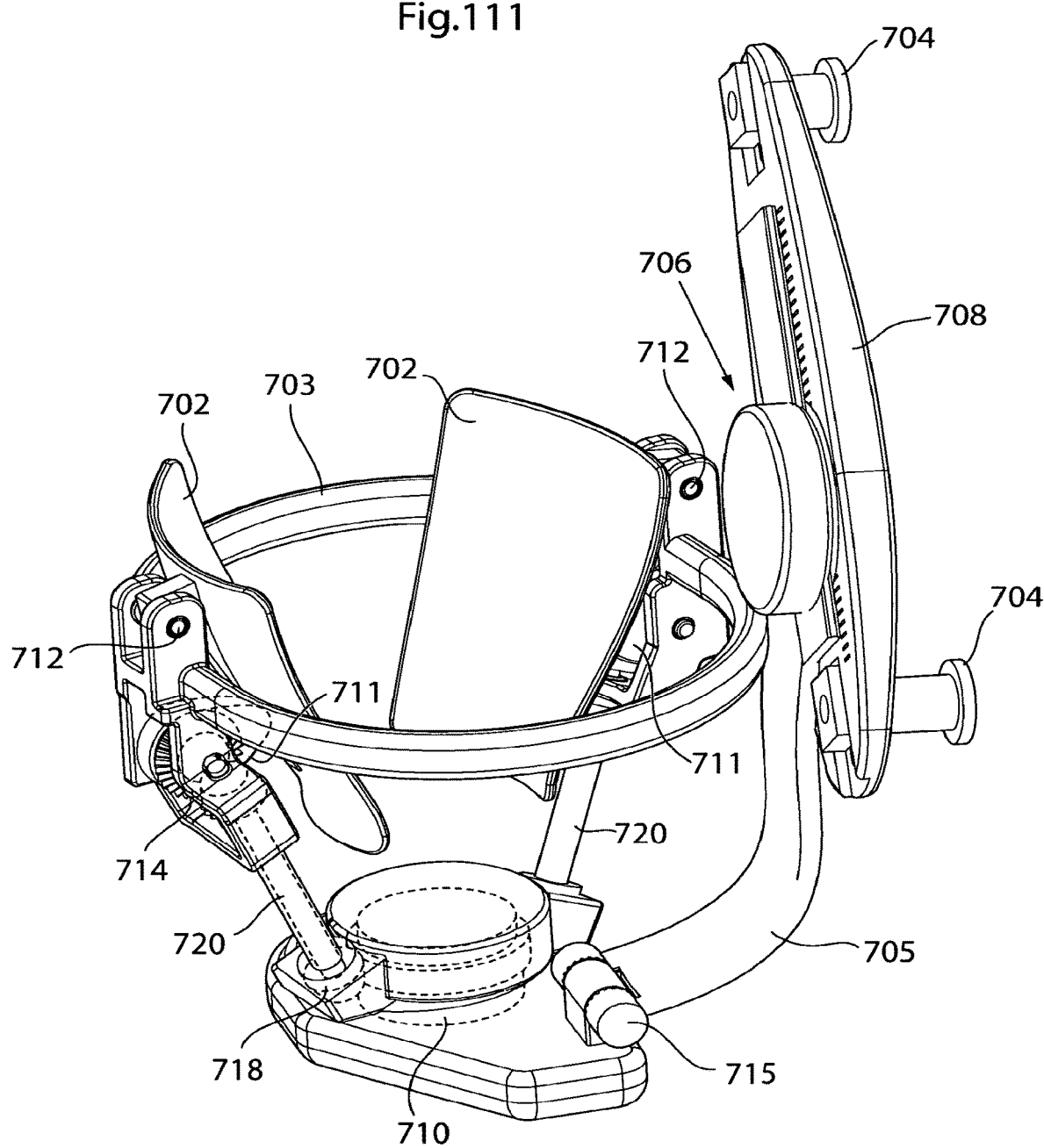
FIG. 111 shows a displaceable heart help device in a first perspective view.

FIG. 111 shows an embodiment of heart help device in which the heart help device comprises two heart contacting organs 702 which are adapted to exert a force on the anterior and posterior side of the heart H, respectively. The heart contacting organs 702 are pivotally arranged in a joint 712. One surface of the heart contacting organs 702 are in contact with an eccentrically rotating driving member 711 operated by an operating device 710 by a connection with a first gear system 718, which transfers force from the operating device 710 to a force transferring member 720 to a second gear system 714 in close connection to the eccentrically rotating member 711. The eccentrically rotating member and/or the surface of the heart contacting organs contacting the eccentrically rotating driving member could be made of a durable material, such as a ceramic material, for resisting the wear created by the constant connection of the eccentrically rotating member 711 with the heart contacting organ. The pump device of the implantable heart help device is hinged to an arm 705 connected to a device 706 enabling the movement of the heart pump device along a fixation plate 708 comprising two fixation members 704 for fixating the fixation plate 708 to a part of the human body comprising bone. The entire system could be adapted to be controlled non invasively from the outside of the by, e.g. by means of a remote control. The system could then have sensor functionality for sending feedback on the location and operations of the device to outside the body, for example by means of wireless transfer.

Figure 112A:
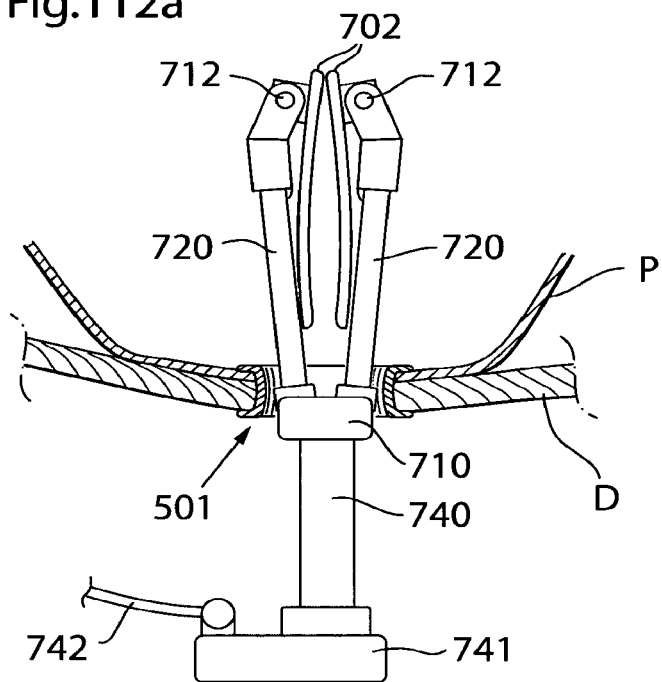
FIG. 112a shows a heart help device adapted to be inserted through an opening in the thoracic diaphragm, in its folded state.

FIG. 112a shows an embodiment of the heart help device similar to the device shown with reference to FIG. 111. However the device according to FIG. 11a is adapted to enter the pericardium P from the abdomen in the area of the thoracic diaphragm D to which the pericardium P rests and is fixated. This method of placement enables the placement of the device without entering into the thorax of the patient, facilitating the procedure. The device is fixated to a part of the human body comprising bone through a fixation arm 742 which in turn supports an operation device 741 placed in the abdomen of the patient. The operation device 741 transfers force through a force transferring member 740 connected to a linking part 710 to which two force transferring members 720 are attached. The device is adapted to travel through an opening in the thoracic diaphragm D being maintained by a diaphragm contacting part 501 fixated to the thoracic diaphragm D and the pericardium P.

Figure 112B:
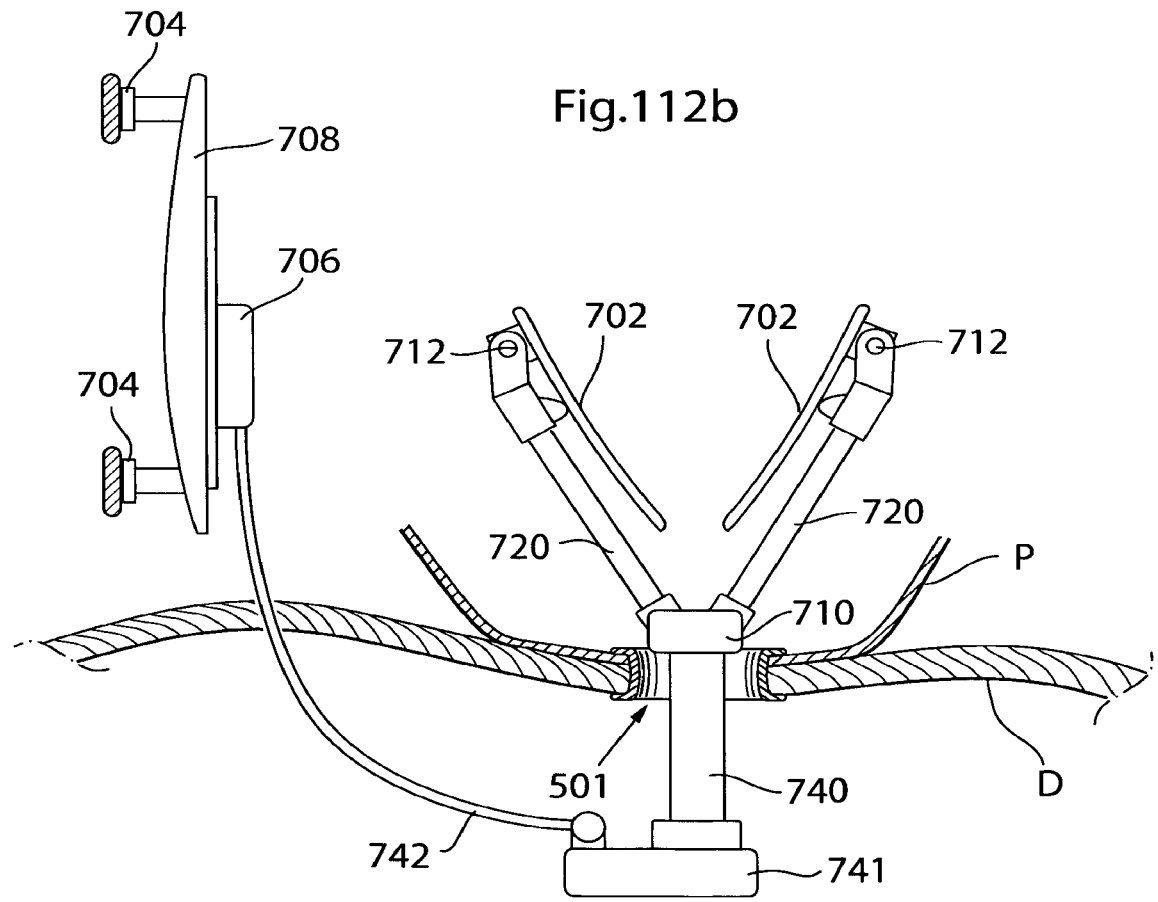
FIG. 112b shows a heart help device adapted to be inserted through an opening in the thoracic diaphragm, in its unfolded state.

FIG. 112b shows the device of FIG. 112b in its unfolded state with the operation device 741 fixated to the a fixation plate 708 by means of a connecting arm 742 which according to this embodiment is operable by means of a position operation device 706 to alter the position of the heart help device in relation to the fixation plate 708. The features of other embodiments such as the respiratory movement compensator, the pericardial drain and the fibrotic tissue movement structure disclosed, with reference to FIG. 97b are of equal relevance and could be included in the embodiments of FIGS. 112a,b.

FIG. 113 shows a flow-chart of an operation method which could comprise the steps of: 1) dissecting a part of the human body comprising bone and 2) fixating a fixating member to the bone, such that the fixation member is placed in contact with the connection arm. In one embodiment of this surgical procedure the method further comprises the steps of 3) creating an opening in the thoracic diaphragm and 4) inserting the connecting arm into the thorax through the opening in the thoracic diaphragm. This diaphragm approach enables a surgeon to place a heart help device in the pericardium of thorax without opening the thorax. The method could further comprise the step of placing an operation device in the abdomen of the patient, transferring force to through an opening in the thoracic diaphragm and into the thorax for operating a hart help device placed in thorax.

Please note that in the detailed description above any embodiment or feature of an embodiment as well as any method or step of a method could be combined in any way if such combination is not clearly contradictory. Please also note that the description in general should be seen as describing both an apparatus/device adapted to perform a method as well as this method in itself.

I claim:

1. An implantable heart help device for assisting the pump function of the heart by exerting an external force on the heart, wherein said implantable device comprises;
   a first fixating member adapted to be fixated to a bone in a patient,
   a second fixating member,
   at least one heart pump device in contact with said second fixating member, and wherein said second fixating member is displaceable in relation to said first fixating member for changing the position of said heart pimp device, and
   a locking member adapted to lock said second fixating ember in a position in relation to said first fixating member.

2. The implantable device according to claim 1, wherein said fixating member is rotationally displaceable in relation to said first fixating member.

3. The implantable device according to claim 1, wherein said second fixating member is linearly displaceable in relation to said first fixating member.

4. The implantable device according to claim 1 wherein said second fixating member is displaceable in relation to first said fixating member in at least a first and second axis.

5. The is device according to claim 1, wherein said second fixating member is displaceable in relation to first said fixating member in at least a first, second and third axis.

6. The implantable heart help device according to claim 1 wherein said first fixating member is adapted to be fixated to a sternum on the anterior side thereof, and wherein said heart pump device is adapted to be located on the posterior side of the rib cage, and wherein said second fixating member to be in contact with said first fixation member on the anterior side of the sternum and to be in contact with said heart pump device on the posterior side of the rib cage.

7. The implantable heart help device according to claim 1 wherein said first fixating member comprises a first plate adapted be fixated to a sternum, and wherein said second fixating member comprises a second plate adapted be fixated to the sternum, and wherein said first fixating member is adapted to be located on the anterior side of the sternum, and said second fixating member is adapted to be located on the posterior side of the sternum.

8. The device according to claim 1, wherein said heart help device is operable to change the position of the external force exerted on the heart.

9. The implantable heart help device according to claim 8, wherein said heart help, device is operable using an implantable motor, being a motor selected front;
- an electric motor,
- a magnetic motor comprising a first part comprising coils, and a second part comprising magnets, and being adapted to create a force by successive energizing of said coils in connection with the magnets,
- a solenoid,
- a hydraulic rotor,
- a pneumatic motor, and
- a servo motor.

10. The implantable heart help device according to claim 1, wherein said first fixating member is adapted to be fixated to the posterior side of a sternum using at least one of: at least one screw, at least one pop-rivet, and at least one through-going arrangement.

11. The implantable heart help device according to claim 1, wherein said first fixating member is, adapted to be at least one of: fixated to the posterior cortex of a sternum, fixated to both the posterior and the anterior cortex of the sternum, and fixates to the sternum in more than one point.

12. The implantable heart help device according to claim 1, wherein said second fixating member is displaceable in relation to said first fixating member for calibrating the location of the applied external force on the heart of a human patient.

13. The implantable heart help device according to claim 1, wherein said first fixating member comprises a first and second, plate, and wherein said first plate is adapted to be placed on an anterior side of sternum and said second plate is adapted to be placed on the posterior side of the sternum, and wherein said first and second plates are adapted to be attached to each other and thereby clamp the sternum.

14. The implantable device according to claim 1, wherein the first fixation member comprises at least one of: a ceramic material, titanium, and stainless steel.

15. The implantable device according to claim 1, wherein said implantable device is adapted to exert an external force on at least one of:
- the left ventricle of the heart,
- two different sides of the left ventricle of the heart,
- the right ventricle of the heart and
- two different sides of the right ventricle of the heart.

16. The implantable device according to claim 1, further comprises an internal energy receiver, adapted to be energized non-invasively and wirelessly by energy transmission device from outside the patient's body.

17. The implantable device according to claim 1, further comprises an implantable internal energy source.

* * * * *